(12) United States Patent
Hall

(10) Patent No.: US 6,919,382 B2
(45) Date of Patent: Jul. 19, 2005

(54) PREPARATION AND USES OF CONJUGATED SOLID SUPPORTS FOR BORONIC ACIDS

(75) Inventor: Dennis G. Hall, Edmonton (CA)

(73) Assignee: The Governors of the University of Alberta, Alberta (CA)

(*) Notice: Subject to any disclaimer, the term of this patent is extended or adjusted under 35 U.S.C. 154(b) by 118 days.

(21) Appl. No.: 09/943,465

(22) Filed: Aug. 31, 2001

(65) Prior Publication Data

US 2003/0044840 A1 Mar. 6, 2003

Related U.S. Application Data

(60) Provisional application No. 60/229,833, filed on Aug. 31, 2000, and provisional application No. 60/235,386, filed on Sep. 25, 2000.

(51) Int. Cl.[7] .................................................. C08J 5/20
(52) U.S. Cl. ........................... 521/25; 521/26; 521/27; 521/28; 521/29; 521/30; 521/31; 521/32; 521/33; 521/34; 521/35; 521/36; 521/37; 521/38; 525/332.2; 525/333.3; 525/333.4; 525/333.5; 525/333.6
(58) Field of Search .......................... 525/332.2, 333.3, 525/333.4, 333.5, 333.6; 521/25, 26, 27, 28, 29, 30, 31, 32, 33, 34, 35, 36, 37, 38

(56) References Cited

U.S. PATENT DOCUMENTS

| | | |
|---|---|---|
| 4,355,153 A | 10/1982 | Radici et al. |
| 4,652,613 A | 3/1987 | Collins et al. |
| 5,032,266 A | 7/1991 | Kirkland et al. |
| 5,128,114 A | 7/1992 | Schwartz |
| 5,290,819 A | 3/1994 | Witt et al. |
| 5,525,637 A | 6/1996 | Henn et al. |
| 5,591,778 A | 1/1997 | Scherzer et al. |
| 5,594,111 A | 1/1997 | Stolowitz |
| 5,594,151 A | 1/1997 | Stolowitz |
| 5,604,163 A | 2/1997 | Endo et al. |
| 5,609,957 A | 3/1997 | Page et al. |
| 5,623,055 A | 4/1997 | Stolowitz |
| 5,648,470 A | 7/1997 | Stolowitz |
| 5,668,257 A | 9/1997 | Stolowitz |
| 5,668,258 A | 9/1997 | Stolowitz |
| 5,677,431 A | 10/1997 | Stolowitz |
| 5,688,928 A | 11/1997 | Stolowitz |
| 5,739,319 A | 4/1998 | Yamasaki |
| 5,744,627 A | 4/1998 | Stolowitz et al. |
| 5,767,238 A | 6/1998 | Caporale |
| 5,777,148 A | 7/1998 | Stowolitz et al. |
| 5,780,454 A | 7/1998 | Adams et al. |
| 5,795,557 A | 8/1998 | Pajonk et al. |
| 5,831,045 A | 11/1998 | Stolowitz et al. |
| 5,831,046 A | 11/1998 | Stolowitz et al. |
| 5,840,677 A | 11/1998 | Nielsen et al. |
| 5,843,767 A | 12/1998 | Beattie |
| 5,880,166 A | 3/1999 | Glueck et al. |
| 5,900,146 A | 5/1999 | Ballard et al. |
| 5,917,185 A | 6/1999 | Yeung et al. |
| 5,929,229 A | 7/1999 | Edgar et al. |
| 5,939,261 A | 8/1999 | Loewy et al. |
| 5,980,839 A | 11/1999 | Bier et al. |
| 6,013,783 A | 1/2000 | Kaiser et al. |
| 6,024,872 A | 2/2000 | Mahendran et al. |
| 6,025,371 A | 2/2000 | Gordeev et al. |
| 6,031,117 A | 2/2000 | Kaiser et al. |
| 6,037,490 A | 3/2000 | Kabalka et al. |
| 6,048,577 A | 4/2000 | Garg |
| 6,053,012 A | 4/2000 | Itoh |
| 6,054,047 A | 4/2000 | Hindsgaul et al. |
| 6,071,838 A | 6/2000 | Endo et al. |
| 6,074,983 A | 6/2000 | Derolf et al. |
| 6,075,126 A | 6/2000 | Stolowitz et al. |
| 6,075,166 A | 6/2000 | Garigipati et al. |
| 6,083,903 A | 7/2000 | Adams et al. |
| 6,086,740 A | 7/2000 | Kennedy |
| 6,096,496 A | 8/2000 | Frankel |
| 6,096,817 A | 8/2000 | McNamara |
| 6,103,885 A | 8/2000 | Batelaan et al. |

OTHER PUBLICATIONS

Che et al., Hecheng Hauxve,6(1), p. 148–151, 1998.
Che et al., Fenzl Cuihua, 12(2), p. 69–74, 1998.
Raju et al., Tetrahedron Letters, 38(28), p. 4965–4968, 1997.
Adrian et al., Tetrahedron, 54, p. 3581–3588, 1998.
Berteina et al., Snylett, p. 1231–1233, Nov. 1998.
Hird et al., Tetrahedron Letters, 40, p. 7111–7114, 1997.
Stangier et al., Snylett, p. 179–181, Feb. 1996.
Marx et al., J. Am. Chem. Soc., 119, p. 6153–6167, 1997.
Conti et al., Tetrahedron Letters, 38(16), p.2915–2918, 1997.
Dankwardt et al., Tetrahedron Letters, 36(28), p. 4923–4926, 1995.
Haga, Chemical Abstracts, 132(14), No. 180563m, 2000.
Wilson, Chemical Abstracts No. 59262e, vol. 133.
Arimori et al., Tetrahedron Letters, 41, p. 10291–10294, 2000.
Hall et al., Angew. Chem. Int. Ed. 38(20), p. 3064–3067, 1999.
Hall et al., Abstract No. 429, A.C.S. National Meeting, Mar. 2000.

(Continued)

Primary Examiner—Bernard Lipman
(74) Attorney, Agent, or Firm—Ogilvy Renault

(57) ABSTRACT

The invention provides novel solid supports comprising dihydroxyalkyl aminoalkyl and dihydroxyalkylaminobenzyl groups, and methods for making and using them. The supports are particularly useful for immobilizing and derivatizing functionalized boronic acids for use in solid phase synthesis, such as those used in combinatorial chemistries. The compositions and methods of the invention are also useful as scavenger solid supports, e.g., in solution-phase parallel synthesis of small molecule libraries, and for use in resin-to-resin transfer reactions via phase transfer of solid supported boronic acids under both aqueous and anhydrous conditions. The methods of the invention provide convergent solid-phase synthesis of symmetrically or unsymmetrically functionalized compounds, such as biphenyl compounds. Also provided are synthesizer devices, e.g., semiautomated parallel synthesizers.

7 Claims, 14 Drawing Sheets

OTHER PUBLICATIONS

Gravel et al., J. Comb. Chem. 2, p. 228–231, 2000.
Thompson et al., Chem. Commun., p.2379–2380, 2000.
Wulff, Pure Appl. Chem. 1982, 2093–2101.
James et al., Angew Chem. Int. Ed. Engl. 1996, 35, 1910–1922.
Kettner et al., J. Biol. Chem. 1984, 259, 15106–15114.
Martichonok et al., J. Am. Chem. Soc. 1996, 118, 950–958.
Tian et al., J. Org. Chem. 1997, 62, 514–522.
Zhong et al., J. Am. Chem. Soc. 1995, 117, 7048–7055.
Priestley et al., Org. Lett. 2000, 2, 3095–3097.
Barth et al., Sci. Am. 1990, 263, 100–107.
Hawthorne, Angew. Chem. Int. Ed. Engl. 1993, 32, 950–984.
Mehta et al., Pharm. Res. 1996, 13(3), 344–351.
Soloway et al., Chem. Rev. 1998, 1515–1562.
Smith et al., Adv. Supramol. Chem. 1999, 5, 157–202.
Suzuki, Organometal. Chem. 1999, 576, 147–168.
Suzuki, A., in "Metal–catalyzed Cross–coupling Reactions", Eds. Diederich, F. et al., Wiley–VCH, 1997, Chapt. 2.
Lappert, M.F., Chem. Rev. 1956, 56, 959–1065.
Duncia (1992) Medical Research Reviews 12(2) 149–191.
Snyder et al., J. Am. Chem. Soc. 1938, 60, 105–111.
Matteson, J. Am. Chem. Soc. 1960, 82, 4228–4233.
Matteson, D.S., Stereodirected Synthesis with Organoboranes, Springer:1995, Berlin, Heidelberg, p. 17 (section 1.4.2).
Frenette (1994) Tetrahedron Lett. 35(49), 9177–9180.
Huwe (1999) Tetrahedron Lett. 40, 683–686.
Chamoin (1998) Tetrahedron Lett. 39, 4179–4182.
Hamuro (1999) J. Am. Chem. Soc. 121, 1636–1644.
Sundaram (1969) Bull. Chem. Soc. Jpn. 42, 3141–3147.
Bedingfield (1995) J. Pharmacol. 116, 3323–3330.
Chan (1998) Tetrahedron Lett. 39, 2933–2936.
Petasis (1998) J. Am. Chem. Soc. 120, 11798–11799.
Barrett (2000) Org. Lett. 2(19), 2999–3001.
Stachel (2000) Org. Lett. 2(11), 1637–1639.
Falkiewicz (1999) Nucleic Acids Symp. Ser. 42, 9–10.
Wisniewski (1998) J. Pept. Sci. 4, 1–14.
Organic Synthesis Collective Volumes. Gilman et al. (Eds) John Wiley & Sons, Inc., NY; Venuti (1989) Pharm Res. 6(10), 867–873.
Ugi, I.; Doemling, A.; Hoerl, W., Endeavour 1994, 18(3), 115–122.
Rana et al., J. Comb. Chem. 2001, 3, 9–15.
Bhattacharyya (2000) Comb. Chem. High Throughput Screen. 3, 117–124.
South (2000) Comb. Chem. High Throughput Screen. 3, 139–151.
South (2000) Biotechnol. Bioeng. 71(1), 51–57.
Davis (2000) Biotechnol. Bioeng. 71(1), 19–27.
Kaiser (1970) Anal. Biochem. 34, 595–598.
Philipp (1971) Proc. Nat. Acad. Sci. USA 68(2), 478–480.
Wendeborn (1998) Synlett p. 671–675.
Brown (1972) J. Am. Chem. Soc. 94:12, p. 4370–4371.
Vaultier (1987), Tetrahedron Letters 28(36), p. 4169–4172.
Hamuro (1999) J. Am. Chem. Soc. 121, 1636–1644.
Tsuji, J., Palladium Reagents and Catalysts; Wiley: Chichester, UK, 1995.
Woods, W.G.; Bengelsdorf, I.S.; Hunter, D.L., J. Org. Chem. 1966, 31, 2766–2768.
Carboni, et al., "Boronic ester as a linker system for solid phase synthesis", Tetrahedron Letters, 49 (1999) 7979–7983.
Gravel, et al., "Universal solid–phase approach for the immobilization, derivitization, and resin–to–resin transfer reactions to boronic acids", J. Org. Chem. 2002, 67, 3–15.
Weidmann, et al., Annalen Der Chemie—Justus Liebig, 619(1–3), 28–35 (1958).
"Quench Resin for Metal Scavenging PS–DEAM", Argonaut (Foster City, CA), Chemical and Engineering News, vol. 18, No. 11, Mar. 18, 2002.
PS–DEAM, copyright 2001 [retrieved in 2001 from the website of Argonaut Technologies] using Internet <URL: http://www.argotech.com/resins/files/PS–DEAM.htm>.
Solution Phase Reagents Selection Table [retrieved on Nov. 30, 2004] using Internet <URL:http://www.argotech.com/products/lead/resins/solution_table.html>.
Product Description entitled "Polymer Bound Diethanolamine PS–DEAM" [retrieved Nov. 30, 2004] using Internet<URL:http://www.argotech.com/PDF/resins/ps_deam_tech.pdf>.
Letters No. 4/01, dated 2001, pp 1–4 [retrieved Nov. 30, 2004] using Internet <URL: http://www.amdbiosciences.com/SharedImages/TechnicalLiterature/6_401letterweb.pdf>.
Technical Bulletin R002 entitled PL–DEAM Resin, [retrieved on Nov. 30, 2004] using Internet <URL: http://www.polymerlabs.com/stratosphere/bulletins/R002.pdf>.

Scheme 1

Scheme 2

19{1} X = H
19{2} X = Cl
19{3} X = OMe

20{1} Ar = Ph    20{2} Ar = 4-Cl-C$_6$H$_4$    20{3} Ar = 4-MeO-C$_6$H$_4$

11 / \ 16    11 / \ 16    11 / \ 16

21{1}  22{1}    21{2}  22{2}    21{3}  22{3}

21{1} Ar = Ph (99%)
21{2} Ar = 4-Cl-C$_6$H$_4$ (100%)
21{3} Ar = 4-MeO-C$_6$H$_4$ (90%)

22{1} Ar = Ph (98%)
22{2} Ar = 4-Cl-C$_6$H$_4$ (75%)
22{3} Ar = 4-MeO-C$_6$H$_4$ (89%)

$$K_{eq} = \frac{[1]\,[RB(OH)_2]}{[2]\,[H_2O]^2}$$

11 o-, 12 m-, 13 p-    7 o-, 8 m-, 9 p-

14 o-, 15 m-, 16 p-    17 o-, 18 m-, 19 p-

20 o-, 21 m-, 22 p-    23 o-, 24 m-, 25 p-

20 o-, 21 m-, 22 p-

26 o-, 27a-d m-, 28 p-
X = S: 27e (51%, 90% purity)

X = alkyl/aryl (23)
R = H or CH₃

PREPARATION AND USES OF CONJUGATED SOLID SUPPORTS FOR BORONIC ACIDS

CROSS REFERENCE TO RELATED APPLICATIONS

This application claims priority from U.S. provisional application Ser. No. 60/229,833, filed Aug. 31, 2000, and U.S. provisional application Ser. No. 60/235,386, filed Sep. 25, 2000, the entire contents of which are incorporated herein by reference.

TECHNICAL FIELD

This invention generally relates the fields of chemistry and pharmaceutical drug preparation. In particular, the invention is directed to dihydroxyalkylaminoalkyl- and dihydroxyalkylaminobenzyl-conjugated solid supports and methods for making and using them, particularly, for the immobilization, purification and derivatization of boronic acids.

BACKGROUND

Boronic acid containing molecules, such as arylboronic acids, are employed in a broad range of biological, medicinal and synthetic applications, including pharmaceutical compositions.

They are employed in applications such as carbohydrate recognition (for recent reviews see, e.g., Wulff, *Pure Appl. Chem.* 1982, 2093–2102; James et al., *Angew. Chem. Int. Ed. Engl.* 1996, 35, 1910–1922). Also, arylboronic acids can be crucial synthetic intermediates or potential inhibitors of therapeutically relevant serine protease enzymes (for recent examples see, e.g., Kettner et al., *J. Biol. Chem.* 1984, 259, 15106; Martichonok et al., *J. Am. Chem. Soc.* 1996, 118, 950–958; Tian et al.; *J. Org. Chem.* 1997, 62, 514–522; Zhong et al., *J. Am. Chem. Soc.* 1995, 117, 7048; Priestley et al., *Org. Lett.* 2000, 2, 3095–3097). Boronic acids have also been applied in neutron capture therapy for cancer (for reviews see, e.g., Barth et al., *Sci. Am.* 1990, 263, 68–73; Hawthorne, *Angew. Chem. Int. Ed. Engl.* 1993, 32, 950–984; Mehta et al., *Pharm. Res.* 1996, 13, 344–351; Soloway et al., *Chem. Rev.* 1998, 1515–1562), and as transmembrane transport agents (for a recent review, see, e.g., Smith et al., *Adv. Supramol. Chem.* 1999, 5, 157–202 and references cited therein).

In recent years, boronic acids have also gained tremendous popularity as substrates and building blocks in organic synthesis and combinatorial chemistry. They have found widespread use in Suzuki cross-coupling reactions (see, e.g., Suzuki, *Organometal. Chem.* 1999, 576, 147–168; Suzuki, A., in "Metal-catalyzed Cross-coupling Reactions", Eds. Diederich, F., et al., Wiley-VCH, 1997, Chapt. 2). Suzuki cross-coupling reactions (see, e.g., Suzuki (1999) Organometal. Chem. 576:147–168; Suzuki, A., in Metal-catalyzed cross-coupling reactions, Eds. Diederich, F., et al., Wiley-VCH, 1997, Chapt. 2) are commonly used in industrial and pharmaceutical chemistries. They can also provide novel biphenyl units, such as those represented in several biologically active molecules (see, e.g., Duncia (1992) Medical Research Reviews 12:149). Many new types of synthetic transformations that use boronic acids have created a demand for the commercial availability of a larger number of functionalized boronic acids.

However, in spite of the demand for boronic acids, particularly arylboronic acids, and conjugated forms of these compounds, there remains a shortage of commercially available supplies. The paucity of boronic acids can be explained by the non-existence of natural ones, and in large part by difficulties associated with the synthesis and derivatization of even the simplest functionalized ones by solution-phase methods.

The isolation of compounds containing a boronic acid functionality can prove notoriously troublesome due to their amphiphilic character. These problems are amplified when the desired boronic acid-containing compound comprises other sites with basic or acidic functionalities. Boronic acids are also typically slow moving on silica gel, and consequently must often be purified by recrystallization. In addition, boronic acids can be sensitive to oxidation (see, e.g., Snyder et al., *J. Am. Chem. Soc.* 1938, 60, 105–111; Matteson, *J. Am. Chem. Soc.* 1960, 82, 4228–4233). Some of these problems can be alleviated by protection of the boronic group as an ester (see, e.g., Matteson, D. S. *Stereodirected Synthesis with Organoboranes*, Springer:1995, Berlin, Heidelberg, p. 17 (section 1.4.2). However, these approaches require additional synthetic operations.

Solid-phase methods circumvent the need for aqueous work-up and other time-consuming operations required to isolate the desired boronic acid from excess reagents and by-products. Solid-phase Suzuki reactions in "one resin-bound substrate" schemes have been described, e.g., by Frenette (1994) Tetrahedron Lett. 35:9177–9180; Huwe (1999) Tetrahedron Lett. 40:683–686; Chamoin (1998) Tetrahedron Lett. 39:4179–4182. Two resin systems, also called resin-to-resin transfer reactions (RRTR), constitutes a significant simplification of solid-phase organic synthesis (SPOS). RRTR can be extremely valuable as a time saving strategy in combinatorial chemistry (see, e.g., Hamuro (1999) J. Am. Chem. Soc. 121:1636–1644). In RRTR, one resin-bound substrate is transferred to solution-phase by action of a phase-transfer agent or chaperone, and coupled in situ to another resin-bound substrate.

In view of all the above mentioned impediments in handling boronic acid containing molecules by solution-phase methods, it is clear that simple and general solid-phase approaches for their use, immobilization and derivatization would be of tremendous usefulness.

SUMMARY

The invention provides novel solid supports comprising dihydroxyalkyaminoalkyl and dihydroxyalkylaminobenzyl groups and methods for making and using them. These compositions are particularly useful for immobilizing boronic acids for use in solid phase chemical reactions, e.g., solid-phase synthesis, such as those used in combinatorial chemistries. For example, the compositions and methods of the invention are also useful as "scavenger" or "fishing out" solid supports, e.g., in solution-phase parallel synthesis of small molecule libraries.

The invention provides a solid support derivatized with a dihydroxyalkylaminoalkyl group or a dihydroxyalkylaminobenzyl group, wherein the dihydroxyalkylamino moiety comprises a tertiary amine having two hydroxyalkyl substituents having a formula HO $(CH_2)_x$N $(CH_2)_y$ OH, wherein x and y are integers between 1 to about 20. In one preferred embodiment, the dihydroxyalkylaminoalkyl is a dihydroxyalkylaminomethyl group or a dihydroxyalkylaminobenzyl group. In one embodiment, the dihydroxyalkylaminoalkyl group can be a dihydroxyalkylaminoethyl, a dihydroxyalkylaminopropyl, a dihydroxyalkylaminobutyl group. In one preferred embodiment, the dihydroxyalkylamino moiety can be a diethanolamine.

In another embodiment, the solid-supported group is a dihydroxyalkylaminobenzyl group.

In one embodiment, the solid support comprises a polystyrene or an equivalent composition. The polystyrene can be a poly(styrene-divinylbenzene) (PS-DVB) or an equivalent composition. In one preferred embodiment, the polystyrene is cross-liked with about 1% to 2% divinylbenzene.

In alternative embodiments, the solid support comprises a plastic or a plastic co-polymer or an equivalent thereof. The solid support can comprise a silica or a silica gel or an equivalent thereof. The solid support can comprise a cellulose or a cellulose acetate or an equivalent thereof. The solid support can comprise a polyphenol, a polyvinyl a polypropylene, a polyester, a polyethylene, a polyethylene glycol, a polystyrene-copolymer, or an equivalent thereof, or a co-polymeric mixture thereof. The solid support can comprise a poly(vinyl alcohol) (PVA) hydrogel, or an equivalent composition. 1% PS-DV6 is an example of this type of support. In one preferred embodiment, the solid support may comprise a polystyrene-polethylene glycol copolymer, e.g. Tantagel® or Argogel®.

In one embodiment, the solid supports of the present invention can comprise a POEPOP (polyoxyethylene/polyoxypropylene copolymer) or a SPOCC (superpermeable organic combinatorial chemistry resin).

In one embodiment, the solid support can comprise a polyacrylamide or an equivalent polymer composition. The polyacrylamide can comprise a polymethacrylamide, a methyl methacrylate, a glycidyl methacrylate, a dialkylaminoalkyl-(meth)acrylate, or an N,N-dialkyl-aminoalkyl(meth)acrylate, or an equivalent composition.

Alternatively, the solid support can comprise an inorganic composition selected from the group consisting of sand, silica, silica gel, glass, glass fibers, gold, alumina, zirconia, titania, and nickel oxide and combinations thereof and equivalents thereof.

In one embodiment, the solid supports of the invention further comprise a boronic acid attached as a boronic ester-dioxyalkylaminoalkyl- or -dihydroxyalkylamino-benzyl-conjugated support. The boronic acid can be an arylboronic acid. In one preferred embodiment, the boronic acid is a functionalized boronic acid, e.g., carboxy-functionalized-boronic acid, bromomethyl functionalized boronic acid, formyl-functionalized boronic acid, aniline-functionalized boronic acid.

In one preferred embodiment, the solid support comprises N,N-diethanolaminomethyl-conjugated polystyrene (DEAM-PS). In one preferred embodiment, the cross-linking is about 1% to 2%.

The invention also provides a solid support derivatized with a dihydroxyalkylamine moiety made by the process comprising mixing an aminoalkylated or aminobenzylated solid support comprising a primary amino group, with an excess of an epoxide, and a solvent, thereby derivatizing the solid support with a dihydroxyalkylamine moiety comprising a tertiary amine having two hydroxyethyl substituents.

In one embodiment, the solid support is made by a process comprising mixing an aminoalkylated solid support comprising a primary amino group with an excess ethylene oxide at about 50° C. in a solvent comprising a tetrahydrofuran/water mixture, or equivalent, or dioxane, or equivalent, in a sealed, pressure resistant container, thereby derivatizing the solid support with a diethanolaminoalkyl group comprising a tertiary amine having two hydroxyethyl substituents and a formula HO $(CH_2)_2$N $(CH_2)_2$ OH. In one embodiment, the aminoalkylated solid support is an aminomethylated solid support. The ethylene oxide can be in the sealed, pressure resistant container as a gas; the pressure of the ethylene oxide gas can be at about 1 to about 20 atmospheres. In one embodiment, the dihydroxyalkylamino moiety can be a diethanolamine or a dipropanolamine. In one embodiment, the solvent is at a concentration of about 0.1 to about 1 M. The mixing can last for about 12 hours to about 72 hours. The solid support can be a polystyrene or an equivalent composition.

In other embodiments, the epoxide comprises isobutylene oxide and the reaction takes place at 80° C. In yet other embodiments, the epoxide comprises an aryl-substituted epoxide. In yet another embodiment, the epoxide comprises styrene oxide.

In one embodiment, the invention provides a boronic ester-dioxyalkylaminoalkyl- or boronic-ester-dioxyalkyl-aminobenzyl-conjugated solid support with a formula

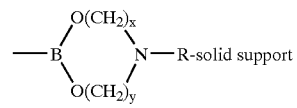

wherein x and y are integers between 1 to about 20, and R is an alkyl, substituted alkyl, or benzyl group. The boronic ester can be an aryl boronic ester, a vinylboronic ester or an alkylboronic ester.

The invention provides a solid support derivatized with a boronic ester-dialkylaminoalkyl or -dialkylaminobenzyl-group made by a process comprising the following steps: (a) mixing an aminoalkylated or aminobenzylated solid support comprising a primary amino group with excess ethylene oxide at about 50° C. in a solvent comprising a tetrahydrofuran/water mixture, or equivalent, or dioxane, or equivalent, in a sealed, pressure resistant container, thereby derivatizing the solid support with a boronic ester-oxyethylaminoalkyl group or boronic ester-oxyethylaminobenzyl group; and, (b) mixing the solid support ester-dioxyethylaminoalkyl or -dioxyethylaminobenzyl-derivatized solid support with a boronic acid in an anhydrous solvent, thereby derivatizing the solid support with a boronic ester-ethylaminoalkyl or -ethylaminobenzyl group having the formula

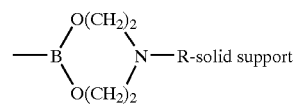

wherein R is an alkyl, substituted alkyl, or benzyl group.

In alternative embodiments, for the processes for making the dihydroxyalkylaminoalkyl-derivatized solid support or the dihydroxyalkylaminobenzyl-derivatized solid supports, the supports can be mixed with the boronic acid in dry tetrahydrofuran. The mixing of step (b) can last from about one to about 60 minutes.

The invention provides a method for making a solid support derivatized with a dihydroxyalkylaminoalkyl of dihydroxyalkylaminobenzyl group comprising mixing an aminoalkylated solid support or aminobenzylated solid support comprising a primary amino group with excess ethylene oxide at about 50° C. in a solvent comprising a tetrahydrofuran/water mixture, or equivalent, or dioxane, or equivalent, in a sealed, pressure resistant container, thereby derivatizing the solid support with a dihydroxyethylamino moiety comprising a tertiary amine having two hydroxyethyl substituents and a formula HO $(CH_2)_2$N $(CH_2)_2$ OH.

The invention provides a method for immobilizing a boronic acid comprising the following steps: (a) providing a solid support derivatized with a dihydroxyalkylaminoalkyl group or a dihydroxyaminobenzyl group, wherein the dihydroxyalkylamino moiety has a formula HO $(CR'_2)_x$ $CH_2N$ $CH_2(CR'_2)_y$ OH, wherein R' is independently selected from the group consisting consisting of H, $C_1$–$C_{20}$ alkyl radical, and $C_1$–$C_{20}$ substituted alkyl radical, and x and y are integers between 1 to about 20, (b) providing a sample comprising at least one boronic acid; and (c) mixing the solid support of step (a) with the sample of step (b) in an anhydrous solvent, thereby immobilizing a boronic acid by generating a boronic ester-dioxyalkylaminoalkyl- or dioxyalkylaminobenzyl-conjugated group having the formula

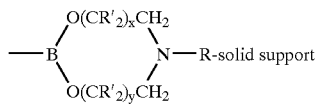

wherein R comprises an alkyl or a benzyl, R' comprises at least one of H and $C_1$–$C_{20}$ radical, and x and y are integers between 1 to about 20. In a preferred embodiment x and y are one.

In other preferred embodiments, the alkyl comprises a substituted alkyl group.

The invention provides a method for purifying a boronic acid comprising the following steps: (a) providing a solid support derivatized wit a dihydroxyalkylaminoalkyl group or a dihydroxyaminobenzyl group, wherein the dihydroxyalkylamino moiety has a formula HO $(CR'_2)_x$ $CH_2N$ $CH_2$ $(CR'_2)_y$ OH, wherein R' is independently selected from the group consisting consisting of H, $C_1$–$C_{20}$ alkyl radical and $C_1$–$C_{20}$ substituted alkyl radical, and x and y are integers between 1 to about 20, (b) providing a sample comprising at least one boronic acid; (c) mixing the solid support of step (a) with the sample of step (b) in an anhydrous solvent, thereby immobilizing a boronic acid by generating a boronic ester-dioxyalkylaminoalkyl- or dioxyalkylaminobenzyl-conjugated group having the formula

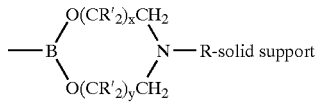

wherein R comprises an alkyl or a benzyl, R' comprises at least one of H and $C_1$–$C_{20}$ radical, and x and y are integers between 1 to about 20; and (d) hydrolyzing the boronic ester linkage, thereby releasing from the support a purified boronic acid. In a preferred embodiment x and y are one.

In one embodiment, the hydrolyzing step is in a solution comprising tetrahydrofuran, water and acetic acid. In one embodiment, the tetrahydrofuran, water and acetic acid ratio is about 90:5:5, respectively. The hydrolyzing step can last about one to about ten minutes. The hydrolyzing step can be in a solution comprising tetrahydrofuran and water. The tetrahydrofuran:water ratio can be about 9:1, respectively. The hydrolysis step can last between about one to about sixty minutes.

In one embodiment, the method further comprises washing the solid support at least once with an anhydrous solvent after the mixing step and before the hydrolysis step. In alternative embodiments, the method is performed in a batch or a column. The method can be performed in an automated or semiautomated synthesizer.

The invention also provides a method for scavenging a boronic acid from a multiple component solution to generate a boronic acid-free solution comprising the following steps: (a) providing a solid support derivatized with a dihydroxyalkylaminoalkyl group or a dihydroxyalkylaminobenzyl group, wherein the dihydroxyalkylamino moiety has a formula HO $(CR'_2)_x$ $CH_2N$ $CH_2(CR'_2)_y$ OH, wherein R' is independently selected from the group consisting consisting of H, $C_1$–$C_{20}$ alkyl radical, and $C_1$–$C_{20}$ substituted alkyl radical, and x and y are integers between 1 to about 20, (b) providing a sample comprising at least one boronic acid; (c) mixing the solid support of step (a) with the sample of step (b), thereby immobilizing a boronic acid by generating a boronic ester-dioxyalkylaminoalkyl- or dioxyalkylaminobenzyl-conjugated group having the formula

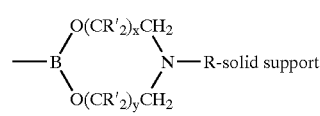

wherein R comprises an alkyl or a benzyl, R' comprises at least one of H and $C_1$–$C_{20}$ radical, and x and y are integers between 1 to about 20; and (d) washing the solid support after the mixing of step (c) to remove non-boronic acid components; thereby scavenging the boronic acid from the multiple component sample to generate a boronic acid-free solution. In a preferred embodiment x and y are one.

In one embodiment, a molar excess of the support (i.e., boronic ester-dioxyalkylaminoalkyl-conjugated groups) compared to an estimated (or theoretical) amount of boronic acid in the multiple component sample is used.

In yet another embodiment, the invention provides novel compositions and methods for resin-to-resin transfer reactions, e.g., Suzuki coupling reactions, via phase transfer of solid supported boronic acids under both aqueous and anhydrous conditions.

In one embodiment, the invention provides a method for the solid phase synthesis of functionalized compounds, such as functionalized biphenyl compounds, comprising the following steps: (a) providing a boronic ester-dioxyalkylaminoalkyl-conjugated solid support or a boronic ester-dioxyalkylaminobenzyl-conjugated solid support, (b) providing a substituted haloarene-conjugated solid support; (c) reacting the conjugated support of step (a) with the conjugated support of step (b) under conditions comprising a catalyst, a base and a solvent, thereby producing a solid supported, functionalized reaction product conjugated to a solid support; and, (d) reacting the reaction product of step (c) with a solvent comprising an acid, such as trifluoroacetic acid, or equivalent, and a non-protic, non-polar solvent, such as methylene chloride, or equivalent, thereby liberating a functionalized compound, such as a biphenyl compound, from the solid support.

In alternative embodiments of the methods of the invention, the solid-supported boronic ester derivative originates from a polyfunctionalized arylboronic acid containing at least one of the following substituents at either ortho-, meta- and/or para-positions: (a) a carboxamide or equivalent; (b) a carboxylic ester or equivalent; (c) a methylamino group or equivalent; (d) an anilide group, or equivalent, comprising an acyl group; (e) a urea, or equivalent, comprising an acylamino group; (f) a sulfonamide, or equivalent, comprising a sulfonyl group; or (g) an aryl alkyl ether or equivalent. The carboxamide or equivalent of step (a) can be made from either a primary or a secondary amine and a corresponding carboxylic acid via coupling methods for amide formation. The carboxilic ester or equivalent of step (b) can be made from an alcohol and a corresponding carboxylate. The amine of the methylamino group of step (c) can be a secondary or a tertiary amine made by reactions of a primary or secondary amine on a corresponding halomethyl substitute. The acyl group of step (d) can be an alkanoyl or a benzoyl group reacted with a corresponding aniline. The acylamino group of step (e) can be derived from an alkanoyl or a benzoyl group of an isocyanate reacted from a corresponding aniline. The sulfonyl group of step (f) can be derived from a sulfonyl chloride reacted onto the corresponding aniline. The alkyl group of step (g) can be derived from a primary or secondary alcohol reacted on the corresponding phenol via a Mitsunobu-like reaction.

In one embodiment, the a solid-supported boronic ester of substituent (a) is an amide derivative of p-carboxybenzeneboronic acid or equivalent. The amide can comprise $NH(CH_2)_3Ph$ or equivalent. The functionalized compound produced in step (d) can be a 4,4'-biphenyl dicarboxylic acid monoamide or equivalent.

In one embodiment, the solid-supported boronic ester of step (a) comprises a benzylamine or equivalent. The functionalized compound produced in step (d) can be a monoalkylated biphenyl dibenzylamine or equivalent. The solid-supported boronic ester of step (a) can comprise a NHCOPh group or equivalent. The functionalized compound produced in step (d) can be a monoacylated biphenyl dianiline or equivalent.

In one embodiment, the molar equivalent ratio of solid supported boronic ester to haloarene-conjugated solid support is about 3 to about 4.

In one embodiment, the solid-supported boronic ester of step (a) is originating from an arylboronic acid or a vinyl boronic acid. The arylboronic acid can be a p-tolueneboronic acid or an equivalent thereof.

In one embodiment, the solid support is a resin, such as a polystyrene resin or an equivalent thereof. The solid support also can be a polystyrene-polyethylene glycol resin or an equivalent thereof. The solid-supported haloarene of step (b) can be a solid-supported polysubstituted halobenzoic acid, a solid-supported amino-substituted haloarene, a solid-supported aminoalkyl-substituted haloarene, or an equivalent thereof. The halobenzoic acid carboxy group can be conjugated to a hydroxymethylphenoxy-polystyrene resin or an equivalent thereof. The halobenzoic acid carboxy group can be conjugated to a hydroxymethylphenoxy-polystyrene-polyethylene glycol resin or an equivalent thereof. The amino group can be attached to a triphenylmethylpolystyrene resin or an equivalent thereof.

In alternative embodiments, the haloarene of step (b) of the method is an iodoarene, a chloroarene, a bromoarene or an equivalent thereof. The iodoarene can be a p-iodobenzoic acid group or an equivalent thereof.

In one embodiment, the conditions of step (c) of the method further comprise use of a Pd(0) catalyst or an equivalent thereof. The Pd(0) catalyst can comprises a $Pd(PPh_3)_4$ or a $Pd_2(dba)_3$.

In one embodiment, the basic solvent of step (c) of the method is an aqueous solvent. The basic solvent of step (c) of the method can comprise a sodium carbonate, a potassium carbonate or an equivalent thereof. The basic solvent of step (c) can comprise a trialkylamine, a potassium fluoride, a sodium fluoride, a cesium fluoride or an equivalent thereof.

In alternative embodiments of the method, wherein the reaction conditions of step (c) comprise a temperature of between about 25° C. to about 120° C.; of between about 50° C. to about 100° C.; and, of between about 80° C. to about 90° C.

In alternative embodiments of the method, the reaction conditions of step (c) comprise a reaction time of between about 1 hours to about 72 hours; of between about 10 hours to about 50 hours; and, of between about 15 hours to about 25 hours.

In alternative embodiments of the method, the aqueous solvent comprises a PhMe/EtOH, a DME/water and a DMF/water solvent. The PhMe/EtOH molar ratio can be about 4:1; about 3:1 or about 2:1. The DME/water and DMF/water molar ratios can be about 12:1; about 9:1; about 6:1; or about 3:1.

In one embodiment, the Pd(0) catalyst comprises a $Pd(PPh_3)_4$ and the solvent is PhMe/EtOH at about a 3:1 molar ratio and the reaction conditions of step (b) comprise a reaction time of about 20 hours and a temperature of about 80° C. to about 110° C.

In one embodiment, the basic solvent of step (c) is an anhydrous basic solvent. The basic solvent can further comprise ethylene glycol or equivalent as a co-solvent. The basic solvent can comprise at least one tertiary amine base. The tertiary amine base can comprise diisopropylethylamine, $Et_3N$ (triethylamine), $N(CH_2CH_2OH)_3$ or an equivalent thereof. The basic solvent can comprise $Et_3N$ (triethylamine) or equivalent and ethylene glycol or equivalent at a molar ratio of about 1:1.

In alternative embodiments, the reaction conditions of step (c) comprise a temperature of between about 25° C. to about 120° C.; of between about 50° C. to about 115° C.; or, of between about 80° C. to about 110° C. The reaction conditions can comprise a reaction time of between about 15 hours to about 25 hours.

In alternative embodiments, the anhydrous solvent comprises a DMF solvent, a PhMe solvent or a dioxane solvent, or an equivalent thereof.

In one embodiment of the method, the reaction conditions of step (c) comprise a Pd(0) catalyst comprising a $Pd_2(dba)_3$, and a solvent comprising DMF and $Et_3N$ (triethylamine) or equivalent and ethylene glycol or equivalent at a molar ratio of about 1:1 at about 105° C. for at least about 20 hours.

In one embodiment, the aminoalkyl moiety is an aminomethyl group.

In yet another embodiment of the invention, there is provided a method for the solid phase synthesis of functionalized compounds comprising the following steps: (a) providing a first reactant comprising a boronic ester-dioxyalkylaminoalkyl- or -dioxyalkylaminobenzyl-conjugated solid support, (b) providing a second reactant conjugated to a solid support; (c) providing a transfer agent; (d) providing a solvent; (e) reacting the boronic ester-dioxyalkylaminoalkyl- or dioxyalkylaminobenzyl-conjugated solid support of step (a) with the second reactant of step (b) and the transfer agent of step (c) in the solvent of step (d), thereby producing a solid supported, functionalized reaction product; and (f) liberating the functionalized compound from the solid support.

In yet another embodiment of the invention, there is provided a method for the solid phase synthesis of functionalized glycine compounds comprising the following steps: (a) providing a boronic ester-dioxyalkylaminoalkyl- or dioxyalkylaminobenzyl conjugated solid support, (b) providing a solid-supported iminium compound; (c) providing a transfer agent; (d) reacting the boronic ester-dioxyalkylaminoalkyl- or dioxyalkylaminobenzyl conjugated solid support of step (a) with the transfer agent of step (c) and the solid-supported iminium of step (b) in a solvent, thereby producing a solid supported, functionalized glycine reaction product; and, (e) liberating the functionalized compound from the solid support.

In yet another embodiment of the invention, there is provided a method for the solid-phase derivatization of a functionalized boronic acid comprising the following steps: (a) providing a dihydroxyalkylaminoalkyl or dihydroxyalkylaminobenzyl-conjugated solid support; (b) providing a sample comprising a functionalized boronic acid; (c) mixing the solid support with the sample in an anhydrous solvent, thereby immobilizing the functionalized boronic acid by generating a functionalized boronic ester-dioxyalkylaminoalkyl- or boronic dioxyalkylaminobenzyl-conjugated group; (d) providing at least one derivatizing agent capable of reacting with the functional group of the functionalized boronic acid; and (e) contacting the derivatizing agent of step (d) with the functionalized boronic ester-dioxyalkylaminoalkyl- or functionalized boronic dioxyalkylaminobenzyl-conjugated group in a solvent, thereby producing a solid supported, derivatized boronic acid product.

In one embodiment, the reaction takes place in a device, such as a synthesizer, such as a semiautomated synthesizer, e.g., a parallel synthesizer.

The invention also provides a device, such as a "synthesizer," comprising (a) a boronic ester-dioxyalkylaminoalkyl-conjugated solid support or a boronic ester-dioxyalkylaminobenzyl-conjugated solid support, and, (b) a haloarene-conjugated solid support. The synthesizer can be a semiautomated synthesizer, such as a parallel semiautomated synthesizer, or a fully automated synthesizer.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
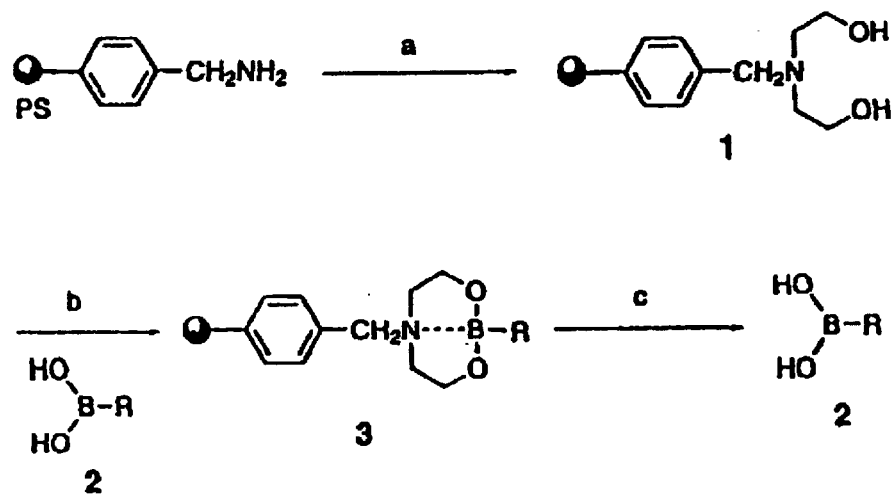
FIG. 1 is a schematic summarizing the synthesis of DEAM-PS resin, and the immobilization of a boronic acid as discussed in detail in Example 1, below.

The invention provides solid supports for the immobilization of boronic acids, particularly, functionalized boronic acids, such as aryl boronic acids. As noted above, the compositions and methods of the invention are particularly useful in solid-phase syntheses, such as those used in combinatorial chemistries.

The invention provides solid supports derivatized with dihydroxyalkylaminoalkyl and dihydroxyalkylaminobenzyl groups. For example, in one embodiment, the solid support derivatized with a dihydroxyalkylaminoalkyl group is an N,N-diethanolaminomethyl. In another embodiment, the solid support is derivatized with a dihydroxy-alkylaminobenzyl group. The solid supports can be of any material that can be derivatized with or coupled to dihydroxyalkylaminoalkyl groups. For example, in one embodiment, the solid support is a polystyrene, e.g., a dihydroxyalkylaminoalkyl-conjugated resin, such as diethanolamine derivatized polystyrene ("DEAM-PS"). The solid support can be in any form, e.g., as a bead, a filament, a porous material, and the like.

The invention also provides novel methods for making and using the solid supports of the invention. Solid supports of the invention, e.g., DEAM-PS, can be employed to efficiently immobilize and transform functionalized boronic acids (e.g., arylboronic acids, vinyl boronic acids, and the like). Solid supports of the invention can be used to immobilize boronic acids for use in any reaction involving boronic acids or derivatives thereof, such as for amide coupling, acylation or reductive amination methods. Solid supports of the invention can be used to "scavenge" or "fish out" a boronic acid from a sample, particularly a sample comprising a complex mixture of chemicals. "Scavenging" is a reaction in solution-phase with a molar excess of a boronic acid as reagent (e.g., a solid support of the invention comprising a dihydroxyalkylaminoalkyl group), as compared to the amount of boronic acid in the sample. The reaction generates a boronic acid-free solution.

In alternative embodiments, solid supports of the invention also facilitate the synthesis of new functionalized boronic acids, such as new arylboronic acids, vinyl boronic acids, alkyl boronic acids, and the like. Solid supports of the invention can be used in the large-scale synthesis and/or purification of boronic acids, e.g., arylboronic acids. Solid supports of the invention are useful in resin to resin transfer reactions, such as in Suzuki cross-coupling reactions. The resultant biphenyl products can be used to produce a variety of chemicals and products, e.g., pharmaceutical reagents.

The dihydroxyalkylaminoalkyl- and dihydroxyalkylaminobenzyl-derivatized solid supports of the invention are particularly useful in combinatorial chemistries and various devices (automated and semiautomated) used in such solid-phase chemistries.

The compositions of the invention are also useful for stabilizing boronic acids from oxidation by air. Accordingly, the compositions of the invention can be used to store boronic acids, particularly, those sensitive to oxidation. For example, use of a resin-to-resin transfer reactions (RRTR) strategy using the derivatized solid supports of the invention (e.g., DEAM-PS resin) is advantageous for handling and storage of boronic acids; otherwise air-sensitive boronic acids (e.g., alkenylboronic acid) are stabilized through immobilization as diethanolamine adducts.

In one embodiment, as described in Example 1, below, polystyrene resin was derivatized with a diethanolamine anchor. This was achieved through the reaction of 1% divinylbenzene cross-linked aminomethylated polystyrene (AM-PS) with excess ethylene oxide at 50° C. in a tetrahydrofuran (THF)/water solvent mixture using a sealed, pressure-resistant tube (see FIG. 1). Under these conditions, quaternization to give the triethanolalkylammonium hydroxide salt and oxirane alcoholysis are known to be minimal (see, e.g., Sundaram (1969) Bull. Chem. Soc. Jpn. 42:3141–3147). The resulting diethanolamine-derivatized resin possessed characteristics and a loading level that demonstrated the clean and complete bis-alkylation of amino-methylated polystyrene (AM-PS) to give DEAM-PS. In another embodiment, polystyrene resin was derivatized with a diisobutanolamine anchor using isobutylene oxide (see Example 6). In other preferred embodiments, other oxiranes, e.g., styrene oxide, substituted styrene oxide, aryl substituted oxiranes, can be used to form the corresponding dihydroxyalkylamine-derivatized resin.

The invention also provides novel strategies for resin-to-resin transfer reactions, via phase transfer of solid supported boronic acids under both aqueous and anhydrous conditions. Resin-to-resin transfer reactions represent an advance in solid-phase synthesis. In addition to further simplifying solid-phase synthesis, they allow the use of convergent strategies and their associated advantages. The invention's novel RRTR process can be applied to the synthesis of many classes of compounds, e.g., biologically relevant biphenyl and arylglycine compounds. Biphenyl and arylglycine compounds are commonly used as, or the synthesis of, therapeutic agents, and in the generation of combinatorial libraries.

For example, the methods of the invention provide convergent solid-phase synthesis of symmetrically or unsymmetrically functionalized compounds, such as biphenyl compounds. Biphenyl units, whether symmetrical or not, are popular pharmacophores in drug discovery. Also, other advantages of RRTR over the traditional approaches also relate to the advantages of using dihydroxyalkylamino-derivatized resins, e.g., it is not necessary to cleave and handle the boronic acid in solution and saves time. Also, it allows the use of convergent synthetic strategies which can potentially allow access to compounds that are inaccessible otherwise.

Examples 2 and 3, below, describes preferred embodiments of uses of the present invention for resin-to-resin transfer reactions (RRTR). As described in Example 3, below, the invention provides the first resin-to-resin transfer reaction for the formation of carbon-carbon bonds via Suzuki cross-coupling reactions between resin-bound aryl iodides and arylboronic acids supported onto N,N-diethanolaminomethyl polystyrene (DEAM-PS). These solid supports facilitate the synthesis of functionalized arylboronic acids which can otherwise be difficult to handle in solution. As described in detail in FIG. 8, below, p-carboxy-, p-(bromomethyl)-, and m-aminobenzeneboronic acids were bound to N,N-diethanolaminomethyl polystyrene (DEAM-PS) and transformed on solid supports using amide formation, alkylation by a secondary amine, and acylation, respectively. Under conditions for Suzuki coupling, the new resin-bound boronic acids were transferred to solution phase by transesterification and coupled in situ with a haloarene resin. Using the methods of the invention, there is no need for cleaving and therefore handling boronic acids derivatized on the solid support prior to the Suzuki coupling.

The potential of the invention was demonstrated with a convergent solid-phase synthesis of unsymmetrically functionalized biphenyl compounds (see FIG. 9) that would be difficult to access using a linear solid-phase synthesis. The invention's novel resin-to-resin transfer system for carbon-carbon bond formation simplifies solid-phase Suzuki couplings considerably and is very valuable for use in high-throughput combinatorial library synthesis.

Another preferred embodiment is the optimization of a resin-to-resin borono-Mannich reaction between secondary amines and arylboronic acids to make arylglycine derivatives described in Example 2. Compounds of this nature are of particular interest for their biological activity (see, e.g., Bedingfield (1995) J. Pharmacol. 116:3323–3330). Iminium intermediates, formed from the condensation of glyoxylic acid and resins functionalized with a secondary amine, were coupled to resin-derivatized boronic acids. The iminium intermediates were then transferred to solution from the corresponding N,N-diethanolaminomethyl-polystyryl boronates by in situ transesterification with the ethanol co-solvent to provide arylglycine derivatives.

Any reaction involving a boronic acid is adaptable to the methods of the invention, including, e.g., Chan (1998) Tetrahedron Lett. 39:2933–2936; Petasis (1998) J. Am. Chem. Soc. 120:11798–11799.

The invention also provides synthesizer devices, e.g., synthesizers, such as parallel synthesizers, comprising solid supports derivatized with haloarenes and various boronic acids.

Definitions

Unless defined otherwise, all technical and scientific terms used herein have the meaning commonly understood by a person skilled in the art to which this invention belongs. As used herein, the following terms have the meanings ascribed to them unless specified otherwise.

As used herein, the term "alkyl" is used to refer to a branched or unbranched, saturated or unsaturated, open chain or cyclic, hydrocarbon radical having from 1 to about 20 carbons, or, from about 4 to about 20 carbons, or, from about 6 to about 18 carbons. When the alkyl group has from 1 to about 6 carbon atoms, it can be referred to as a "lower alkyl." Suitable alkyl radicals include, for example, structures containing one or more methylene, methine and/or methyne groups. The term also includes branched structures have a branching motif similar to i-propyl, t-butyl, i-butyl, 2-ethylpropyl, etc. As used herein the term encompasses "substituted alkyls." "Substituted alkyl" refers to an alkyl as just described including one or more functional groups such as lower alkyl, aryl, acyl, halogen (i.e., alkylhalos), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon of the alkyl moiety. Additionally, these groups may be pendent from, or integral to, the alkyl chain.

As used herein, the term "arene" refers to any substituted or unsubstituted mono- or polycyclic aromatic hydrocarbon compound as well as any mono- or polycylic heteroaromatic compounds, and can include fused or bridged ring systems.

The term "boronic acid" includes any form of boronic acid or equivalent, including, e.g., aryl boronic acids, such as such as phenylboronic acids; see also, U.S. Pat. Nos. 6,083,903; 6,075,126; 6,037,490; 6,031,117; 6,013,783; 5,840,677; 5,780,454; 5,739,318. Boronic acid reagents and boronic acid complexing reagents are described in, e.g., U.S. Pat. Nos. 5,594,111, 5,623,055, 5,668,258, 5,648,470, 5,594,151, 5,668,257, 5,677,431, 5,688,928, 5,744,627, 5,777,148, 5,831,045 and 5,831,046.

As used herein, the term "Mitsunobu-like reaction" means any reaction based on a Mitsunobu reaction (the nucleophilic substitution of an alcoholic hydroxyl group mediated by the redox system trialkylphosphine/dialkyl azodicarobxylate), which is well known in the art, see, e.g., Barrett (2000) Org. Lett. 2:2999–3001; Stachel (2000) Org. Lett. 2:1637–1639; Falkiewicz (1999) Nucleic Acids Symp. Ser. 42:9–10; Wisniewski (1998) J. Pept. Sci. 4:1–14.

As used herein, the term "transfer agent" or "chaperone" refers to any neutral chemical agent. In RRTR, transfer of one resin-bound substrate to solution phase is necessary in order to effect its coupling to other resin-bound substrates. A neutral chemical agent, or chaperone, is required to promote this event under conditions compatible with the desired reaction.

As used herein, the term "resin" refers to any insoluble polymeric material which allows ready separation from liquid phase materials by filtration and which can be used to carry library members or reagents, or to trap excess reagents or reaction by-products (i.e. scavenger resin).

As used herein the term "solid support" refers to insoluble, functionalized, polymeric material to which library members or reagents may be attached (often via a linker) allowing them to be readily separated (e.g. by filtration, centrifugation, etc.) from excess reagents, soluble reaction by-products or solvents.

The terms "dioxyalkylaminoalkyl" and "bis(oxyalkyl)aminoalkyl" described the same structure, as schematically shown, above.

As used herein, the terms "mixing" or "contacting" refer to the act of bringing components of a reaction into adequate proximity such that the reaction can occur. More particularly, as used herein, the terms "mixing" and "contacting" can be used interchangeably with the following: combined with, added to, mixed with, passed over, flowed over, etc.

General Methods

Figure 24:
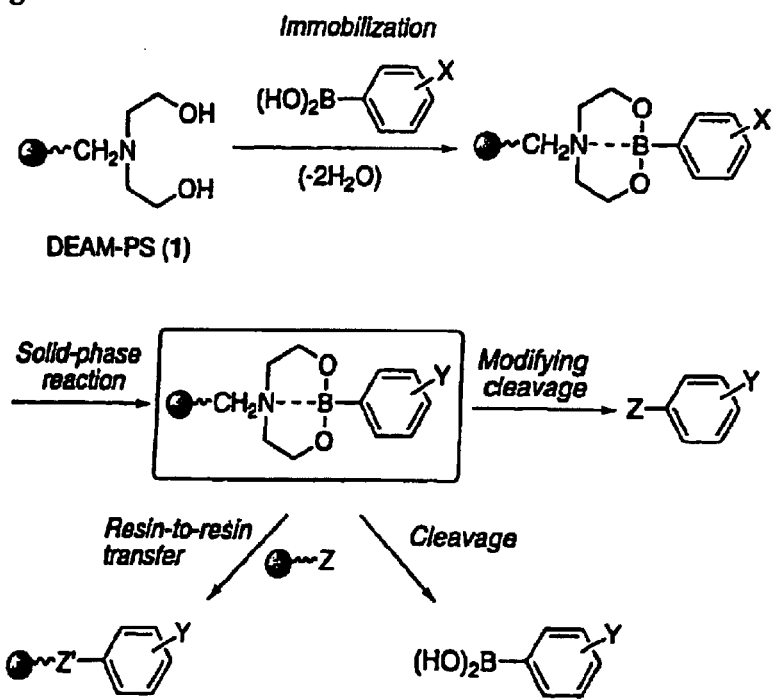
FIG. 24 is a schematic of the immobilization and derivatization of functionalized boronic acids using N,N-diethanolaminomethyl polystyrene (DEAM-PS).

The present invention provides novel solid supports derivatized with a dihydroxyalkylaminoalkyl (e.g., a diethanolaminoalkyl) or dihydroxyalkylaminobenzyl group. The invention also provides novel means of making and using these solid supports, including the resin-to-resin transfer reactions via phase transfer of soid supported boronic acids under both aqueous and anhydrous conditions. FIG. 24 is a schematic of the immobilization and derivatization of functionalized boronic acids using N,N-diethanolaminomethyl polystyrene (DEAM-PS).

The skilled artisan will recognize that the methods of the invention can be practiced using a variety of ancillary and equivalent procedures and methodologies, which are well described in the scientific and patent literature., e.g., Organic Syntheses Collective Volumes, Gilman et al. (Eds) John Wiley & Sons, Inc., NY; Venuti (1989) Pharm Res. 6:867–873. The invention can be practiced in conjunction with any method or protocol known in the art, which are well described in the scientific and patent literature. Therefore, only a few general techniques will be described prior to discussing specific methodologies and examples relative to the novel methods of the invention.

Solid Support Surfaces

The solid supports can be of any material that can be used in solid phase synthesis and that can be coupled to (or "derivatized with"), directly or indirectly, covalently or non-covalently, a dihydroxyalkylaminoalkyl group, or a dihydroxyalkylaminobenzyl group, or mixtures thereof. Any solid or semisolid surface that can be derivatized with a dihydroxyalkylaminoalkyl (e.g., a diethanolaminoalkyl) group or a dihydroxyalkylaminobenzyl group can be used to practice the invention. In one embodiment, the invention uses an aminoalkylated solid support. Any solid support with can be directly or indirectly aminoalkyl-derivatized can be used.

The solid support need only be substantially insoluble under conditions for practicing the methods of the invention. The solid support can be of a rigid, semi-rigid or flexible material. The solid support can be flat or planar, be shaped as wells, raised regions, etched trenches, pores, beads, filaments, or the like.

Any solid support upon which a dihydroxyalkylaminoalkyl (e.g., a diethanolaminoalkyl) or a dihydroxyalkylaminobenzyl group can be bound can be used to practice the invention. For example solid supports can be of any material, or mixture of material, upon which an alkyl halide or a substituted alkyl halide, or at aminoalkyl group, can be directly or indirectly bound. For example, suitable materials can include, e.g., resins, such as polystyrenes or equivalent compositions (see, e.g., U.S. Pat. No. 5,290,819; 5,525,637; 5,591,778; 5,880,166; 5,900,146). The polystyrene can comprise a poly(styrene-divinylbenzene) (PS-DVB) or an equivalent composition. The solid support can comprise a plastic or a plastic copolymer (Nylon™, Teflon™) or an equivalent thereof. The solid support can comprise a polyphenol, a polyvinyl, a polypropylene, a polyester, a polyethylene, a polyethylene glycol, a polystyrene-copolymer, or an equivalent thereof, or a mixture thereof. For example, an equivalent of glycol is a polyethylene glycol copolymer, e.g., Tentagel R™ (various TentaGel resins are sold by Rapp Polymere GmbH, Tübingen, Germany). The solid support can comprise a poly(vinyl alcohol) (PVA) hydrogel. The solid support can comprise a polyacrylamide or an equivalent polymer composition. The polyacrylamide can comprise a polymethacylamide, a methyl methacrylate, a glycidyl methacrylate, a dialkylaminoalkyl(meth)acrylate, or a N,N-dialkylaminoalkyl(meth)acrylate, or an equivalent composition. The solid support can comprise an inorganic composition selected from the group consisting of sand, silica (e.g., silica porous microbeads, see, e.g., U.S. Pat. Nos. 5,128,114, 5,032,266, or silica gels, see, e.g., U.S. Pat. No. 6,071,838, such as a silica hydrogel, see, e.g., U.S. Pat. No. 6,074,983), glass (see, e.g., U.S. Pat. No. 5,843,767; 5,604,163), glass fibers (see, e.g., U.S. Pat. No. 6,053,012), quartz glass (see, e.g., U.S. Pat. No. 6,071,838), metals (e.g., gold, alumina (see, e.g., U.S. Pat. No. 6,048,577), zirconia, titania, and nickel oxide). Other solid support alternatives include ceramics, quart (see quartz glass, above) or other crystalline substrates (e.g. gallium arsenide), metalloids, polacryloylmorpholide, poly(4-methylbutene), poly(ethylene terephthalate), rayon (see, e.g., U.S. Pat. No. 5,609,957), nylon, poly(vinyl butyrate), polyvinylidene difluoride (PVDF) (see, e.g., U.S. Pat. No. 6,024,872), silicones (see, e.g., U.S. Pat. No. 6,096,817), polyformaldehyde (see, e.g., U.S. Pat. Nos. 4,355,153; 4,652,613), cellulose (see, e.g., U.S. Pat. No. 6,103,885), cellulose acetate (see, e.g., U.S. Pat. No. 5,929,229), nitrocellulose, various membranes and gels (e.g., silica aerogels, see, e.g., U.S. Pat. No. 5,795,557), paramagnetic or superparamagnetic microparticles (see, e.g., U.S. Pat. No. 5,939,261) and the like. The surface can be derivatized for application of the alkyl halide or a substituted alkyl halide or equivalents. Reactive functional groups can be, e.g., hydroxyl, carboxyl, amino groups or the like.

In one preferred embodiment, the polystyrene has a low degree of divinylbenzene cross-linking. In solid-phase chemistry, both for immobilization and derivatization purposes, about 1%–2% cross-linking is preferred in one embodiment to optimize resin swelling and reagent diffusion. Higher degrees of cross-linking found in macroreticular resins (8%–20%) generally provide materials of much lower efficiency for use in solid-phase chemistries. It has been shown that the degree of cross-linking is important to solid-phase applications, and higher degrees of cross-linking have been shown to be unsuitable for solid-phase reactions (see Rana et al., *J. Comb. Chem.* 2001, 3, 9–15).

In one embodiment, the solid support is a plurality of conjugated beads or bundles of conjugated fibers, e.g., a column of conjugated resin beads.

Synthesizers

The invention also provides synthesizers, such as semi-automated or fully automated synthesizers, e.g., parallel synthesizers, comprising solid supports derivatized with haloarenes and various boronic acids. A variety of semi-automated and automated synthesizers are available for chemical synthesis, particularly for use in combinatorial chemistries. For example, the Trident™ library synthesizer of Argonaut Technologies, San Carlos, Calif.; synthesizers of ArQule of Medford, Mass.; Accelab Laboratory Automation or RAPP Polymere GmbH, of Tuebingen, Germany; and the like. See also Bhattacharyya (2000) Comb. Chem. High Throughput Screen. 3:117–124; South (2000) Comb. Chem. High Throughput Screen. 3:139–151; South (2000) Biotechnol. Bioeng. 7:51–57; Davis (2000) Biotechnol. Bioeng. 71:19–27). Other devices that are suited for, are can be adapted to be suited for, making and using the instant invention are described in, e.g., U.S. Pat. Nos. 6,086,740; 6,025,371.

Combinatorial Chemistries

The dihydroxyalkylaminoalkyl- and dihydroxyalkylaminobenzyl-derivatized solid supports are particularly useful in combinatorial chemistries. For example, the solid supports of the invention can be used to immobilize boronic acids, e.g., aryl boronic acids. The solid supports of the invention can be used to immobilize aryl, alkenyl, and alkyl boronic acids near quantitatively in a wide range of organic solvents.

The invention's novel methods, including its strategies for resin-to-resin Suzuki coupling reactions and borono-Mannich reactions via phase transfer of solid supported boronic acids under both aqueous and anhydrous conditions, are particularly useful in combinatorial chemistries. For example, the methods of the invention, incorporating a Suzuki RRTR system, allow for the convergent solid-phase synthesis of symmetrically or unsymmetrically functionalized compounds, including symmetrically or unsymmetrically functionalized biphenyl compounds.

Methods, reagents and apparatus for practicing combinatorial chemistries are well known in the art, see, e.g., U.S. Pat. Nos. 6,096,496; 6,075,166; 6,054,047; 5,980,839; 5,917,185; 5,767,238.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Preparation and Use of N,N-diethanolaminomethyl Polystyrene

The following example describes an exemplary protocol for practicing the methods of the invention to prepare and use a stable, resin-bound boronic ester in the form of an N,N-diethanolaminomethyl polystyrene (DEAM-PS).

Preparation of DEAM-PS resin. Referring now to FIG. 1, reaction a, polystyrene resin was derivatized with a diethanolamine anchor through the reaction of aminomethylated polystyrene (AM-PS) with excess ethylene oxide at 50° C. in a tetrahydrofuran (THF)/water solvent mixture using a sealed, pressure-resistant tube.

1% Divinylbenzene (DVB) cross-linked aminomethylated polystyrene (3.0 g, 1.00 mmol g$^{-1}$ substitution) was weighed out in a large thick-walled pressure tube equipped with a stirring bar. A 9:1 THF/water mixture (25 mL) was added; followed by excess ethylene oxide (approximately 2 mL). The tube was quickly closed through its Teflon™ screw cap equipped with a seal and immersed into a 50 to 55° C. oil bath. The tube was hand shaken periodically when magnetic stirring becomes inefficient. After about 12 to 24 hours, the tube was allowed to cool to RT and uncapped. The tube contents were passed through a medium-porosity fritted glass filter and the resin was rinsed with THF (5×), CH$_2$Cl$_2$/Et$_3$N 3:1 (3×), then CH$_2$Cl$_2$ (5×), and dried under high vacuum for a few days (the resin was pulverized to powder after a few hours of drying), affording 3.35 g of a white colored resin (theoretical: 3.26 g, 0.92 mmol g$^{-1}$).

The resulting diethanolamine-derivatized resin possessed characteristics and a loading level that demonstrated the clean and complete bis-alkylation of aminomethylated polystyrene (AM-PS) to give DEAM-PS. The resulting resin gave a negative outcome on Kaiser's ninhydrin assay (see, e.g., Kaiser (1970) Anal. Biochem. 34:595–598), indicating the absence of any primary and secondary amines originating from incomplete alkylation. The presence of a basic tertiary amine site, however, is shown through a positive reaction with bromophenol blue. The absence of overalkylation to give a triethanolalkylammonium hydroxide resin was indirectly confirmed by exhaustive acylation with FmocGlyOH (HOBT, DIC, DMAP; DMF, RT, 6 h) followed by UV quantitation of the resulting fulvene-piperidine adduct. The loading level obtained therein was in agreement with the formation of two ethanolamine arms per aminomethyl site according to the initial loading of commercial AM-PS.

A slightly high O/N ratio from combustion analysis of the resin (theoretical=2.3, experimental=2.6) was found in one embodiment, possibly indicating the presence of residual water, or of a few hydroxyethoxyethyl arms (HOCH$_2$CH$_2$OCH$_2$CH$_2$N—) formed by ethylene oxide solvolysis in one embodiment. These trace inhomogeneities did not affect the resin's efficiency.

Immobilization and subsequent release of boronic acids from DEAM-PS resin. Referring now to FIG. 1, reactions b and c, a schematic of a typical immobilization and subsequent release of a boronic acid is shown. In one preferred embodiment of reaction "b" conditions comprised a boronic acid (compound 2), solvent, RT, 15 min. In other embodiments, boronic acid b comprised any of the boronic acids of FIG. 2 and Table 1. In one preferred embodiment of reaction "c", conditions comprised THF/H$_2$O/AcOH 90:5:5, RT, 1 h; or THF/H$_2$O 9:1, RT, 2 h.

Preliminary experiments showed that DEAM-PS resin could couple almost quantitatively to equimolar amounts of arylboronic acids in dry THF or other suitable solvents after a few minutes. The formation of a stable resin-bound boronic ester adduct (compound 3) was highly favored; there was no need to remove the produced water, unlike with other types of diols, whether solid-supported or not, which usually require azeotropic removal of water. The use of a glycerol-PS resin (purchased from Advanced Chemicals, Inc.) led to less than 50% coupling under the same conditions (data not shown). These results clearly underlined the benefit of nitrogen coordination allowed by dihydroxyalkylamine-conjugated resins, such as DEAM-PS. Another control experiment ruled out the possibility that a tertiary amine site alone could be sufficient by forming a tight acid-base complex. Diisopropylaminomethyl polystyrene (Argonaut Technologies, San Carlos, Calif.) failed to couple with compound 2a (see FIG. 2) under usual conditions (data not shown).

Immobilization and solid-phase transformations of resin-bound arylboronic acid compounds, and synthesis of new boronic aacid derivatives compounds using DEAM-PS resin. Of particular interest to combinatorial chemistry was the use of solid supports and methods of the invention to immobilize functionalized boronic acid templates and plan different solid-phase transformations. For example, this would allow the elaboration of diverse libraries of new arylboronic acids with potential use as inhibitors of serine protease enzymes (for example, benzeneboronic acid is an effective competitive inhibitor of α-chymotrypsin and subtilisin; see, e.g., Philipp (1971) Proc. Nat. Acad. Sci. USA 68:478–480). In addition, whereas boronic acids are important building blocks for solid-phase Suzuki reactions in combinatorial chemistry (see, e.g., Wendeborn (1998) Synlett pg 671–675), few are commercially available.

Figure 3:
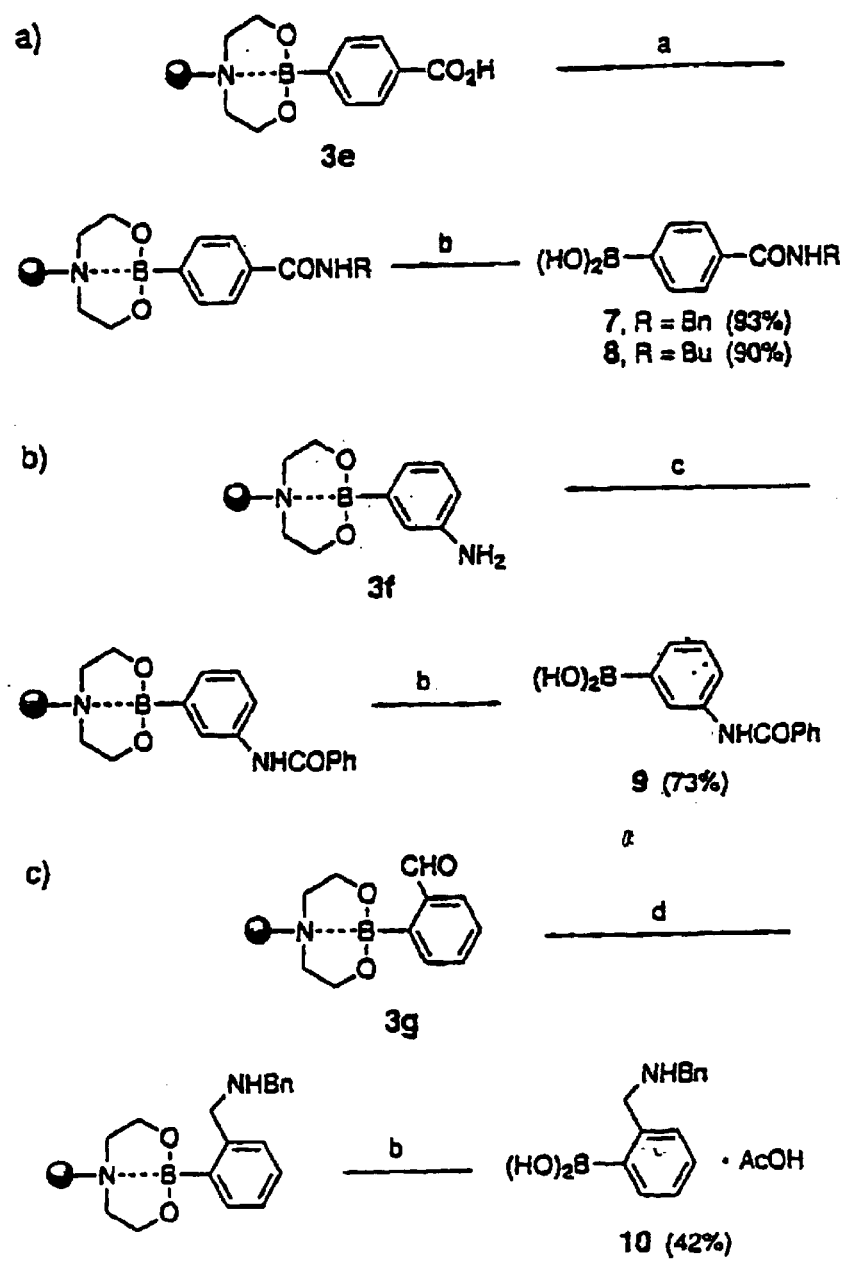
FIG. 3 is a schematic summarizing the immobilization and solid-phase transformations of resin-bound arylboronic acids, as discussed in detail in Example 1, below.

Referring now to FIG. 3, the immobilization and solid-phase transformations of the resin-bound arylboronic acids compound 3e, compound 3f, and compound 3g, and synthesis of new boronic acid derivatives compounds 7 through compound 10 are described. In one preferred embodiment, reaction "a" represents RNH$_2$ (2.5 equiv), N-hydroxybenzotriazole.H$_2$O (2.5 equiv), N,N'-diisopropylcarbodiimide (2.5 equiv), DMF, rt, 6 h; reaction "b" represents THF/H$_2$O/AcOH 90:5:5, RT, 1 h; "reaction c" represents PhCOCl (10 equiv), i-Pr$_2$EtN (11 equiv), THF, rt, 24 h; "reaction d" represents PhCH$_2$NH$_2$ (2.0 equiv), NaBH(OAc)$_3$ (2 equiv), (ClCH$_2$)$_2$, rt, 2 h.

The DEAM-PS boronate linkage was found resistant to standard carbodiimide methods for amide bond formation. Benzylamine and butylamine were coupled with high efficiency to resin-bound p-carboxyphenylboronic acid (compound 3e), affording the corresponding amides compound 7 and compound 8 in high yields after cleavage (non-optimized yields of crude isolated compounds of satisfying purity, all characterized by NMR and MS).

Similarly, resin-bound m-aminophenylboronic acid (compound 3f) was transformed into anilide 9 upon treatment with benzoyl chloride (reaction b) and reductive amination of compound 3g (FIG. 3) with benzylamine afforded compound 10 ((FIG. 3, reaction "c") (non-optimized yields of crude isolated compounds of satisfying purity, all characterized by NMR and MS).

Typical protocol of one embodiment of the invention for the immobilization of compound 3e, followed by amide coupling with butylamine and cleavage to give compound 8: Referring now to FIG. 3, a slight excess of p-carboxyphenylboronic acid (45 mg, 0.27 mmol) was added to a polypropylene filter vessel containing a suspension of resin 1 as depicted in FIG. 1 (200 mg, 0.18 mmol) in dry THF (2 mL). The vessel was shaken for 2 hours after which the resin was rinsed with dry THF (5×) and dry dimethylformamide (DMF) (2×). Unbound boronic acid (a quantity of 13 mg of unreacted boronic acid) was recovered from the first three THF rinses, corresponding almost exactly to the theoretical unbound excess. Dry DMF (2 mL)

was then added to resin 3e and a DMF solution (1 mL) containing N-hydroxybenzotriazole (70 mg, 0.46 mmol) and butylamine (50 μL, 0.46 mmol) was added to the suspension. The latter was homogenized by gentle vortexing followed by the addition of diisopropyl-carbodiimide (72 μL, 0.46 mmol). The vessel was shaken for 5 hours then rinsed with dry DMF (3×) and dry THF (5×). The resulting resin was treated with a 90:5:5 THF/water/acetic acid mixture (2 mL) for 1 hour. The liquid phase was drained and the resin rinsed with the above cleavage mixture (1×) and THF (3×). The combined filtrates were concentrated and dried under high vacuum (>12 hours) to afford arylboronic acid 8 as a white powder (41 mg, 90%). $^1$H NMR (300 MHz, 5% $D_2O$/$CD_3OD$, 25° C.): δ=7.7–8.0 (m, 4H; Ar), 3.37 (t, $^3$J(H,H)=7 Hz, 2H; $NCH_2$), 1.59 (m, 2H; $CH_2CH_2CH_3$), 1.40 (m, 2H; $CH_2CH_3$), 0.96 (t, $^3$J(H,H)=7 Hz, 3H; $CH_3$); $^{13}$C NMR (75 MHz, 5% $D_2O$/$CD_3OD$, 25° C.): δ=170.4 (CONH), 134.9 and 134.8 and 129.6 and 127.1 (4s, Ar), 40.7 ($NCH_2$), 32.6 ($CH_2CH_2CH_3$), 21.1 ($CH_2CH_3$), 14.1 ($CH_3$); MS (+ES): m/z (%): 244 (45) [$M^+$+Na], 222 (100) [$M^+$]; HRMS (+ES): m/z calculated for $C_{11}H_{17}NO_3B$ [$M^+$]: 222.1303. found 222.1301.

Example of the use of DEAM-PS resin for scavenging/capturing boronic acids with THF/water/acetic acid cleavage. The boronic ester linkage of the DEAM-PS boronate ester can be quickly hydrolyzed using a 90:5:5 THF/water/acetic acid cleavage cocktail to release free boronic acids such as those in FIG. 2. For acid-sensitive boronic acids, the resin can also be cleaved under neutral conditions with prolonged exposure to 9:1 THF/water.

Figure 2:
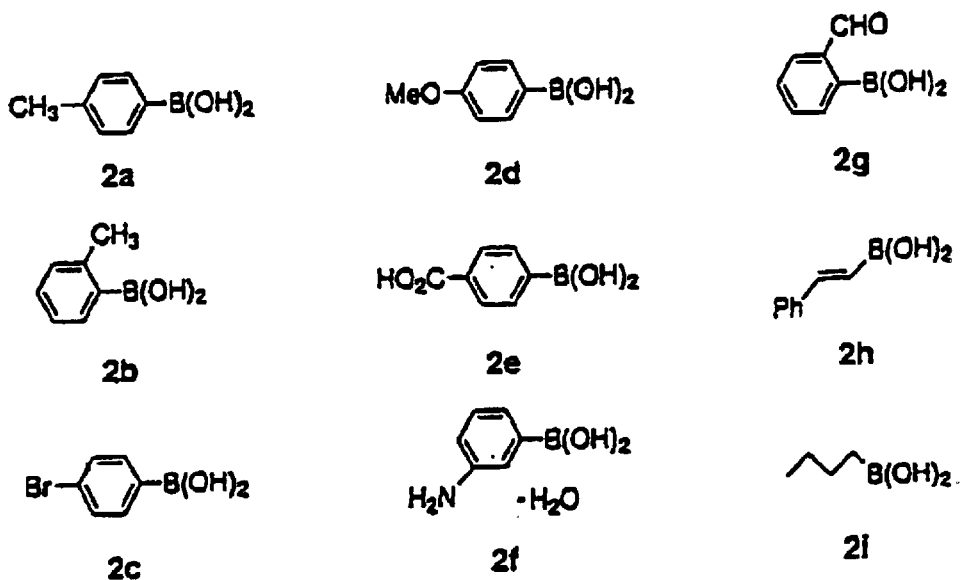
FIG. 2 is a schematic summarizing the structure of boronic acid compounds, as set forth in Table 1, and discussed in detail in Example 1, below.

Referring now to Table 1 and FIG. 2, a solvent profile study using p-tolylboronic acid (compound 2a, FIG. 2) as a model compound and a slight excess of DEAM-PS resin showed that a broad range of organic solvents is suitable for scavenging/immobilizing applications (see entries 1–6).

TABLE 1

Coupling of different boronic acids (2) with DEAM-PS resin 1.[a]

| Entry | Boronic Acid | Solvent | Yield [%][b] | Purity [%][c] |
|---|---|---|---|---|
| 1 | 2a | $CH_2Cl_2$ | >95 | >95 |
| 2 | 2a | DMF | 87 | >95 |
| 3 | 2a | Toluene | >95 | >95 |
| 4 | 2a | $CH_3OH$ | 53 | >95 |
| 5 | 2a | $Et_2O$ | 90 | >95 |
| 6 | 2a | THF | >95 | >95 |
| 7 | 2b | THF | >95 | >95 |
| 8 | 2c | THF | >95 | >95 |
| 9 | 2d | THF | >95 | >95 |
| 10 | 2e | THF | >95 | >95 |
| 11 | 2f | THF | >95 | >90 |
| 12 | 2g | THF | 90 | >95 |
| 13 | 2h | THF | 91 | >90 |
| 14 | 2i | THF | 50 | >90 |

[a]Coupling reactions were conducted by shaking a slight excess of resin 1 (200 mg, 0.92 mmol/g substitution) with the boronic acid (0.8 equiv.) in the indicated solvent (2 mL) at room temperature for 15 min in a polypropylene vessel equipped with a fritted filter.
[b]Based on the amount of boronic acid recovered after cleavage of the resin for 1 h in a 90:5:5 THF/$H_2O$/AcOH mixture. Similar results were observed using a,water/THF 5:95 mixture. A slight imprecision must be ascribed to these values as a result of exhaustive drying that may lead to partial dehydration to give boronic acid anhydrides.
[c]Estimated through $^1$H NMR analysis of the recovered boronic acids compared to commercial starting material.

All boronic acids used in Table 1 were obtained from commercial sources except compound 2h, which was synthesized according to Brown (1972) J. Am. Chem. Soc. 4:4370–4371.

The DEAM-PS resin was also found to be very efficient for immobilizing a wide variety of electron-rich and electron-poor arylboronic acids in near quantitative yields in THF (Table 1, entries 6–12). These values were determined from the amounts of boronic acids recovered after subsequent hydrolytic release from the support. Concentration of the filtrate from exhaustive rising of the resin after immobilization revealed none or very little unbound (unreacted) boronic acid. DEAM-PS resin also coupled efficiently with alkenylboronic acids (entry 13) and with air-sensitive alkylboronic acids (entry 14). The boronic acids 2a–2i of FIG. 2 were recovered intact after cleavage from the solid support.

The DEAM-PS resin was recycled with no apparent loss of efficiency after neutralization with base washings (e.g., 3:1 $CH_2Cl_2$/$Et_3N$).

Figure 13:
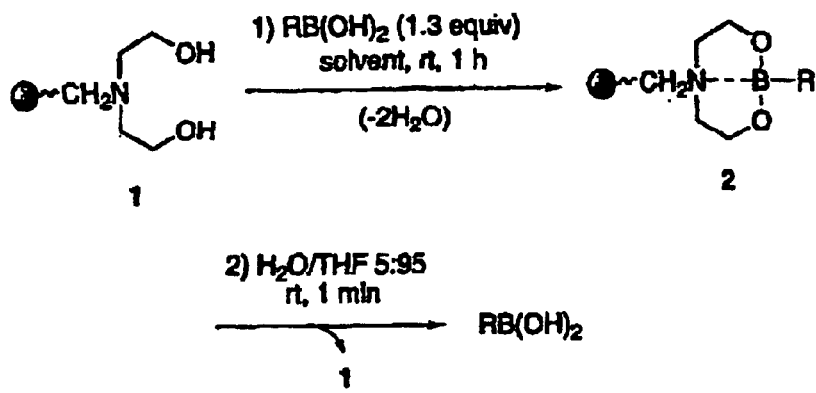
FIG. 13 is a schematic summarizing DEAM-PS resin immobilization and cleavage.

Use of DEAM-PS resin as a resin for scavenging/capturing boronic acids with THF/water/cleavage. Referring now to Table 5 and FIG. 13, a series of boronic acids similar to those of Table 1 presenting different steric and electronic characteristics were tested by shaking with DEAM-PS at room temperature for 1 hour, followed by cleavage with 5% $H_2O$/THF.

A slight excess of the boronic acid (ca. 1.3 equiv), pre-dried in vacuo as the monoanhydride form, was shaken with DEAM-PS at room temperature for 1 hour. Percentages of recovery were based on the amount of boronic acid isolated after cleavage of 2 with water/THF (5:95). A solvent profile study using p-tolylboronic acid revealed that a wide range of anhydrous solvents could be employed (entries 1–6). In a preferred embodiment, THF was found to be a general solvent to solubilize and immobilize boronic acids efficiently. In another preferred embodiment, dichloromethane provided higher yields of immobilization (entries 5 vs 6). The limited solubility of water in dichloromethane may minimize the back reaction (hydrolysis).

When using THF as solvents a wide variety of functionalized arylboronic acids presenting different steric and electronic characteristics were found to immobilize efficiently onto DEAM-PS (entries 6–18).

Hydroxylic solvents such as methanol and ethanol allowed for a dynamic transesterification process to take place, leading to non-quantitative immobilization (Table 5, entry 1). A control experiment was devised to measure the extent of transesterification of DEAM-PS supported p-tolylboronic acid (R=p-Tolyl) in 7:1 THF/ethanol. Equilibrium was reached within 15 minutes of exposure of the supported p-tolylboronic acid to the 7:1 THF/ethanol solvent. Successive incubations of the resin under constant resin:solvent proportions, followed by rinses with dry THF, revealed that approximately 40% p-tolylboronic acid was released from the resin under these conditions. The reverse reaction (resin+p-tolylboronic acid) gave a similar outcome under the same conditions, showing that the transesterification process was under equilibrium.

In one preferred embodiment, it was preferable to employ a cleavage solution prepared from air- and peroxide-free, freshly distilled THF. The 2,6-di-t-butyl-p-cresol used as stabilizer in non-distilled THF could accumulate in the polymer matrix of DEAM-PS and contaminate products upon cleavage. This could be prevented by the use of distilled THF for resin washing and for the cleavage solution. In a preferred embodiment, in the absence of the stabilizer, freshly distilled THF was used in order to avoid a presumed build-up of peroxides, which have caused oxidation of the boronic acids into the corresponding phenols.

TABLE 5

Immobilization of various boronic acids onto 1.[a]

| Entry | $R^2$ | Solvent | Yield (%)[b] | Purity[c] |
|---|---|---|---|---|
| 1 | 4-Me—$C_6H_4$ | MeOH | 72 | >95 |
| 2 | 4-Me—$C_6H_4$ | NMP | 80 | >95 |
| 3 | 4-Me—$C_6H_4$ | $Et_2O$ | 90 | >95 |
| 4 | 4-Me—$C_6H_4$ | toluene | 88 | >95 |
| 5 | 4-Me—$C_6H_4$ | $CH_2Cl_2$ | 98 | >95 |
| 6 | 4-Me—$C_6H_4$ | THF | 89 | >95 |
| 7 | 4-Br—$C_6H_4$ | THF | 97 | >95 |
| 8 | 4-MeO—$C_6H_4$ | THF | 87 | >95 |
| 9 | 4-$HO_2$C—$C_6H_4$ | THF | 90 | >95 |
| 10 | 2-$HO_2$C—$C_6H_4$ | THF | 51 | >95 |
| 11 | 3-$H_2$N—$C_6H_4$ | THF | 91 | >95 |
| 12 | 2-CHO—$C_6H_4$ | THF | 98[d] | >95 |
| 13 | 4-PhO—$C_6H_4$ | THF | 93 | >95 |
| 14 | 4-$BrCH_2$—$C_6H_4$ | THF | 85 | >95 |
| 15 | 2,6-di-Me—$C_6H_3$ | THF | 46 | >95 |
| 16 | 2,4-di-F—$C_6H_3$ | THF | 46 | >95 |
| 17 | 2-naph | THF | 89[d] | >95 |
| 18 | (E)-PhCH=CH | THF | 81 | >95 |

[a]Coupling reactions were conducted by shaking resin 1 (1 equiv, 120 mg, 1.15 mmol/g) with the boronic acid (1.3 equiv) in the indicated solvent (1.5 mL) at room temperature for 1 hour in a polypropylene fritted vessel.
[b]Yields of boronic acid recovered after cleavage from the resin with 5% $H_2O$/THF for 1 min at rt and washed with 5% $H_2O$/THF (3x). The resin was rinsed with the reaction solvent (3x) prior to cleavage. For entries 4 and 5, additional THF rinses were carried out (3x). The reported yields are an average of mass balance and internal standardization based on the loading of resin 1 measured by elemental analysis.
[c]Estimated by comparison of $^1$H NMR spectra of starting and recovered boronic acids.
[d]Calculated only from mass balance, tendency of this boronic acid to form anhydrides made NMR quantitation difficult.

Figure 4:
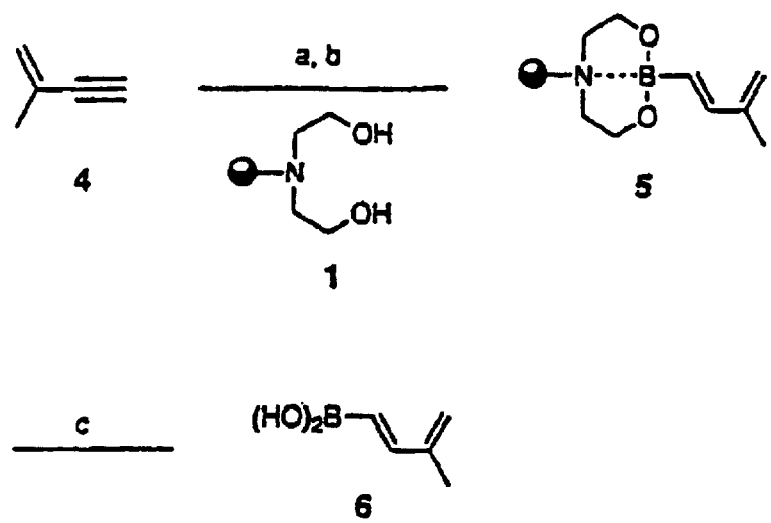
FIG. 4 is a schematic summarizing resin capture purification of dienylboronic acid, as described in detail in Example 1, below.

Purification of crude dienylboronic acid. Referring now to FIG. 4, solid support resin 1 was employed in the purification of crude dienylboronic acid 6 (see, e.g., Vaultier (1987) Tetrahedron Lett. 28:4169–4172).

Dienylboronic acid was produced by treating 2-methyl-1-buten-3-yne (compound 4) with dicyclohexylborane followed by oxidative workup. The purification of alkenylboronic acids such as compound 6 can be considerably troublesome.

The use of resin 1 to capture dienylboronic acid (compound 6) and eliminate excess reagents and cyclohexanol oxidation by-product facilitated its purification through simple rinsing of its resin-bound form depicted as conjugated compound 5.

FIG. 4 is a schematic summarizing resin capture purification of dienylboronic acid with resin 1 following dicyclohexylboration/oxidation of compound 4. In one preferred embodiment reaction "a", the addition of compound 4 to $(C_6H_{11})_2BH$ (1.0 equiv) was conducted in THF, 0° C., 0.5 h; RT, 0.5 h; then $(CH_3)_3NO.2H_2O$ (2.0 equiv), 0° C. to RT, 12 h; in one preferred embodiment, reaction "b" represents DEAM-PS resin 1 (0.5 equiv), $CH_2Cl_2$, 1.5 h; and reaction "c" represents THF/$H_2O$ 9:1, RT, 1.5 h, 95% (overall yield based on compound 1).

Example 2

Resin-to-Resin Borono-Mannich Transfer Reactions Using Solid-Supported Boronic Acids Examples 2 and 3 describe preferred embodiments for practicing the methods of the invention. The concept of resin-to-resin transfer reactions (RRTR), also called two resin systems, constitutes a significant simplification of solid-phase organic synthesis (SPOS) which can be extremely valuable as a time saving strategy in combinatorial chemistry. RRTR systems allow for the convergent solid-phase synthesis and eventual coupling of fragments for which a linear SPOS strategy would involve incompatible reaction conditions.

In RRTR, transfer of one resin-bound substrate to solution-phase is necessary in order to effect its coupling to the other resin-bound substrate. A neutral chemical agent, or chaperone, is required to promote this event under conditions compatible with the desired reaction (in the resin-to-resin acyl transfer system reported by Hamuro (1999) J. Am. Chem. Soc. 121:1636–1644, the transfer agents employed therein were termed chaperones because they also act as solution-phase activators).

In particular, in Example 2, a resin-to-resin borono-Mannich reaction between dialkylamino resins and solid supported boronic acids of the invention is described. This embodiment is one optimization of a resin-to-resin transfer reaction between secondary amines and arylboronic acids to make arylglycine derivatives.

N,N-diethanolaminomethylpolystyrene (DEAM-PS) was made as described above (see Example 1). All boronic acids were purchased from commercial sources (Sigma-Aldrich, Lancaster Synthesis, Windham, N.H., or Combi-Blocks, San Diego, Calif.) and were loaded onto DEAM-PS as described above. The dialkylaminotrityl resins were made by the condensation of excess diamine (20 equiv.) onto commercial chlorotrityl polystyrene (Rapp Polymere, Tübingen, Germany) swelled in N-methyl-2-pyrrolidone (NMP). Loading measurements were carried out by analysis of nitrogen content. For RRTR's, runs were done in 10 mL Teflon™ fritted vessels on a Quest 210™ instrument with solvent wash unit (Argonaut Technologies, San Carlos, Calif.). Cleavage was effected on-line and crude products were obtained after evaporation of solvents. Yields and purity were estimated by comparison with an internal NMR standard (EtOAc, 15 secs relaxation delay).

Figure 6:
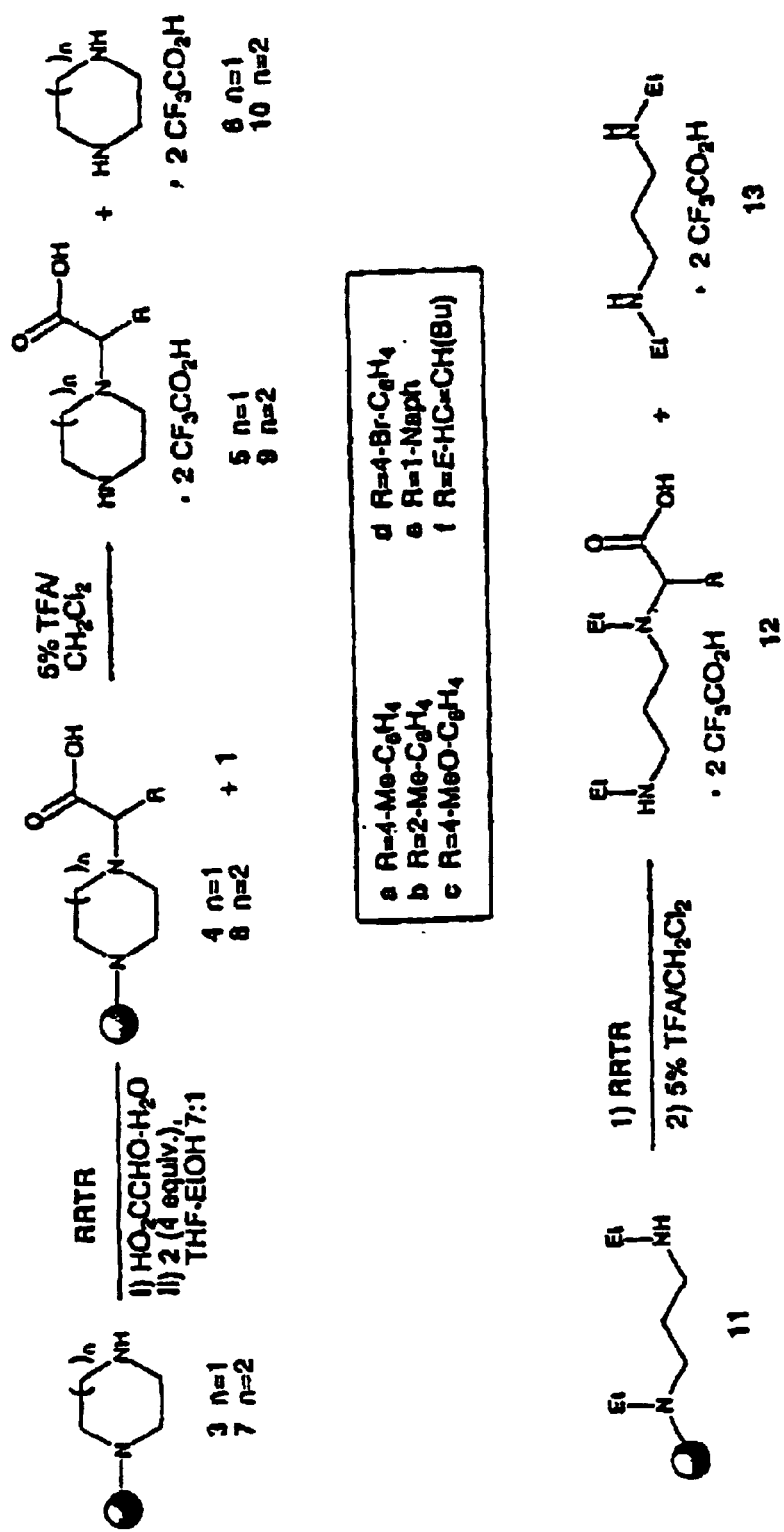
FIG. 6 is a schematic summarizing a RRTR with different DEAM-PS-boronates and cleavage of the final resin mixture to provide arylglycine derivatives, as described in detail in Example 2, below.

Typical procedure for the borono-Mannich RRTR involved preparation of compound 5c of FIG. 6. FIG. 6 is a schematic summarizing a borono-Mannich resin-to-resin transfer reaction between boronic acids supported onto N,N-diethanolaminomethyl polystyrene and the iminium intermediate formed from dialkylamino resin 3 and glyoxylic acid.

Figure 5:
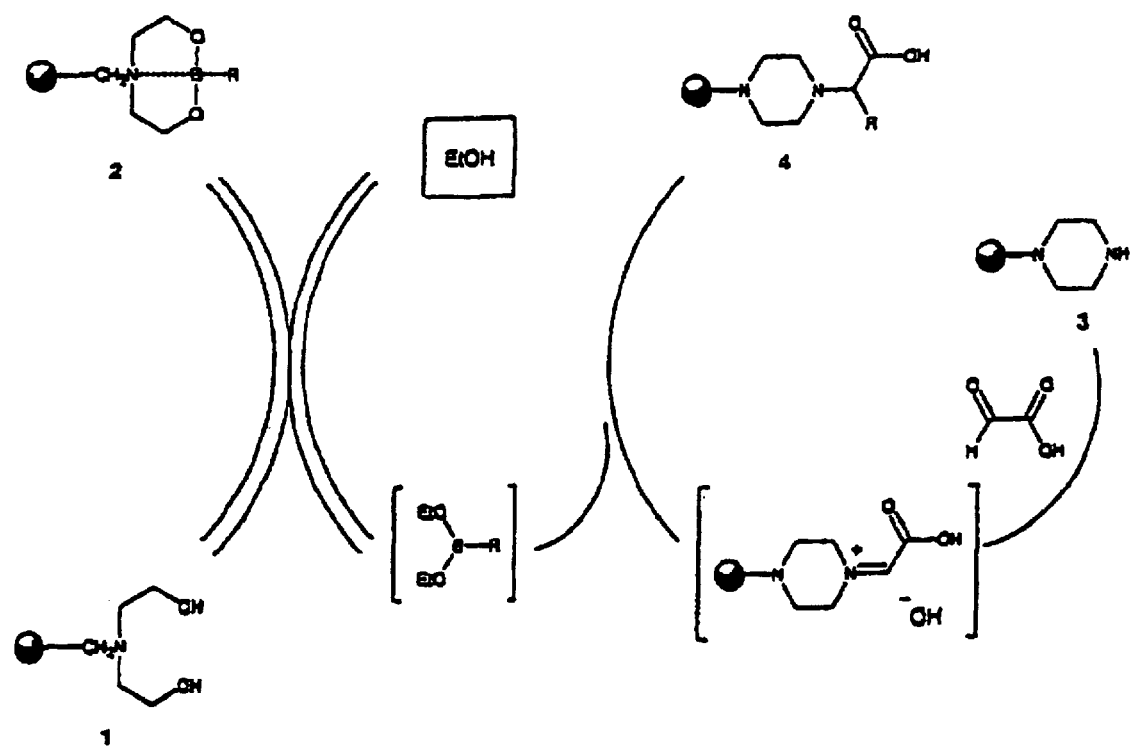
FIG. 5 is a schematic summarizing a borono-Mannich resin-to-resin transfer reaction between boronic acids supported onto N,N-diethanolaminomethyl polystyrene and the iminium intermediate formed from dialkylamino resin 3 and glyoxylic acid, as described in detail in Example 2, below.

Referring now to FIGS. 5 and 6, in one preferred embodiment, to piperazinetrityl resin 3 (32 mg, 0.030 mmol, theoretical (theor.) loading: 0.95 mmol/g) weighed out in a reaction vessel was added a solution of glyoxylic acid monohydrate (0.032 mmol) in dry THF (2 mL). The suspension was allowed to mix at room temperature (rt) under a nitrogen atmosphere for 2 hours. An excess of DEAM-PS boronic ester 2c (127 mg, 0.120 mmol, theor. loading: 0.95 mm/g) was then added followed by 1.5 ml of 8:3 THF/EtOH. The suspension was mixed at 65° C. for 48 hours (h)

under a nitrogen atmosphere and then cooled to rt. The resin mixture was filtered and rinsed with 8:3 THF/EtOH (3×), 2:1 THF/H$_2$O (3×) and CH$_2$Cl$_2$ (5×), mixed with 3 ml of 5% TFA/CH$_2$Cl$_2$ in the same vessel at rt for one hour, then filtered and rinsed with CH$_2$Cl$_2$ (3×) and MeOH (2×). The combined filtrates were concentrated and dried under high vacuum for 12 h to afford crude compound 5c as a clear oil (14 mg, 90% conversion). An analytically pure sample was obtained by dissolving the oil in a small amount of methanol followed by addition of ether, filtration of the precipitate, and concentration of the resulting solution.

The boronic acid Mannich reaction was compatible with a wide range of solvents, including hydroxylic ones. In one embodiment of the invention, an alcohol was employed as co-solvent to act as neutral phase transfer agent to cleave a solid support-derivatized boronic acid of the invention (e.g., DEAM-PS) under mild conditions appropriate toward a RRTR system. The boronic acid liberated in situ as an ester was then add to the imine formed between an amino functionalized resin and an activated aldehyde such as glyoxylic acid. The resulting arylglycine products obtained after cleavage of the resin mixture were compounds of particular interest for their biological activity.

Referring now to Table 13, in one preferred embodiment, conditions using DEAM-PS supported p-tolylboronic acid (compound 2, R=4-Me—C$_6$H$_4$— in FIG. 5), piperazinetrityl resin, and glyoxylic acid in a semi-automated synthesizer, as described, above were explored. The rate of reaction was found to be dependent on the nature of the solvent system; THF/EtOH (7:1) and DMF/n-BuOH (7:1) being first and second best respectively of those tried for the system as described in Table 13.

TABLE 13

Figure 7:
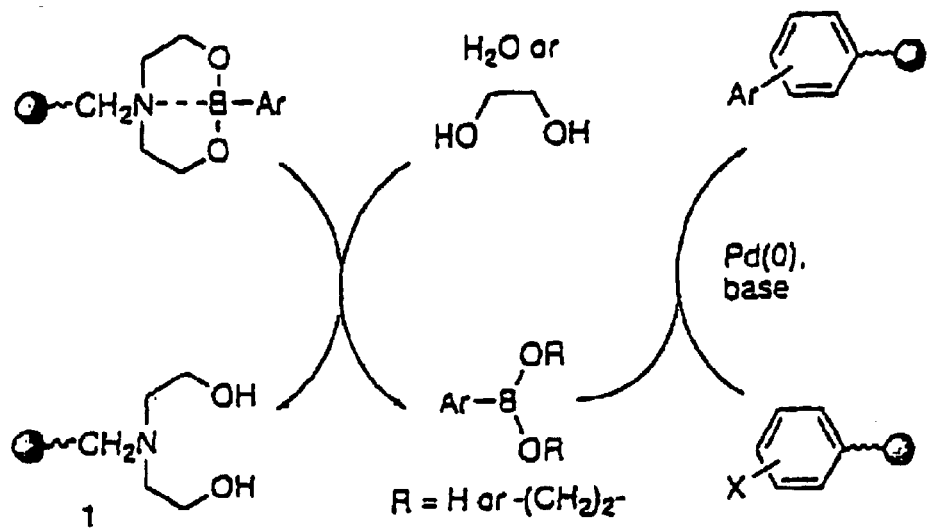
FIG. 7, Scheme 1 is a schematic summarizing a RRTR with an arylboronic acid as described in detail below in Example 3; Scheme 2 is a schematic summarizing the transfer of resin-bound p-tolueneboronic acid to Wang resin-bound p-iodobenzoic acid as described in detail below in Example 3.
Figure 7:
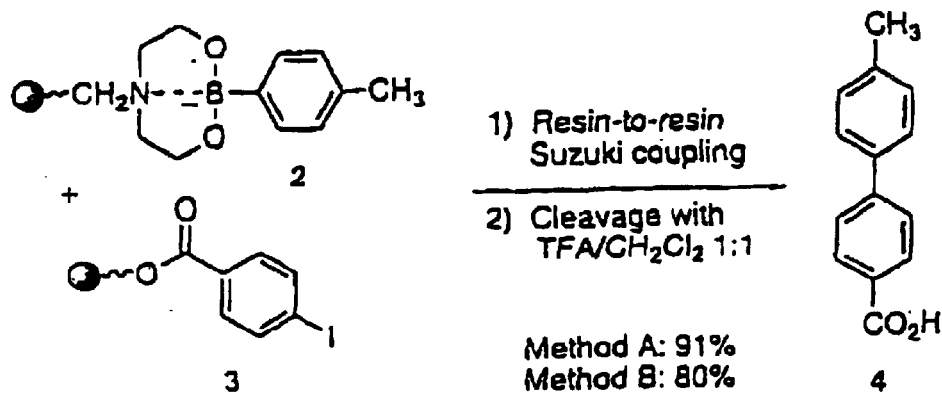

Optimization of solvent system, at 65° C. for 24 h, for the borono-Mannich RRTR of compound 3, FIG. 6 and compound 2, FIG. 7, to give compound 5, FIG. 6.[a]

| Entry | Solvent | Conversion (%)[c] |
|---|---|---|
| 1 | 7:1 DMF/EtOH | 65 |
| 2 | 7:1 DMF/n-BuOH | 54 |
| 3 | 7:1 dioxane/n-BuOH | 23 |
| 4 | 7:1 THF/(HOCH$_2$)$_2$ | 37 |
| 5 | 7:1 THF/EtOH | 79 |

[a]Preparation of resin substrates, RRTR trials, and subsequent cleavage of the resin mixture were carried out as indicated above.
[b]Based on the relative amounts of product and bis(trifluoroacetate) salt 6, FIG. 6, calculated by integration of relevant signals by $^1$H NMR after 24 h reaction time.

In one preferred embodiment, one set of experimental conditions first involved incubating the dialkylamino resin with glyoxylic acid monohydrate (1.1 equivalent) for two hours in dry THF at room temperature. Then, four equivalents of DEAM-PS bound boronic acid were added along with the appropriate volume of 8:3 THF/EtOH. The suspension was shaken at 65° C. for up to 48 hours. Conversion levels superior to 75% were observed in the case of p-tolylboronic acid as seen after cleavage of the final resin mixture 1 and 4 (FIG. 5) with 5% trifluroacetic acid/dichloromethane to give the corresponding amino acid product 5a as a bis(trifluoroacetate) salt (Table 2, below). The rest of unreacted starting resin 3 was cleaved into the bis(trifluoroacetate) salt of piperazine (compound 6) which can be eventually removed by precipitation. There were no other by-products observed, as the leftover DEAM-PS resin (compound 1) did not give any artifacts upon treatment with trifluoroacetic acid in the product release step.

RRTR of compound 3, compound 7, and compound 11 with different DEAM-PS-boronates and cleavage to provide arylglycine derivatives compounds 5, 9, and 12. Referring now to FIG. 6 and Table 2, different substrates for use in the RRTR systems of the present invention were explored.

FIG. 6 illustrates preferred embodiments of the RRTR of compound 3, compound 7, and compound 11 with different DEAM-PS-boronates and cleavage of the final resin mixture to provide arylglycine derivatives compounds 5, 9, and 12, respectively. As shown in Table 2, conversion values and product yields were generally good. Conversion values for the RRTR of electron-poor arylboronic acids were found to be lower.

A typical procedure for the preparation of 3 comprised the following. Trityl chloride resin (500 mg, 0.535 mmol, theor. loading: 1.07 mmol g$^{-1}$) was weighed into a 70 ml pp vessel and a solution of piperazine (920 mg, 10.7 mmol) in NMP (20 mL) was added. The reaction was shaken at rt overnight. The suspension was drained, and the resin was rinsed with MeOH (3×), and CH$_2$Cl$_2$ (6×). The resin was dried under high vacuum for >24 h to afford a yellow resin (460 mg, theor. 515 mg, 1.02 mmol g$^{-1}$).

A typical procedure for the borono-Mannich RRTR for the preparation of 5c comprised the following. To piperazinetrityl resin 3 (32 mg, 0.030 mmol, theor. loading: 0.95 mmol g$^{-1}$) weighed out in a 10 ml teflon fritted reaction vessel was added a solution of glyoxylic acid monohydrate (0.032 mmol) in dry THF (2 mL). The suspension was allowed to mix at rt under a nitrogen atmosphere for 2 h. An excess of DEAM-PS boronic ester 2c (127 mg, 0.120 mmol, theor. loading: 0.95 mm g$^{-1}$) was then added, followed by a 8:3 THF/EtOH solution (1.5 mL). The suspension was mixed at 65° C. for 48 h under a nitrogen atmosphere and then cooled to rt. The resin mixture was filtered and rinsed with 8:3 THF/EtOH (3×), 2:1 THF/H$_2$O (3×) and CH$_2$Cl$_2$ (5×), mixed with 3 ml of 5% TFA/CH$_2$Cl$_2$ in the same vessel at rt for 1 h, then filtered and rinsed with CH$_2$Cl$_2$ (3×) and MeOH (2×). The combined filtrates were concentrated and dried under high vacuum for 12 h to afford crude 5c as a clear oil (14 mg, 90% conversion). An analytically pure sample was obtained by dissolving the oil in a small amount of methanol followed by addition of ether, filtration of the precipitate, and concentration of the resulting solution.

Selected data for all products: 5a: $^1$H NMR (300 MHz, CD$_3$OD) δ 7.30 (d, J=8.0 Hz, 2H), 7.20 (d, J=8 Hz, 2H), 4.17 (s, 1H), 3.23–3.20 (m, 4H), 2.77–2.74 (m, 4H), 2.33 (s, 3H); $^{13}$C NMR (75 MHz, CD$_3$OD) δ 173.5, 140.5, 132.0, 130.7, 130.1, 73.3, 48.1, 44.3, 21.2; ESMS 235.1 (M+H$^+$). 5b: $^1$H NMR (300 MHz, CD$_3$OD) δ 7.40 (d, J=6.0 Hz, 1H), 7.24–7.18 (m, 3H), 4.50 (s, 1H), 3.20–3.16 (m, 4H), 2.85–2.82 (m, 4H), 2.45 (s, 3H); $^{13}$C NMR (75 MHz, CD$_3$OD) δ 174.2, 138.9, 134.7, 131.8, 129.3, 129.1, 127.1, 69.3, 47.7, 44.9, 19.4; ESMS 235.3 (M+H$^+$). 5c: $^1$H NMR (300 MHz, CD$_3$OD) δ 7.34 (d, J=8.6 Hz, 2H), 6.93 (d, J=8.9 Hz, 2H), 4.13 (s, 1H), 3.79 (s, 3H), 3.23–3.19 (m, 4H), 2.75–2.72 (m, 4); $^{13}$C NMR (100 MHz, CD$_3$OD) δ 174.3, 161.7, 131.2, 127.9, 115.2, 73.1, 55.7, 48.3, 44.7; ESMS 251.1 (M+H$^+$). 5d: $^1$H NMR (300 MHz, CD$_3$OD) δ 7.55 (d, J=8.5 Hz, 2H), 7.36 (d, J=8.5 Hz, 2H), 4.22 (s, 1H), 3.25–3.19 (m, 4H), 2.77–2.73 (m, 4H); ESMS 301.1 (M+H$^+$). 5e: $^1$H NMR (300 MHz, CD$_3$OD) δ 8.43 (d, J=7.9

Hz, 1H) 7.91–7.88 (m, 2H), 7.60–7.45 (m, 4H), 5.06 (s, 1H) 3.16–3.12 (m, 4H), 2.93–2.90 (m, 4H); $^{13}$C NMR (75 MHz, CD$_3$OD) δ 174.3, 135.7, 133.4, 132.4, 130.5, 129.8, 128.4, 127.6, 127.1, 126.2, 125.2, 70.1, 47.9, 45.2; ESMS 271.1 (M+H$^+$). 5f: $^1$H NMR (300 MHz, CD$_3$OD) δ 5.89 (dt, J$_1$=15.0 Hz, J$_2$=7.0 Hz, 1H) 5.48 (dd, J$_1$=15.0 Hz, J$_2$=8.0 Hz, 1H) 3.70 (d, J=8.0 Hz, 1H) 3.26–3.23 (m, 4H), 2.95–2.87 (m, 2H), 2.84–2.76 (m, 2H), 2.12 (app q, J=7.0 Hz, 2H) 1.44–1.29 (m, 4H) 0.92 (t, J=7.0 Hz, 3H); $^{13}$C NMR (100 MHz, CD$_3$OD) δ 173.9, 140.5, 124.3, 71.8, 48.1, 44.6, 33.2, 32.2, 23.2, 14.2; ESMS 227.2 (M+H$^+$). 9c: $^1$H NMR (300 MHz, CD$_3$OD) δ 7.38 (d, J=8.7 Hz, 2H), 6.96 (d, J=8.6 Hz, 2H), 4.65 (s, 1H), 3.80 (s, 3H), 3.34–3.21 (m, 2H) 3.21–3.10 (m, 4H), 3.01–2.97 (m, 2H), 2.07–2.04 (m, 2H); $^{13}$C NMR (75 MHz, CD$_3$OD) δ 174.4, 161.8, 131.5, 128.0, 115.4, 73.1, 55.8, 53.3, 49.2, 46.7, 45.9, 26.1; ESMS 265.1 (M+H$^+$). 12c: $^1$H NMR (300 MHz, CD$_3$OD) δ 7.48 (d, J=8.8 Hz, 2H), 7.03 (d, J=8.8 Hz, 2H), 4.96(s, 1H), 3.83 (s, 3H), 3.13–3.01 (m, 8H), 2.18–2.03 (m, 2H), 1.33–1.25 (m, 3H); ESMS 295.4 (M+H$^+$).

TABLE 2

Preparation of arylglycine derivatives by borono-Mannich RRTR as shown in FIG. 6[a]

| Entry | Amino Resin | DEAM-PS-Boronate 2 | Product | Conversion %[b] | Yield (%)[c] |
|---|---|---|---|---|---|
| 1 | 3 | R = 4-Me—C$_6$H$_4$ | 5a | 79 | 90 |
| 2 | 3 | R = 2-Me—C$_6$H$_4$ | 5b | 81 | 73 |
| 3 | 3 | R = 4-MeO—C$_6$H$_4$ | 5c | 90 | >95 |
| 4 | 3 | R = 4-Br—C$_6$H$_4$ | 5d | 21 | 10 |
| 5 | 3 | R = 1-Naph | 5e | 78 | 90 |
| 6 | 3 | R = E—HC=CH(Bu) | 5f | 89 | >95 |
| 7 | 7 | R = 4-MeO—C$_6$H$_4$ | 9c | 95 | 91 |
| 8 | 11 | R = 4-MeO—C$_6$H$_4$ | 12c | 76 | 82 |

[a]Preparation of resin substrates, RRTR trials, and subsequent cleavage of the resin mixture were carried out as indicated herein.
[b]Based on the relative amounts of product and respective bis (trifluoroacetate) salt 6, 10, or 13 calculated by integration of relevant peaks by $^1$H NMR after 24–48 h reaction time.
[c]Yields of crude product based on $^1$H NMR analysis with an internal standard.

Observed conversion values for the reactions conditions of Table 2 were highest for DEAM-PS supported p-methoxybenzene boronic acid (entries 3, 7, 8), and lowest for p-bromophenyl boronic acid (entry 4). DEAM-PS-supported alkenylboronic acids were also appropriate substrates (entry 6). In this case the use of a RRTR strategy using DEAM-PS resin was even more advantageous for handling and storage purposes since the otherwise air-sensitive alkenylboronic acids were stabilized through immobilization as diethanolamine adducts. Use of an acyclic amine (compound 11) was equally successful (entry 8), demonstrating that a variety of secondary amines such as terminal N-alkylamino acids can be employed in the methods of the invention. Analytically pure samples of most reported compounds could be obtained following precipitation with methanol/ether and filtration of the unreacted dialkylamine as a bis(trifluoroacetate) diammonium salt.

The borono-Mannich RRTR incorporating the derivatized solid supports of the present invention was also useful for the convergent solid-phase synthesis of libraries of arylglycine derivatives. This could be achieved by combining libraries of dialkylamino resins with libraries of supported arylboronic acids made by derivatizing functionalized ones immobilized onto DEAM-PS.

Example 3

Resin-to-Resin Suzuki Coupling of Solid Supported Arylboronic Acids

Example 3 describes one embodiment of the present invention for resin-to-resin Suzuki coupling reactions via phase transfer of solid supported arylboronic acids under both aqueous and anhydrous conditions. The potential of these methods is illustrated with the convergent solid-phase synthesis of unsymmetrically functionalized biphenyl compounds.

In one preferred embodiment, aqueous conditions were optimized for Suzuki cross-coupling in which water or a hydroxylic co-solvent acts as phase transfer agent. As shown conceptually in scheme 1, FIG. 7, hydrolysis or transesterification on the DEAM-PS boronate linkage is expected to liberate the free boronic acid (or ester) which will be transferred in situ to a haloarene resin under palladium(0) catalysis and added base.

Typical synthesis of 4-Iodobenzoate Wang-PS resin (3, FIG. 7). To a suspension of Wang resin (100 g, 0.63 mmol, theor. loading: 0.63 mmol g$^{-1}$) in 10 mL of CH$_2$Cl$_2$ in a pp vessel were added successively 4-iodobenzoic acid (240 mg, 0.95 mmol), triethylamine (135 μL, 0.98 mmol), 1-(3-Dimethylaminopropyl)-3-ethylcarbodiimide (EDCI) (180 mg, 0.94 mmol), and HOBtH$_2$O (15 mg, 0.098 mmol), vortexing after each addition. The suspension was shaken at rt for 24 h, after which the resin was rinsed with DMF (5×), CH$_2$Cl$_2$ (5×), and dried under high vacuum for >24 h, affording 1.18 g of a white resin (theor.: 1.14 g, 0.55 mmol g$^{-1}$).

Typical procedure for the Suzuki RRTR using 4-iodobenzoate Wang-PS resin: Preparation of 4, FIG. 7. To a mixture of DEAM-PS supported p-tolylboronic acid 2 (77 mg, 0.075 mmol, theor. loading: 0.97 mmol g$^{-1}$) and 4-iodobenzoate Wang-PS resin 3 (49 mg, 0.050 mmol, theor. loading: 1.02 mmol g$^{-1}$) in a 10-mL round-bottom flask were added successively 2.5 mL of DMF, 0.25 mL of ethylene glycol, 0.25 mL of triethylamine, and the dichloro [1,1'-bis(diphenylphosphino)ferrocene]palladium (II) dichloromethane adduct (PdCl$_2$(dppf).CH$_2$Cl$_2$) (4 mg, 0.005 mmol). The flask was equipped with a reflux condenser. The suspension was stirred gently at 105° C. for 8 h under a nitrogen flow, then the second portion of PdCl$_2$(dppf).CH$_2$Cl$_2$ (4 mg, 0.005 mmol) was added. The heating was resumed for 12 h, after which the reaction mixture was cooled down to rt. The mixture was transferred to a pp vessel, then rinsed with DMF (1×), 1:1 DMF/H$_2$O (3×), MeOH (3×), CH$_2$Cl$_2$ (6×). The resulting brown resin was swollen in CH$_2$Cl$_2$ (1 mL) and trifluoroacetic acid (1 mL), and the resulting suspension was stirred for 2 h. The resin was filtered and rinsed with a 1:1 CH$_2$Cl$_2$/TFA solution (2×). The combined filtrates were concentrated and dried under high vacuum, affording a pale brown solid. (105% yield by mass; 64% yield by $^1$H NMR with EtOAc int. std.): $^1$H NMR (500 MHz, CD$_3$OD) δ 8.06 (d, J=8 Hz, 2H), 7.69 (d, J=8 Hz, 2H), 7.55 (d, J=8 Hz, 2H), 7.27 (d, J=8 Hz, 2H), 2.37 (s, 3H); $^{13}$C NMR (75 MHz, 5% D$_2$O in CD$_3$OD) δ 164.9, 147.0, 139.3, 138.3, 131.3, 130.7, 128.0, 127.7, 21.1; IR (microscope) 3300–2500, 3028, 2916, 1678, 1607, 1358 cm$^{-1}$; HRMS (EI, m/z) calcd for C$_{14}$H$_{12}$O$_2$ 212.0837. found 212.0838.

Suzuki RRTR under aqueous conditions. Referring now to FIG. 7, Scheme 2, and Table 3, the transfer of DEAM-PS resin-bound p-tolueneboronic acid (compound 2) to Wang resin-bound p-iodobenzoic acid (compound 3) was tested with different stoichiometries under various solvent, base and temperature conditions. The resulting resin mixture was then treated with 1:1 tifluoroacetic acid/dichloromethane to liberate the biphenyl product (compound 4) and, if any, unreacted p-iodobenzoic acid. In all cases, no boronic acid was recovered. It was, therefore, completely released to solution under the reaction and resin washing conditions used. Leftover DEAM-PS resin did not liberate any by-products upon treatment with TFA. In a preferred embodiment, "Method A" was DEAM-PS-boronic ester (4 equiv.), iodoarene resin (1 equiv.), $Na_2CO_3$ (5 equiv., $2M/H_2O$), 20% $Pd(PPh_3)_4$, toluene/MeOH 3:1, 85° C., 24 h; and, "Method B" was DEAM-PS-boronic ester (4 equiv.), iodoarene resin (1 equiv.), 20% $Pd_2(dba)_3$, $DMF/Et_3N/(HOCH_2)_2$ 8:1:1, 105° C., 24 h.

Conversion results are summarized in Table 3:

TABLE 3

Suzuki RRTR of compound 2 and compound 3 under aqueous conditions.[a]

| Entry | Solvent | Base[b] | Equiv. of 2 | Temp. (° C.) | Time (h) | Conversion %[c] |
|---|---|---|---|---|---|---|
| 1 | PhMe/EtOH 3:1 | $Na_2CO_3$ | 4 | 85 | 20 | 100 |
| 2 | PhMe/EtOH 3:1 | $K_2CO_3$ | 4 | 85 | 20 | 100 |
| 3 | PhMe/EtOH 3:1 | $Na_2CO_3$ | 3 | 85 | 16 | 70 |
| 4 | $DME/H_2O$ 9:1 | $Na_2CO_3$ | 4 | 85 | 20 | 60 |
| 5 | $DMF/H_2O$ 9:1 | $Na_2CO_3$ | 3 | 85 | 20 | 35 |

[a]Typical trials were carried out with 40 mg of compound 3 (0.55 mmol/g) and the according amount of compound 2 in 2 mL degassed solvent, and 10–20% $Pd(PPh_3)_4$ as catalyst.
[b]An additional equiv. relative to compound 2 was employed (from a 2 M aqueous solution).
[c]Measured by $^1H$ NMR integration on crude reaction products.

With 10–20% Pd(0) catalyst loading and either sodium or potassium carbonate as base, the original Suzuki conditions (Suzuki, A., in Metal-catalyzed cross-coupling reactions, Eds. Diederich, F., et al., Wiley-VCH, 1997, Chapt. 2) using toluene/ethanol (3:1) as solvent gave the highest conversions (entries 1 to 2). Using the optimal conditions of entry 1, designated Method A (Scheme 2, FIG. 7), a larger scale reaction (~0.1 mmol) afforded a 91% yield of essentially pure compound 4.

Suzuki RRTR under anhydrous conditions. Referring now to FIG. 7, scheme 2 and Table 4, anyhydrous conditions employing a tertiary amine as base were also optimized for RRTR processes that use water-sensitive substrates.

TABLE 4

Suzuki RRTR of 2 and 3 under anhydrous conditions.[a]

| Entry | Solvent | Base[b] | Transfer Agent | Temp. (° C.) | Time (h) | Conversion %[c] |
|---|---|---|---|---|---|---|
| 1 | DMF | $Et_3N$[b] | $(HOCH_2)_2$[b] | 105 | 20 | 100 |
| 2 | DMF | $Et_3N$[c] | $(HOCH_2)_2$[c] | 105 | 20 | 100 |
| 3 | DMF | $Et_3N$[b] | $(HOCH_2)_2$[b] | 85 | 20 | 100 |
| 4 | DMF | $Et_3N$[c] | $(HOCH_2)_2$[c] | 85 | 20 | 85 |
| 5 | DMF | $N(CH_2CH_2OH)_3$[b] | $N(CH_2CH_2OH)_3$[b] | 105 | 20 | 40 |
| 6 | PhMe | $N(CH_2CH_2OH)_3$[b] | $N(CH_2CH_2OH)_3$[b] | 105 | 20 | 45 |
| 7 | dioxane | $NH(CH_2CH_2OH)_2$[b] | $NH(CH_2CH_2OH)_2$[b] | 85 | 20 | 45 |

[a]Typical trial same as in Table 3 except for the constant use of 4 equiv. of compound 2 (107 mg, 0.82 mmol/g).
[b]A large excess is used, ca. 10% v/v.
[c]20 equiv.
[d]Measured by $^1H$ NMR integration on crude reaction products.

The use of diethanolamine and triethanolamine as phase transfer agents that could also function as required base was examined. As shown from entries 5 to 7 (Table 4), diethanolamine and triethanolamine showed lower conversion percentages (this may be because the transmetallation of the corresponding diethanolamine boronic esters with the PS-Ar—Pd—I intermediate is significantly slower than with the ethylene glycol esters). The use of ethylene glycol as transfer agent (Scheme 1, FIG. 7) with triethylamine as base in DMF (dimethylformamide) was found to be a preferred embodiment (entries 1 to 4, Table 4). When triethylamine and ethylene glycol (1:1) were used in large excess, full conversion was achieved at 85° C. for 20 h (entry 3, Table 4). Furthermore, in one preferred embodiment, substitution of $Pd(PPh_3)_4$ for $Pd_2(dba)_3$ appeared to result in crude reaction products of apparently higher purity. These latter conditions were designated "Method B," with a temperature of 105° C. to ensure completion of more demanding substrates. On a larger scale, Method B afforded a 80% yield of compound 4.

Referring now to Table 11, and FIG. 7, Scheme 2, the effect of the nature of the base on conversion using 50 mol % $Pd_2(dba)_3$ at 60° C. was explored. In one preferred embodiment, fluoride and triethylamine were found to be satisfactory, and provided some biphenyl product at room temperature (entries 7 and 10).

TABLE 11

Anhydrous Suzuki RRTR of 2 and 3. Effect of base and temperature under $Pd_2(dba)_3$ catalysis (50 mol %).[a]

| Entry | Base | Temp. (° C.) | Conversion (%)[b] | Yield (%)[c] |
|---|---|---|---|---|
| 1 | NaOH | 60 | —[d] | 0[d] |
| 2 | $Ba(OH)_2$ | 60 | —[d] | 0[d] |
| 3 | $K_2CO_3$ | 60 | —[d] | 0[d] |
| 4 | $Cs_2CO_3$ | 60 | —[d] | 0[d] |
| 5 | $K_3PO_4$ | 60 | —[d] | 0[d] |
| 6 | KF | 60 | >98 | >98 |
| 7 | KF | 25 | 78 | 74 |

TABLE 11-continued

Anhydrous Suzuki RRTR of 2 and 3. Effect of base and temperature under Pd$_2$(dba)$_3$ catalysis (50 mol %).[a]

| Entry | Base | Temp. (° C.) | Conversion (%)[b] | Yield (%)[c] |
|---|---|---|---|---|
| 8 | CsF | 60 | >98 | >98 |
| 9 | Et$_3$N | 60 | >98 | >98 |
| 10 | Et$_3$N | 25 | 72 | 71 |

[a]Typical trials were carried out with 20 mg of 3 (0.55 mmol/g) and 2 (3.2 equiv, 45 mg, 0.79 mmol/g) with the indicated base (10 equiv) and 50 mol % Pd$_2$(dba)$_3$ as catalyst in DMF-ethylene glycol 10:1 (2.5 mL) for 18 h.
[b]Measured by $^1$H NMR integration of representative signals on crude reaction products.
[c]Non optimized yields of crude products after cleavage from the resin and drying in vacuo for >12 hours. The reported values are usually an average of mass balance and internal standardization.
[d]Premature cleavage.

Referring now to Table 12 and FIG. 7, Scheme 2, in one preferred embodiment, conditions were explored that were mild enough to minimize alcoholysis of the Wang ester linker while still providing complete coupling within 20 hours at 105° C., with only 1.5 equivalents of DEAM-PS supported boronic acid, and with a lower catalyst loading. In one embodiment, triethylamine, essentially as a co-solvent (entries 7–8), was an effective base in combination with 20% PdCl$_2$(dppf) as catalyst. In one preferred embodiment, PdCl$_2$(dppf) was added in 2–3 portions at a few hours interval in order to minimize the effects of catalyst inactivation. The use of cesium fluoride and TBAF as bases led to fall conversion (entries 2–3).

TABLE 12

Anhydrous Suzuki RRTR of 2 and 3. Effect of base and catalyst at high temperature (105° C.).[a]

| Entry | Base | Catalyst | Conversion (%)[b] | Yield (%) |
|---|---|---|---|---|
| 1 | NaF | Pd$_2$(dba)$_3$ | 29 | 33 |
| 2 | TBAF | Pd$_2$(dba)$_3$ | >98 | <2 |
| 3 | CsF | Pd$_2$(dba)$_3$ | >98 | 3 |
| 4 | KF | Pd$_2$(dba)$_3$ | 93 | 65 |
| 5 | KF | PdCl$_2$(dppf) | >98 | 48 |
| 6 | Et$_3$N[d] | Pd$_2$(dba)$_3$ | 42 | 58 |
| 7 | Et$_3$N[d] | PdCl$_2$(dppf) | 81 | 63 |
| 8 | Et$_3$N[d] | PdCl$_2$(dppf)[e] | >98 | 64 |

[a]Typical trials were carried out with 40 mg of 3 (0.98 mmol/g) and 2 (1.5 equiv, 58 mg, 1.07 mmol/g) with the indicated base (10 equiv) and catalyst (10 mol % Pd$_2$(dba)$_3$ or 20 mol % PdCl$_2$(dppf)) in DMF-ethylene glycol 10:1 (2.5 mL) at 105° C. for 20 h.
[b]Measured by $^1$H NMR integration of representative signals on crude reaction products.
[c]Non optimized yields of crude products after cleavage from the resin and drying in vacuo for >12 hours. The reported values are based on internal standardization.
[d]A large excess was used (0.25 mL).
[e]The catalyst was added in two portions, one at the start, one after 8 h.

Control experiments were devised to confirm the role and efficiency of ethylene glycol phase transfer agent. Referring to Scheme 2, FIG. 7, control experiments were devised to confirm the role and efficiency of ethylene glycol as phase transfer agent under anhydrous Method B. Resin-to-resin cross coupling of model substrates compound 2 and compound 3 in the absence of ethylene glycol gave largely incomplete transfer, as shown by a lower than 50% conversion to product 4 (treatment of resin 2 alone in hot anhydrous DMF/Et$_3$N (9:1, 105° C., 24 h) led to less than 25% leaching of the boronic acid). This confirmed the advantage of using the phase transfer agent. Ethylene glycol trans-esterified the resin-bound boronic acid within a time scale that minimized any rate-lowering of the cross-coupling. When resin 2 was treated for 0.5 h in a 8:1:1 mixture of DMF/triethylamine/ethylene glycol at 105° C., less than 10% of the boronic acid remained bound to DEAM-PS support.

Figure 8:
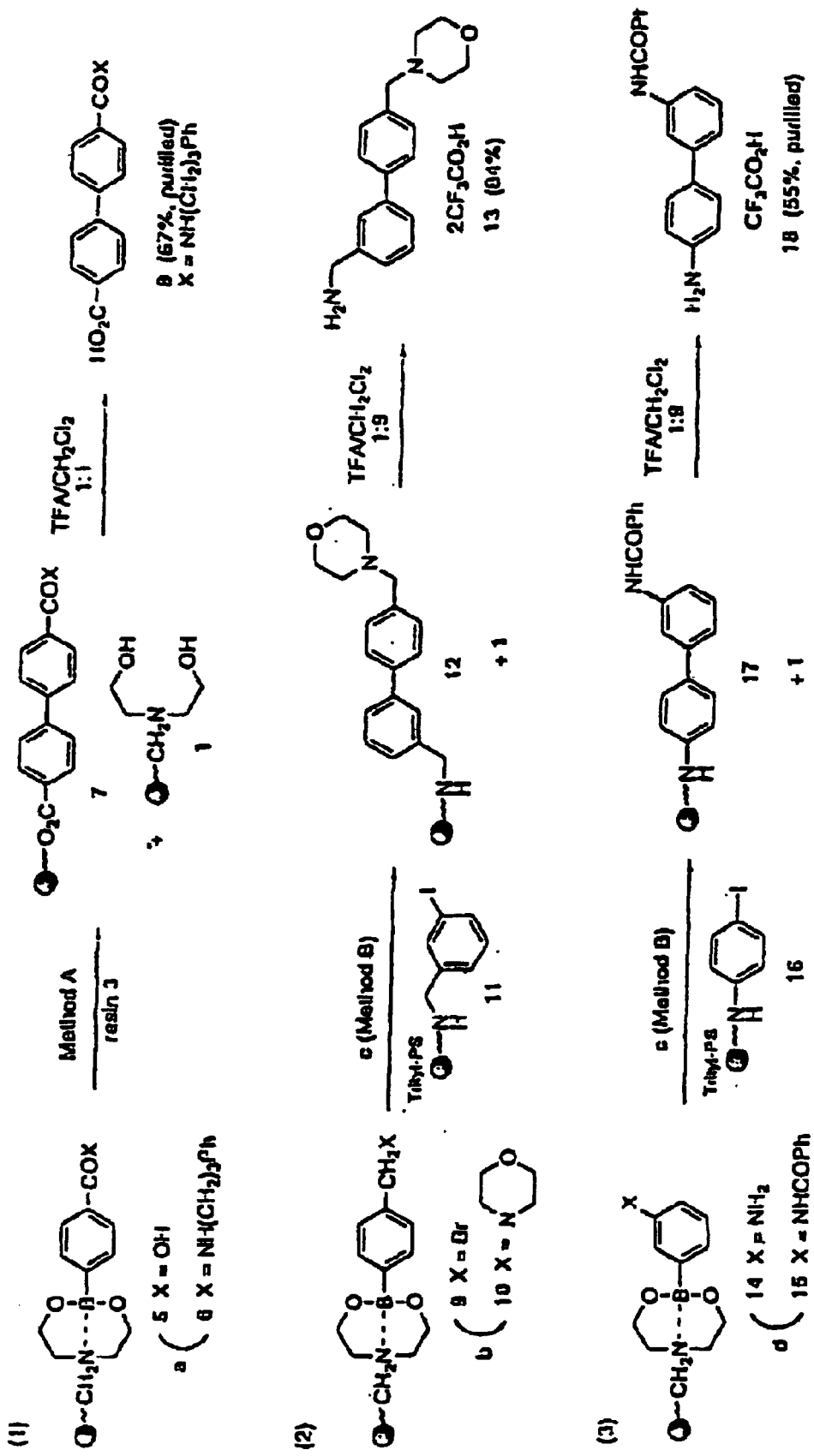
FIG. 8 is a schematic for "Method A" and "Method B," as described in detail in Example 3, below.

Resin-to-resin Suzuki coupling strategy to synthesize new arylboronic acids. Referring to FIG. 8, the usefulness of solid supports derivatized with dihydroxyalkylaminoalkyl groups (e.g. DEAM-PS) to synthesize new arylboronic acids and the potential of the methods of the invention incorporating resin-to-resin Suzuki coupling strategy was demonstrated by the convergent synthesis of unsymmetrically functionalized biphenyl compounds (schemes 1 to 3).

FIG. 8 is a schematic for "Method A" and "Method B": "reaction (a)" was Ph(CH$_2$)$_3$NH$_2$, DIC, HOBT, DMF, rt, 6 h; "reaction A)" was morpholine (10 equiv.), DMF, rt, 17 h; "reaction (c)" was a modified "Method B" using 6 equiv. compound 10 or compound 15, and K$_2$CO$_3$ (8 equiv.) in place of Et$_3$N, 115° C., 60 h; "reaction (d)" is PhCOCl (10 equiv.), (i-Pr)$_2$EtN (11 equiv.), THF, rt, 8 h.

Referring to Scheme 1, FIG. 8, amide derivative compound 6 was made from resin-bound p-carboxybenzeneboronic acid (compound 5) under standard carbodiimide methods, as described in, e.g., Hall (1999) Angew. Chem. Int. Ed. 38:3064–3067. The efficiency of this step was validated via cleavage of a resin sample (THF/AcOH/H$_2$O 90:5:5, 1 h), followed by characterization of the resulting boronic acid. Following washing and drying operations, resin 6 was reacted with compound 3 of FIG. 7 using method A (Scheme 1, FIG. 8), affording 4,4'-biphenyl dicarboxylic acid monoamide (compound 8, Scheme 1, FIG. 8) after cleavage from the resin mixture (resin 7, Scheme 1, FIG. 8, and resin 1, FIG. 7). These results demonstrate the effectiveness of a convergent RRTR strategy in solid-phase synthesis using solid supports derivatized with dihydroxyalkylaminoalkyl groups. Indeed, as p-carboxybenzeneboronic acid was inept as a substrate in Suzuki reactions; attempts to couple p-carboxybenzeneboronic acid to resin 3 (Scheme 2, FIG. 7) failed (similar results reported in Wendeborn (1998) Synlett 671–675). A linear solid-phase strategy involving p-carboxybenzeneboronic acid coupling to resin 3 of FIG. 7 followed by amide formation would be impracticable.

Referring to Scheme 2, FIG. 8, the methods of the invention (a Suzuki RRTR-based strategy) were also useful to afford monoalkylated biphenyl dibenzylamines. For example, DEAM-PS bound p-(bromomethyl)benzeneboronic acid (compound 9) was alkylated with morpholine to give compound 10 (the efficiency of this step was validated via cleavage of a resin sample (THF/AcOH/H$_2$O 90:5:5, 1 h), followed by characterization of the resulting boronic acid). Compound 10 was treated with trityl-PS bound m-iodobenzylamine (compound 11) under modified RRTR Method B (Scheme 2) (K$_2$CO$_3$ as base), and after cleavage of the resin mixture, afforded crude diamine compound 13 in 84% yield and high purity (>90% by HPLC). Again, with his example, a linear synthesis based on the cross-coupling of compound 11 with p-(bromomethyl)benzeneboronic acid would be hampered by incompatible reaction conditions. The basic conditions required in the Suzuki coupling could promote nucleophilic displacement on the benzylic bromide which in addition can react with palladium(0) by oxidative addition (see, e g., Tsuji, J. *Palladium Reagents and Catalysts*; Wiley: Chichester, UK, 1995).

Referring to Scheme 3, FIG. 8, monoacylated biphenyl dianilines were also synthesized efficiently. Cleavage and handling of the boronic acid prior to the Suzuki coupling was eliminated and there was no need for transferring the resin to a new reaction vessel after washing and drying operations. In addition, solid-phase immobilization circumvented the tendency of free boronic acids to dehydrate by forming anhydrides that are difficult to characterize and weight accurately. These advantages were very appealing toward combinatorial chemistry applications. For example, libraries of new solid supports derivatized with dihydroxyalkylaminoalkyl groups (e.g., DEAM-PS bound arylboronic acids) could be made and combined with libraries of supported haloarenes.

4'-(3-Phenyl-propylcarbamoyl)-biphenyl-4-carboxylic acid (8). Pale brown solid (96% yield by mass; 78% yield by $^1$H NMR with EtOAc int. std.): $^1$H NMR (300 MHz, CD$_3$OD) δ 8.10 (d, J=8 Hz, 2H), 7.90 (d, J=8 Hz, 2H), 7.78 (d, J=8 Hz, 2H), 7.77 (d, J=8 Hz, 2H), 7.29–7.13 (m, 5H), 3.44 (t, J=7 Hz, 2H), 2.71 (t, J=8 Hz, 2H), 1.96 (qn, J=8 Hz, 2H); $^{13}$C NMR (75 MHz, CD$_3$OD) δ 170.6, 169.9, 145.3, 144.4, 143.1, 135.2, 131.4, 129.5, 129.0, 128.3, 128.1, 126.9, 40.8, 34.4, 32.3 (the resolution of this $^{13}$C NMR was poor because of the limited solubility of the product in most commercial deuterated solvents); IR (microscope) 3400–2400, 3343, 3298, 3031, 2928, 1679, 1626 cm$^{-1}$; HRMS (ES, m/z) calcd for $C_{23}H_{21}NNaO_3$ (M+Na)$^+$ 382.1419. found 382.1418.

3-Iodobenzylamino trityl-PS resin (11). A solution of 3-iodobenzylamine (213 μL, 1.6 mmol) in 8 mL of CH$_2$Cl$_2$ was added to trityl chloride resin (500 mg, 0.40 mmol, theor. loading: 0.80 mmol g$^{-1}$) in pp vessel. The resulting suspension was shaken for 3 h, after which the resin was rinsed with CH$_2$Cl$_2$ (3×), 19:1 DMF/Et$_3$N (3×), MeOH (1×15 min.), CH$_2$Cl$_2$ (5×), and dried under high vacuum for >24 h, affording 545 mg of a white resin (theor.: 557 mg, 0.72 mmol g$^-$).

C-(4'-Morpholin-4-ylmethyl-biphenyl-3-yl)-methylamine (13). Brown oil (144% yield by mass; 82% yield by $^1$H NMR with EtOAc int. std.): $^1$H NMR (300 MHz, CD$_3$OD) δ 7.80–7.40 (m, 8H), 4.40 (s, 2H), 4.19 (s, 2H), 4.01 (br s, 2H), 3.76 (br s, 2H), 3.37 (br s, 2H), 3.23 (br s, 2H); $^{13}$C NMR (75 MHz, CD$_3$OD) δ 143.5, 142.1, 135.3, 133.1, 130.9, 129.5, 129.3, 128.9, 128.8, 128.7, 65.0, 61.6, 52.9, 44.3; IR (MeOH cast) 3300–2400, 2996, 1675, 1203, 1132 cm$^{-1}$; HRMS (ES, m/z) calcd for $C_{18}H_{23}N_2O$ (M+H)$^+$ 283.1805. found 283.1820.

4-Iodoanilino trityl-PS resin (16). A solution of 4-iodoaniline (360 mg, 1.6 mmol) in 8 mL of pyridine was added to trityl chloride resin (1.03 g, 0.82 mmol, theor. loading: 0.80 mmol g$^{-1}$) in a pp vessel. The resulting suspension was shaken for 3 days, after which the resin was rinsed with pyridine (4×), diethyl ether (5×), and dried under high vacuum for >24 h, affording 1.16 g of a white resin (theor.: 1.18 g, 0.70 mmol g$^{-1}$).

N-(4'-Amino-biphenyl-3-yl)-benzamide (18). Brown solid (81% yield by mass; 55% yield by $^1$H NMR with EtOAc int. std.): $^1$H NMR (300 MHz, CD$_3$OD) δ 8.07 (s, 1H), 7.95 (d, J=7 Hz, 2H), 7.77 (d, J=8 Hz, 2H), 7.68–7.34 (m, 8H); $^{13}$C NMR (75 MHz, CD$_3$OD) δ 169.0, 141.9, 140.5, 136.2, 135.5, 133.0, 130.4, 129.7, 129.5, 128.6, 124.0, 122.7, 121.4, 120.7; IR (MeOH cast) 3500–2400, 2917, 2624, 1673, 1202 cm$^{-1}$; HRMS (ES, m/z) calcd for $C_{19}H_{17}N_2O$ (M+H)$^+$ 289.1335. found 289.1338.

Figure 9:
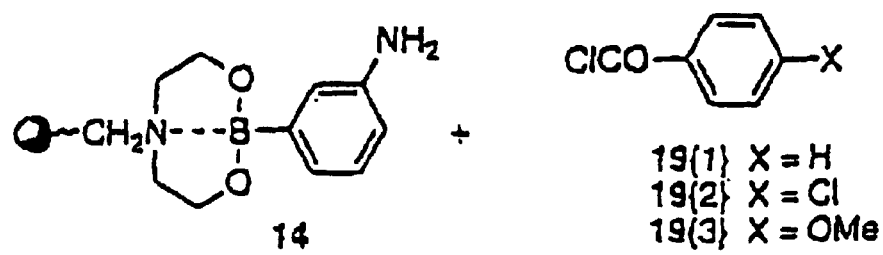
FIG. 9 is a schematic of a library of biphenyl compounds synthesized using the methods of the invention with a commercial, semi-automated parallel synthesizer as described in detail in Example 3, below.
Figure 9:
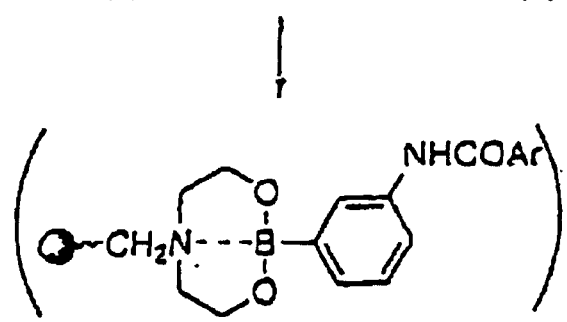
Figure 9:
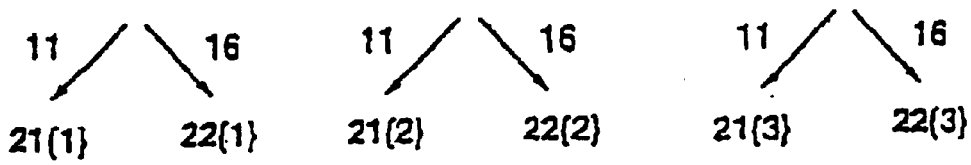

Libraries of new solid supports derivatized with dihydroxyalkylaminoalkyl groups. Referring now to FIG. 9, a model library of biphenyl compounds was made using the methods of the invention with a commercial, semi-automated parallel synthesizer. A Quest 210™ instrument with solvent wash unit was employed (Argonaut Technologies, San Carlos, Calif.). Cleavage was effected on-line and crude products were obtained after evaporation of solvents. Yields and purity were estimated by comparison with an internal NMR standard.

Supported boronic acids compound 20 {1}, compound 20{2} and compound 20{3} were synthesized from compound 14 and acid chlorides, compound 19{1}, compound 19{2} and compound 19{3}. After resin rinsing, these acid chlorides were immediately reacted with iodoarene resins compound 11 and compound 16 using the same conditions used for the synthesis of compound 18 (FIG. 8). After on-line cleavage, all six biphenyl products compound 21{1}, compound 21{2} and compound 21{3} and compound 22{1}, compound 22{2} and compound 22{3} were obtained in excellent yields (75–100%) and high purity (>90% by NMR). In one embodiment, reactions performed with the synthesizer were significantly more efficient and cleaner compared to the manual protocol using glass vessels. This was shown by comparing spectra of reference library member 22{1} with another sample made previously via manual synthesis.

Example 4

Examination of the Role of the Nitrogen in Dihydroxyalkylaminoalkyl-Conjugated Resins.

Figure 10:
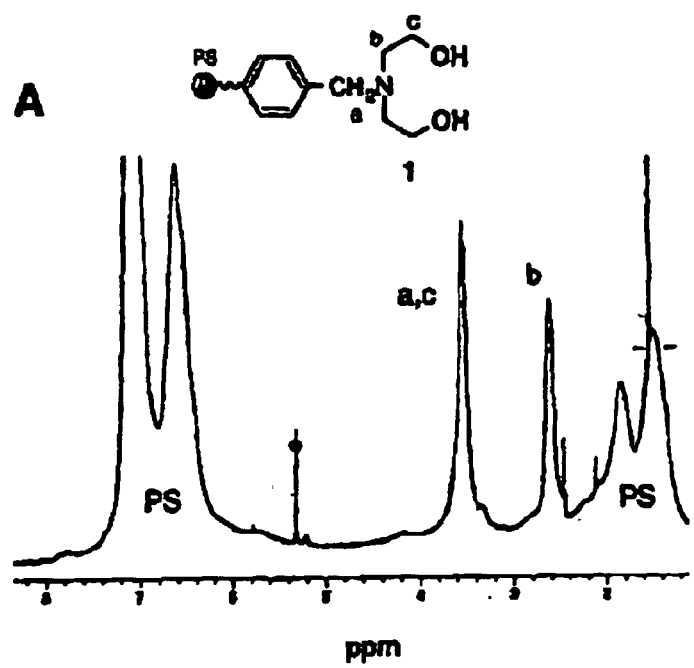
FIG. 10 is a Gel-phase $^1$H NMR spectra (500 MHz) of DEAM-PS (A) and DEAM-PS supported p-tolylboronic acid (B) using a Varian magic angle spinning nanoprobe. Solvent is $CD_2Cl_2$ (peak identified by a dot) as described in detail in Example 4.
Figure 10:
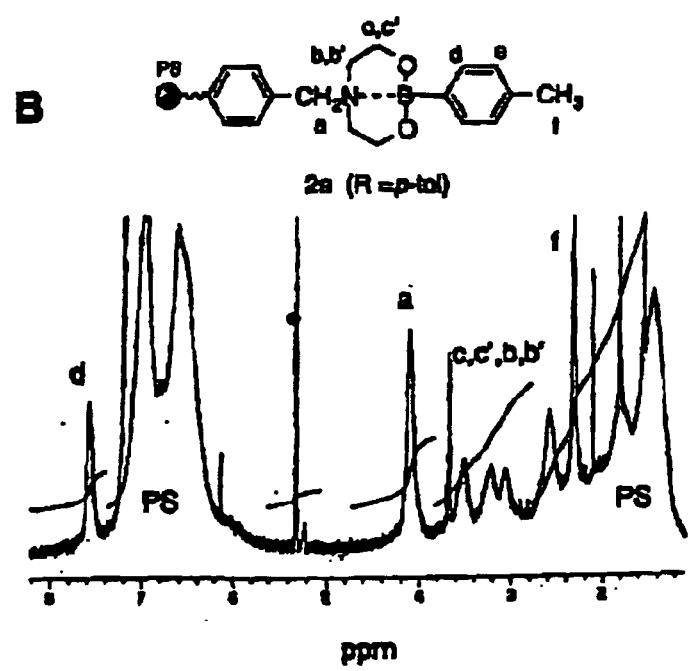

Referring now to FIG. 10, FIG. 10A shows the Gel-phase $^1$H NMR spectra (500 MHz) of the free form of DEAM-PS, while FIG. 10B shows the NMR spectra of the p-tolylboronic acid conjugated form using a Varian magic angle spinning nanoprobe. Solvent was CD$_2$Cl$_2$ (peak identified by a dot). Conditions: A; at=3, pw=2.5, d1=0, spinning @ 2119 Hz. B; at=3, pw=2.0, d1=0, spinning @ 2300 Hz (Note: signal at 3.7 ppm is residual THF). PS: polystyrene resonances.

By making abstraction of peaks from the polystyrene matrix, two broad singlets showed up at 2.6 and 3.5 ppm in the spectrum of free DEAM-PS (A). The largest most unshielded peak contained resonances from both benzylamino and hydroxymethyl methylenes. Upon formation of a cis fused bicyclic diethanolamine boronate adduct whose two faces are non-equivalent, the ring hydrogens became diastereotopic. As expected, the resulting spectrum (B) showed extensive degeneration of the methylenic protons in the hydroxyethyl arms. As many as four peaks were seen between 2.2 and 3.6 ppm, thereby lending support to a tetrahedral, nitrogen-coordinated boronic ester.

Example 5

UV Spectroscopic Studies Conducted on the Cleavage of p-tolylboronic Acid from DEAM-PS (1).

Figure 11:
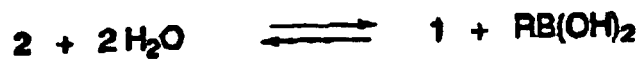
FIG. 11 is an equation relating to the boronate exchange process as described in detail in Example 5.

To investigate the extent to which the diethanolamine boronate linkage was sensitive to water, UV spectroscopic assay were carried out, whereby the hydrolysis of DEAM-PS-supported p-tolylboronic acid (compound 2) was monitored quantitatively both in a time related fashion, and with respect to the amount of water used. In principle, a minimum of two molar equivalents of water was required to effect quantitative cleavage of the compound. This type of boronate exchange process involving water and a competing diol like DEAM-PS (compound 1), however, is usually under equilibrium as detailed in FIG. 11.

Figure 12:
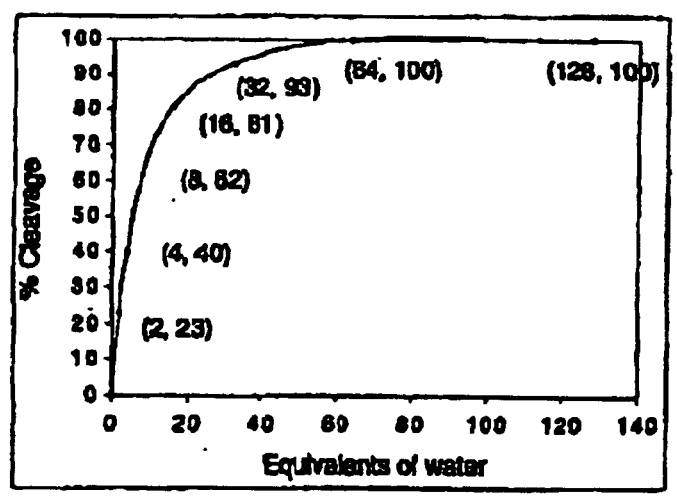
FIG. 12 is a graph relating the percentage of hydrolytic cleavage of DEAM-PS supported p-tolylboronic acid followed by UV spectroscopy (225 nm) as a function of water stoichiometry as described in detail in Example 5.

Referring now to FIG. 12, a time profile of boronic acid release with variable amounts of water showed that the extent of boronic acid release rapidly reached a plateau within less than one minute (data not shown). A comparison of the percentage of boronic acid release with different number of equivalents of water is shown.

A calibration graph (absorbance at 225 nm vs concentration (M)) was made using p-tolylboronic acid. DEAM-PS supported p-tolylboronic acid (2a) (330 mg, 0.278 mmol, obs. loading: 0.842 mmol g$^{-1}$) was weighed into a 20 mL pp reaction vessel and swollen in dry THF (5 mL). A 50 µL aliquot was diluted to 25 mL with dry THF for UV analysis. Then resin 2a was cleaved with a sequential addition of water. First, H$_2$O (10 µL, 2 equiv) was added and the pp vessel was shaken for 1 min and a 50 µL aliquot was diluted to 25 mL with dry THF for UV analysis. Next, the previous sequence was repeated for 4 (20 µL total), 8 (40 µL total), 16 (80 µL total), 32 (160 µL total), 64 (320 µL total) and 128 (640 µL total) equivalents of water. Overall, the resulting data confirmed that hydrolysis was under equilibrium and that a large excess of water (>32 equivalents) was required in order to provide a practically quantitative hydrolysis.

In one preferred embodiment, such a quantity of water corresponded roughly to the use of 10 mL of cleavage solution (5% water/THF) per gram of resin at a 0.8 mmol/g resin loading. This relationship, however, may not be generalized to all types of functionalized boronic acids. In particular, some ortho-substituted arylboronic acids may behave differently and prove more difficult to liberate from DEAM-PS. In one preferred embodiment, a larger proportion of water or the use of acidic conditions (THF/H$_2$O/AcOH 90:5:5) may be used.

The above hydrolysis study also suggested that the reverse process—boronic acid immobilization from DEAM-PS—by releasing 2 molar equivalents of water cannot be quantitative in THF unless a large excess of boronic acid is employed to shift the equilibrium. Otherwise, according to FIG. 12, the approximate maximum yield of immobilization for equimolar amounts of DEAM-PS and boronic acid was 80%. Thus, in one preferred embodiment, in order to optimize the yield of immobilization, the latter must be largely monodehydrated before use (although commercial boronic acids tend to come as largely dehydrated anhydride forms, in a preferred embodiment, they may be further dried in vacuo prior to immobilization with DEAM-PS; for a pertinent review, see: Lappert, M. F. Chem. Rev. 1956, 56, 959).

Example 6

Preparation and Use of Diisobutanolaminomethyl Polystyrene Substituted Resin

Figure 14:
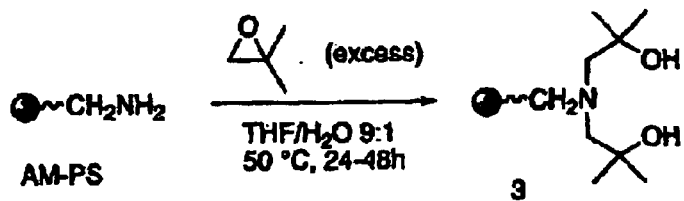
FIG. 14 is a schematic summarizing the production of diisobutanolaminomethyl substituted polystyrene substituted resin from isobutylene oxide as described in detail in Example 6.

Referring now to FIG. 14, diisobutanolaminomethyl polystyrene substituted resin (compound 3) was made from isobutylene oxide by a procedure similar to that in Example 1 for the production of DEAM-PS. 1% Divinylbenzene (DVB) cross-linked aminomethylated polystyrene (AM-PS) was derivatized with a diisobutanolamine anchor through the reaction of aminomethylated polystyrene (AM-PS) with excess isobutylene oxide at 50° C. in a 9:1 tetrahydrofuran (THF)/water solvent mixture using a sealed, pressure-resistant tube. Reaction time was 24–48 hours. In another embodiment, reaction time was 72 hours.

Immobilization and cleavage of p-tolylboronic acid from resin 3, showed similar results to that for DEAM-PS when carried out under similar conditions.

Examples 7–11

Solid-Phase Derivatization of Functionalized Boronic Acids

Referring now to FIGS. 15–23 and Tables 6–10 in Example 7–11, a series of solid-phase reaction protocols to derivatize functionalized, DEAM-PS-supported boronic acids are described.

In principle, the use of dihydroalkylamino-conjugated resins of the present invention, including DEAM-PS, are not limited to the procedures described herein and many other types of transformations could be envisaged. These examples clearly demonstrate that multistep transformations can be carried out with high efficiency. Synthetic schemes such as these ones could be employed to rapidly assemble two-dimensional combinatorial libraries of new boronic acids for biological screening or as building blocks for subsequent reactions. Obviously, several other types of transformations could be envisaged. All these reactions could be performed easily on gram scale or larger especially with the use of the high loading resins of the present invention, e.g., DEAM-PS. The use of use of dihydroalkylamino- and dihydroxyalkylaminobenzyl-conjugated resins of the present invention, including DEAM-PS, for solid-phase derivatization of functionalized boronic acids is also advantageous for handling and storage purposes. Indeed, boronic acids can be protected against slow air oxidation through immobilization as solid support adducts.

In the following examples, all supported substrates were easily prepared in high yield from DEAM-PS as described in protocols in the previous examples. Most boronic acid products obtained after cleavage with 5% water/THF were not further purified and were characterized by mass spectrometry, IR, and $^1$H and $^{13}$C NMR spectroscopy. The reported yields of products were inclusive of the boronic acid immobilization step may not be quantitative (Woods, W. G.; Bengelsdorf, I. S.; Hunter, D. L. J. Org. Chem. 1966, 31, 2766–2768). Percentage yields were calculated as an average value of mass balance and internal standardization with ethyl acetate as compared with the theoretical loading of free DEAM-PS resin. These two methods were almost always found to be within a 5% range using optimized analytical methods. The indicated purity values for the products was a conservative estimate based on inspection of NMR spectra and quantitation of peaks from the expected product relative to unknown signals from possible by-products and starting material. In general, all compounds were obtained with a minimum of 90% purity, and in a majority of cases there were no detectable by-products by NMR analysis.

Example 7

Figure 15:
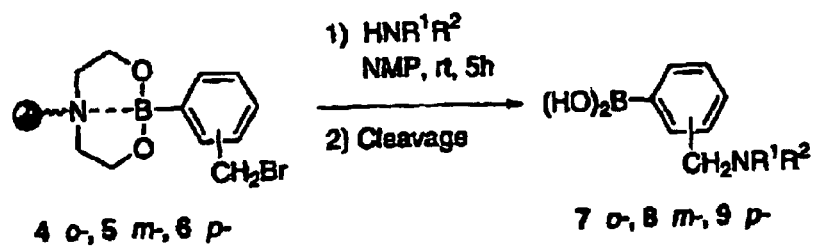
FIG. 15 is a schematic summarizing the substitution reactions of bromomethyl derivatized benzeneboronic acids with primary and secondary amines as describes in detail in Example 7.

Substitution of Bromomethyl Derivatized Benzeneboronic Acids with Representative Primary and Secondary Amines Table 6 summarizes the results for the substitution of bromomethyl derivatized benzeneboronic acids with representative primary and secondary amines shown in FIG. 15. In this example involving amphoteric aminomethyl-substituted products, the advantages of a solid-phase approach towards product isolation were optimal vis-a-vis solution-phase methods. In one preferred embodiment, suitable conditions found from alkylations of meta and para substrates 5 and 6 involved simple stirring of DEAM-PS supported bromomethylbenzeneboronic acid with the amine in NMP for approximately 5 hours at room temperature. In one preferred embodiment, as much as 10 equivalents of secondary amines were employed to ensure reaction completion under these conditions. In order to suppress cross-linking by double alkylation with primary amines, in one embodiment it was found preferable to use a low loading DEAM-PS resin (<0.60 mmol/g) with a larger excess of the amine (50 equiv). Due to the large excess of primary amine reactant, the yields of the secondary amine products could be diminished from premature cleavage of the supported boronic acid. Nonetheless, these protocols provided good to excellent yields of isolated secondary and tertiary amine products 8 and 9.

Figure 20:
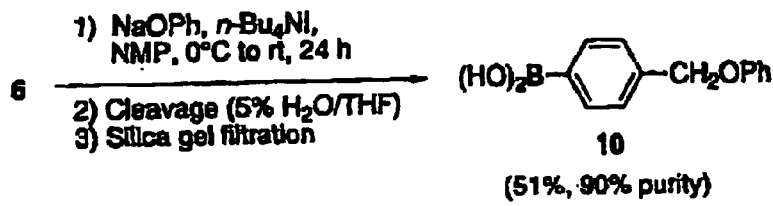
FIG. 20 is a schematic of the reaction of DEAM-PS supported p-substituted bromomethyl derivatized benzeneboronic acid with sodium phenoxide s as described in detail in Example 7.

Referring now to FIG. 20, Sodium phenoxide was used as an example of an oxygen-based nucleophile. Treatment of 6 (FIG. 15) with PhONa in the presence of iodide ion in NMP for 24 hours provided ether 10 of FIG. 20 in moderate yield after cleavage from the resin followed by rapid filtration through silica gel.

TABLE 6

Substitution reactions on 5 and 6 (FIG. 15).

| Entry | Substrate | Conditions[a] | Product {R[1], R[2]} | Yield[b] (%) | Purity[c] (%) |
|---|---|---|---|---|---|
| 1 | 5 | A | 8a {H, CH$_2$Ph} | 69 | 95 |
| 2 | 5 | A | 8b {H, CH$_2$CH(CH$_3$)$_2$} | 50 | >90 |
| 3 | 5 | B | 8c {(CH$_2$)$_2$O(CH$_2$)$_2$} | 85 | 95 |
| 4 | 5 | B | 8d {Me, CH$_2$Ph} | 75 | >95 |
| 5 | 6 | A | 9a {H, CH$_2$Ph} | 69 | >90 |
| 6 | 6 | A | 9b {H, CH$_2$CH(CH$_3$)$_2$} | 53 | 95 |
| 7 | 6 | B | 9c {(CH$_2$)$_2$O(CH$_2$)$_2$} | 98 | >90 |
| 8 | 6 | B | 9d {Me, CH$_2$Ph} | 94 | 95 |

[a]Reactions were carried out by shaking the supported benzyl bromide with the amine in NMP at rt for approx. 5 hours (typical scale 0.12 mmol 5–6). Conditions: A: 50 equiv of primary amine, use of low loading DEAM-PS resin (0.60 mmol/g). B: 10 equiv of secondary amine, use of either low loading (0.60 mmol/g) or high loading (1.14 mmol/g) DEAM-PS resin.
[b]Non optimized yields of crude products after cleavage from the resin with 5% H$_2$O/THF and drying in vacuo for >12 hours. The reported values are an average of mass balance and internal standardization.
[c]Estimated from $^1$H and $^{13}$C NMR data.

Typical procedure for substitution of a DEAM-PS supported bromomethyl-substituted arylboronic acid: Preparation of 3-(benzylaminomethyl)phenylboronic acid (8a). The DEAM-PS resin (200 mg, 0.120 mmol, theor. loading: 0.60 mmol g$^{-1}$), and 3-bromomethylphenyl boronic acid (34 mg, 0.16 mmol) were weighed into a 10 mL polypropylene (pp) reaction vessel. Dry CH$_2$Cl$_2$ (2 mL) was added and the reaction suspension was shaken for 1 h and 40 min at rt. The pp vessel was drained, and the resin was washed with dry CH$_2$Cl$_2$ (3×, 2 mL). The resin was then swollen in dry NMP (2 mL), and benzylamine (0.655 mL, 6.0 mmol) was added. The reaction vessel was shaken for 5 h, then drained and the resin was washed successively with dry DMF (3×), dry CH$_2$Cl$_2$ (5×), and dry THF (5×). The product was then cleaved from the resin by vortexing the resin using the typical procedure described above (5% H$_2$O/THF for 20 min). The product containing solution was drained and the resin was washed with 5% H$_2$O/THF (3×). The product filtrates were combined, concentrated under reduced pressure and dried under high vacuum overnight to afford a white solid (19 mg, 70% yield by mass; 67% yield by $^1$H NMR with EtOAc int. std.): $^1$H NMR (300 MHz, 5% D$_2$O in CD$_3$OD) δ 7.66 (m, 2H), 7.36–7.30 (m, 7H), 3.84 (s, 2H), 3.83 (s, 2H); $^{13}$C NMR (75 MHz, 5% D$_2$O in CD$_3$OD) δ 135.6, 135.2, 134.2, 131.0, 129.9, 129.7, 129.2, 128.8, 128.7, 53.5, 53.1; IR (CH$_2$Cl$_2$ cast) 3360, 3029, 2925, 2852, 1652, 1602 cm$^{-1}$; HRMS (ES, m/z) calcd for C$_{14}$H$_{17}$BNO$_2$ (M+H)$^+$ 242.1347. found 242.1350.

3-(iso-Butylaminomethyl)phenylboronic acid (8b). White solid (52% yield by mass; 48% yield by $^1$H NMR with EtOAc int. std.): $^1$H NMR (300 MHz, 5% D$_2$O in CD$_3$OD) δ 7.62–7.61 (m, 2H), 7.29–7.28 (m, 2H), 3.94 (s, 2H), 2.62 (d, J=6 Hz, 2H), 1.91 (nonet, J=6 Hz, 7 Hz, 1H), 0.95 (d, J=7 Hz, 6H); $^{13}$C NMR (75 MHz, 5% D$_2$O in CD$_3$OD) δ 135.7, 135.3, 134.6, 130.3, 128.6, 56.6, 54.1, 28.1, 20.7; IR (CH$_2$Cl$_2$ cast) 3259, 3046, 2956, 2871, 1665, 1602 cm$^{-1}$; HRMS (ES m/z) calcd for C$_{11}$H$_{19}$BNO$_2$ (M+H)$^+$ 208.1503. found 208.1501.

3-(Morpholinomethyl)phenylboronic acid (8c). White solid (81% yield by mass; 90% yield by $^1$H NMR with EtOAc int. std.); $^1$H NMR (300 MHz, 5% D$_2$O in CD$_3$OD) δ 7.69–7.64 (m, 2H), 7.39–7.36 (m, 1H), 7.32–7.27 (m, 1H), 3.68 (m, 4H), 3.53 (s, 2H), 2.47 (m, 4H); $^{13}$C NMR (75 MHz, 5% D$_2$O in CD$_3$OD) δ 141.1, 136.7, 136.4, 134.1, 132.8, 128.6, 67.5, 64.4, 54.5; IR (CH$_2$Cl$_2$ cast) 3405, 3047, 2957, 2857, 2808, 1652, 1602 cm$^{-1}$; HRMS (ES, m/z) calcd for C$_{11}$H$_{17}$BNO$_3$ (M+H)$^+$ 222.1296. found 222.1297.

N-Methyl-3-(benzylaminomethyl)phenylboronic acid (8d). White solid (73% yield by mass; 77% yield by $^1$H NMR with EtOAc int. std.): $^1$H NMR (300 MHz, 5% D$_2$O in CD$_3$OD) δ 7.69–7.64 (m, 2H), 7.36–7.27 (m, 7H), 3.56 (s, 4H), 2.18 (s, 3H); $^{13}$C NMR (75 MHz, 5% D$_2$O in CD$_3$OD) δ 138.7, 137.6, 136.2, 134.1, 132.4, 130.7, 129.4, 128.6, 128.5, 62.7, 62.5, 42.1; IR (CH$_2$Cl$_2$ cast) 3405, 3028, 2942, 2835, 2785, 1601 cm$^{-1}$; HRMS (ES, m/z) calcd for C$_{15}$H$_{19}$BNO$_2$ (M+H)$^+$ 256.1503. found 256.1506.

4-(Benzylaminomethyl)phenylboronic acid (9a). White solid (69% yield by mass; 69% yield by $^1$H NMR with EtOAc int. std.): $^1$H NMR (300 MHz, 5% D$_2$O in CD$_3$OD) δ 7.72 (d, J=8 Hz, 2H), 7.36–7.30 (m, 7H), 3.84 (s, 4H); $^{13}$C NMR (75 MHz, 5% D$_2$O in CD$_3$OD) δ 138.3, 135.2, 131.7, 130.0, 129.7, 129.0, 128.9, 53.1; IR (CH$_2$Cl$_2$ cast) 3396, 3028, 2925, 2819, 1608 cm$^{-1}$; HRMS (ES, m/z) calcd for C$_{14}$H$_{17}$BNO$_2$ (M+H)$^+$ 242.1347. found 242.1344.

4-(iso-Butylaminomethyl)phenylboronic acid (9b). White solid (52% yield by mass; 53% yield by $^1$H NMR with EtOAc int. std.): $^1$H NMR (300 MHz, 5% D$_2$O in CD$_3$OD) δ 7.70 (d, J=8 Hz, 2H), 7.32 (d, J=8 Hz, 2H), 3.93 (s, 2H), 2.60 (d, J=7 Hz, 2H), 1.90 (nonet, J=6 Hz, 7 Hz, 1H), 0.95 (d, J=7 Hz, 6H); $^{13}$C NMR (75 MHz, 5% D$_2$O in CD$_3$OD) δ 135.2 134.9, 134.7, 129.1, 56.6, 53.7, 28.0, 20.7; IR (CH$_2$Cl$_2$ cast) 3432, 2957, 2872, 2823, 1660, 1610 cm$^{-1}$; HRMS (ES, m/z) calcd for C$_{11}$H$_{19}$BNO$_2$ (M+H)$^+$ 208.1503. found 208.1506.

4-(Morpholinomethyl)phenylboronic acid (9c). White solid (88% yield by mass): $^1$H NMR (300 MHz, 5% D$_2$O in CD$_3$OD) δ 7.72 (d, J=8 Hz, 2H), 7.32 (d, J=8 Hz, 2H), 3.70 (m, 4H), 3.34 (s, 2H), 2.55 (t, J=5 Hz, 4H); $^{13}$C NMR (75 MHz, 5% D$_2$O in CD$_3$OD) δ 138.8, 135.1, 130.1, 67.3, 64.0, 54.3; IR (CH$_2$Cl$_2$ cast) 3406, 2957, 2859, 2811, 1657, 1609 cm$^{-1}$; HRMS (ES, m/z) calcd for C$_{11}$H$_{17}$BNO$_3$ (M+H)$^+$ 222.1296. found 222.1294.

4-(Benzylaminomethyl)phenylboronic acid (9d). White solid (89% yield by mass; 99% yield by $^1$H NMR with 2,5-dimethylfuran int. std.): $^1$H NMR (300 MHz, 5% D$_2$O in CD$_3$OD) δ 7.73 (d, J=8 Hz, 2H), 7.35–7.31 (m, 7H), 3.64 (s, 4H), 2.24 (s, 3H); $^{13}$C NMR (100 MHz, 5% D$_2$O in CD$_3$OD) δ 137.9, 135.1, 134.8, 130.8, 129.9, 129.5, 128.9, 62.3, 62.3, 41.9; IR (CH$_2$Cl$_2$ cast) 3408, 3027, 2927, 2838, 2787, 1609 cm$^{-1}$; HRMS (ES, m/z) calcd for C$_{15}$H$_{19}$BNO$_2$ (M+H)$^+$ 256.1503. found 256.1504.

Preparation of 4-(Phenoxymethyl)phenylboronic acid (10). Phenol (41 mg, 0.437 mmol) was weighed into a round bottom flask and dissolved in dry NMP (1.5 mL). NaH (18 mg, 0.728 mmol) was added at 0° C. and the suspension was stirred for 30 min. Resin 6 (325 mg, 0.291 mmol, theor.

loading 0.895 mmol g$^{-1}$) was weighed into a 20 mL pp vessel and swollen in NMP (4 mL). The PhONa suspension was added to the resin followed by nBu$_4$NI (54 mg, 0.146 mmol) and the reaction was shaken for 24 h at rt. The reaction suspension was drained and the resin was rinsed with DMF (3×, 4 mL), THF (3×, 4 mL) and CH$_2$Cl$_2$ (3×, 4 mL). The product was cleaved from the resin using standard conditions and the combined filtrates were concentrated. Filtration of the product through a pad of silica gel using 10% MeOH/CH$_2$Cl$_2$ followed by concentration yielded a white solid (37 mg, 61% yield by mass; 42% yield by $^1$H NMR with EtOAc int. std.): $^1$H NMR (300 MHz, 5% D$_2$O in CD$_3$OD) δ; 7.73 (br d, J=8 Hz, 2H), 7.40–7.37 (d, J=8.0 Hz, 2H), 7.27–7.21 (m, 2H), 6.98–6.88 (m, 3H), 5.06 (s, 2H); $^{13}$C NMR (75 MHz, 5% D$_2$O in CD$_3$OD) δ 164.9, 145.5, 139.8, 135.3, 132.4, 126.8, 120.7, 75.7; IR (microscope) 3427, 3039, 2920, 2869, 1612, 1598 cm$^{-1}$; LRMS (ES, m/z, negative mode with NH$_4$F postcolumn) 249 (M+F)$^-$.

Example 8

Figure 16:
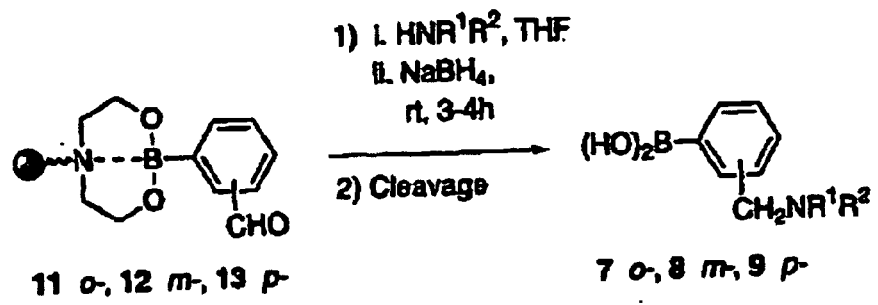
FIG. 16 is a schematic summarizing the reductive amination of supported formyl-substituted benzeneboronic acids with various primary and secondary amines as described in detail in Example 8.

Reductive Amination of Supported Formyl-Substituted Benzeneboronic Acids with Various Primary and Secondary Amines Referring now to Table 7, the results for the reductive amination of supported formyl-substituted benzeneboronic acids with various primary and secondary amines shown in FIG. 16 are described.

In one preferred embodiment, conditions involved preformation of the imine in THF, followed by addition of sodium borohydride as hydride source. In on embodiment, NaBHOAc$_3$, and NaBH$_3$CN led to premature cleavage of the supported boronic acid under these conditions. The ortho substrate 11 was observed to give the most satisfactory yields of products 7 with a good purity. This chemistry thus complements the bromomethyl substitution method described above. In one embodiment the less hindered meta and para substrates 12 and 13 gave the respective amine products 8 and 9 in lower purities. There was no evidence for double alkylation in the case of primary amines.

TABLE 7

Reductive amination on aldehyde 11 (FIG. 16).

| Entry | Substrate | Conditions[a] | Product {R$^1$, R$^2$} | Yield[b] (%) | Purity[c] (%) |
|---|---|---|---|---|---|
| 1 | 11 | A | 7a {H, CH$_2$Ph} | 66 | >90 |
| 2 | 11 | A | 7b {H, CH$_2$CH(CH$_3$)$_2$} | 55 | >90 |
| 3 | 11 | A | 7c {H, (CH$_2$)$_3$Ph} | 62 | 95 |
| 4 | 11 | A | 7d {H, (CH$_2$)$_3$CH$_3$} | 73 | >95 |

[a]Typical scale 0.1 mmol. A: Reactions were carried out by preforming the imine from supported aldehyde and the amine (2 equiv) in THF at rt for approx. 2.5 hours. Sodium borohydride was added and the suspension was shaken for approx. 4 hours.
[b]Non optimized yields of crude products after cleavage from the resin with 5% H$_2$O/THF and drying in vacuo for >12 hours. The reported values are an average of mass balance and internal standardization.
[c]Estimated from $^1$H and $^{13}$C NMR data.

Typical procedure for reductive amination of a DEAM-PS supported formyl-substituted arylboronic acid: Preparation of 2-(benzylaminomethyl)phenylboronic acid (7a). DEAM-PS resin (100 mg, 0.114 mmol, theor. loading: 1.14 mmol g$^{-1}$) and 2-formylphenylboronic acid (23 mg, 0.15 mmol), were weighed into a pp reaction vessel. Dry CH$_2$Cl$_2$ (2 mL) was added, and the reaction suspension was shaken for 1 h and 45 min. The pp vessel was then drained, and the resin washed with dry CH$_2$Cl$_2$ (3×). The resin was swollen in dry THF (2 mL), and benzylamine (25 μL, 0.23 mmol) was added. The reaction vessel was shaken for 2.5 h, then NaBH$_4$ (18 mg, 0.46 mmol) was added, and the vessel was shaken for an additional 3 h and 45 min. The pp vessel was drained, and the resin was washed successively with dry DMF (3×), dry CH$_2$Cl$_2$ (5×), and dry THF (5×). The product was then cleaved from the resin using the typical procedure described above (5% H$_2$O/THF, 2 mL for 20 min). The product-containing solution was drained and the resin was washed with 5% H$_2$O/THF (3×, 2 mL). The product filtrates were combined, concentrated under reduced pressure and dried under high vacuum overnight to afford a white solid (71% yield by mass; 60% yield by $^1$H NMR with 2,5-dimethylfuran int. std.): $^1$H NMR (300 MHz, 5% D$_2$O in CD$_3$OD) δ 7.47–7.31 (m, 6H), 7.21–7.14 (m, 2H), 7.08–7.05 (m, 1H), 3.98 (s, 2H), 3.85 (s, 2H); $^{13}$C NMR (125 MHz, 5% D$_2$O in CD$_3$OD) δ 142.4, 136.2, 131.6, 130.8, 129.9, 129.6, 129.5, 128.3, 127.7, 124.2, 54.1, 51.1; IR (CH$_2$Cl$_2$ cast) 3300, 3060, 3028, 3004, 2923, 2870, 1454 cm$^{-1}$; HRMS (ES, m/z) calcd for C$_{14}$H$_{17}$BNO$_2$ (M+H)$^+$ 242.1347. found 242.1344.

2-(iso-Butylaminomethyl)phenylboronic acid (7b). White solid (57% yield by mass); $^1$H NMR (300 MHz, 5% D$_2$O in CD$_3$OD) δ 7.47–7.44 (m, 1H), 7.21–7.12 (m, 3H), 4.02 (s, 2H), 2.70 (d, J=7 Hz, 2H), 2.10 (tq, J=6 Hz, 7 Hz, 1H), 1.02 (d, J=7 Hz, 6H); $^{13}$C NMR (125 MHz, 5% D$_2$O in CD$_3$OD) δ 132.0, 128.2, 127.7, 124.0, 56.5, 55.4, 26.9, 20.9; IR (CH$_2$Cl$_2$ cast) 3301, 3090, 2956, 2926, 2869, 1443 cm$^{-1}$, HRMS (ES, m/z) calcd for C$_{11}$H$_{19}$BNO$_2$ (M+H)$^+$ 208.1503. found 208.1503.

2-((3'-Phenyl-propylamino)methyl)phenylboronic acid (7c). White solid (62% yield by mass; 62% yield by $^1$H NMR with 2,5-dimethylfuran int. std.): $^1$H NMR (300 MHz 5% D$_2$O in CD$_3$OD) δ 7.43–7.41 (m, 1H), 7.30–7.13 (m, 8H), 3.98 (s, 2H), 2.88 (m, 2H), 2.70 (t, J=8 Hz, 2H), 2.05 (qn, J=8 Hz, 2H); $^{13}$C NMR (75 MHz, 5% D$_2$O in CD$_3$OD): δ 142.5, 131.5, 129.5, 129.4, 128.3, 127.7, 127.1, 124.0, 54.9, 34.4, 29.7; IR (CH$_2$Cl$_2$ cast) 3230, 3058, 3026, 2917, 2849, 1495 cm$^{-1}$; HRMS (ES, m/z) calcd for C$_{16}$H$_{21}$BNO$_2$ (M+H)$^+$ 270.1660. found 270.1656.

2-(n-Butylaminomethyl)phenylboronic acid (7d). White solid (75% yield by mass; 71% yield by $^1$H NMR with EtOAc int. std.): $^1$H NMR (300 MHz, 5% D$_2$O in CD$_3$OD) δ 7.45–7.42 (m, 1H), 7.20–7.14 (m, 3H), 4.00 (s, 2H), 2.86 (t, J=8 Hz, 2H), 1.71 (qn, J=8 Hz, 2H), 1.41 (sx, J=8 Hz, 2H), 0.99 (t, J=8 Hz, 3H); $^{13}$C NMR (75 MHz, 5% D$_2$O in CD$_3$OD) δ 142.5, 131.5, 128.2, 127.7, 124.1, 54.9, 30.1, 21.4, 14.1; IR (CH$_2$Cl$_2$ cast) 3310, 3233, 3057, 3005, 2958, 2930, 2872, 1598 cm$^{-1}$; HRMS (ES, m/z) calcd for C$_{11}$H$_{19}$BNO$_2$ (M+H)$^+$ 208.1503. found 208.1508.

Example 9

Figure 17:
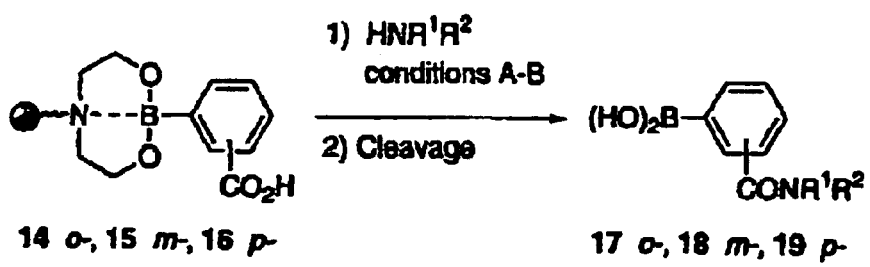
FIG. 17 is a schematic summarizing the formation of amide derivatives from DEAM-PS supported carboxy-functionalized arylboronic acids as described in detail in Example 9.

Amide Derivatives from DEAM-PS Supported Carboxy-Functionalized Arylboronic Acids Referring now to Table 8 and FIG. 17, the formation of amide derivatives from DEAM-PS supported carboxy-functionalized arylboronic acids was explored. In the schematic shown in FIG. 17, the reaction proved to be very general with respect to reaction conditions.

The meta- and para-carboxy substituted substrates 15 and 16 provided good yields of amide products. The use of carbodiimide/HOBT protocols were satisfactory for the coupling of both primary and secondary amines and even aromatic amines (entries 4 and 11). In other embodiments, it was found preferable to employ coupling reagents such as PyBOP or HBTU, for example case of isopropylamine (entry 9). In one preferred embodiment, conditions using these coupling reagents induce less premature cleavage as compared to the use of carbodiimide reagents.

One example of amide formation with supported boronic acids is that of entry 15 involving 16 and N,N-diethylethylenediamine. The resulting amphoteric p-boronobenzamide product 19h, a known melanoma-seeking agent with potential use in boron neutron capture therapy, was obtained pure in a 75% yield after cleavage from the resin. Previously reported syntheses of 19h involve protection of the boronic acid and extensive manipulations such as successive recrystallizations.

TABLE 8

Amide synthesis from 15 and 16 (FIG. 17).

| Entry | Substrate | Conditions[a] | Product {R[1], R[2]} | Yield[b] (%) | Purity[c] (%) |
|---|---|---|---|---|---|
| 1 | 15 | A | 18a {H, (CH$_2$)$_3$Ph} | 57 | 95 |
| 2 | 15 | A | 18b {H, CH(CH$_3$)$_2$} | 60 | >90 |
| 3 | 15 | A | 18c {H, (CH$_2$)$_3$CH$_3$} | 56 | >90 |
| 4 | 15 | B | 18d {H, Ph} | 82 | >95 |
| 5 | 15 | A | 18e {Et, Et} | 77 | 90 |
| 6 | 15 | A | 18f {Bu, Bu} | 79 | 90 |
| 7 | 15 | A | 18g {CH$_2$Ph, CH$_2$Ph} | 60 | >90 |
| 8 | 16 | B | 19a {H, (CH$_2$)$_3$Ph} | 65 | 95 |
| 9 | 16 | B | 19b {H, CH(CH$_3$)$_2$} | 81 | >95 |
| 10 | 16 | A | 19c {H, (CH$_2$)$_3$CH$_3$} | 64 | 95 |
| 11 | 16 | A | 19d {H, Ph} | 67 | >95 |
| 12 | 16 | A | 19e {Et, Et} | 59 | >90 |
| 13 | 16 | A | 19f {Bu, Bu} | 53 | 90 |
| 14 | 16 | B | 19g {CH$_2$Ph, CH$_2$Ph} | 70 | 95 |
| 15 | 16 | A | 19h {H, CH$_2$CH$_2$NEt$_2$} | 70 | >95 |

[a]Typical scale 0.1 mmol. A: Reactions were carried out by shaking the supported carboxylic acid with the amine (4 equiv), DIC (4 equiv) and HOBT·H$_2$O (4 equiv) in NMP or DMF at rt for 18 h. B: Reactions were carried out by shaking the supported carboxylic acid with the amine (2 equiv), DIPEA (4 equiv), and PyBOP (2 equiv) in DMF at rt for 20 h.
[b]Non optimized yields of crude products after cleavage from the resin with 5% H$_2$O/THF and drying in vacuo for >12 hours. The reported values are an average of mass balance and internal standardization.
[c]Estimated from $^1$H and $^{13}$C NMR data.

Typical procedure for the formation of secondary amides with DIC/HOBT: Preparation of 4-Benzylaminocarbonyl-phenylboronic acid (19a). In a 10 mL pp vessel, resin 16 (100 mg, 0.10 mmol) was swollen in NMP (3.5 mL). Benzylamine (44 µL, 0.40 mmol), HOBt·H$_2$O (61 mg, 0.40 mmol), and 1,3-diisopropylcarbodiimide (63 µL, 0.40 mmol) were successively added and the vessel was shaken for 20 h at rt. The suspension was drained, and the resin was rinsed with NMP (3×), THF (5×), and CH$_2$Cl$_2$ (5×). Cleavage of the resin-bound boronic acid using the standard conditions described above, followed by concentration of the filtrates afforded 19a as a white solid (15 mg, 63% yield by mass; 73% yield by $^1$H NMR with EtOAc int. std.).

Typical procedure for the formation of tertiary amides using PyBroP: Preparation of 4-(di-n-butylamino)-carbonylphenylboronic acid (19f): In a 10 mL pp vessel, resin 16 (150 mg, 0.15 mmol) was swollen in DMF (4 mL). Dibutylamine (101 µL, 0.60 mmol), PyBroP (140 mg, 0.30 mmol), and N,N-diisopropylethylamine (105 µL, 0.60 mmol) were added and the vessel was shaken for 20 h at rt. The suspension was drained, and the resin was rinsed with DMF (3×), THF (5×), and CH$_2$Cl$_2$ (5×). Cleavage of the resin-bound boronic acid using the standard conditions described above, followed by concentration of the filtrates afforded 19f as a white solid (22 mg, 57% yield by mass; 50% yield by $^1$H NMR with EtOAc int. std.).

Typical procedure for the formation of secondary amides using PyBoP: Preparation of 19b. In a 10 mL pp vessel, resin 16 (80 mg, 0.08 mmol) was swollen in DMF (2 mL). Iso-propylamine (14 µL, 0.16 mmol), and PyBOP (84 mg, 0.16 mmol) were added and the vessel was shaken for 20 h at rt. The suspension was drained, and the resin was rinsed with DMF (3×), THF (5×), and CH$_2$Cl$_2$ (6×). Cleavage of the resin-bound boronic acid using the standard conditions described above, followed by concentration of the filtrates afforded 19b as a white solid (13 mg, 82% yield by mass; 80% yield by $^1$H NMR with EtOAc int. std.).

3-(3'-Phenylpropyl-1'-amino)carbonylphenylboronic acid (18a). Off-white solid (60% yield by mass): $^1$H NMR (300 MHz, 5% D$_2$O in CD$_3$OD) δ 8.16 (s, 1 H), 7.88 (d, J=7 Hz, 1 H), 7.80 (d, J=8 Hz, 1 H), 7.41 (t, J=8 Hz, 1 H), 7.28–7.11 (m, 5 H), 3.40 (t, J=7 Hz, 2 H), 2.69 (t, J=7 Hz, 2 H), 1.93 (qn, J=7 Hz, 2 H); $^{13}$C NMR (75 MHz, 5% D$_2$O in CD$_3$OD) δ 170.9, 143.1, 137.9, 135.0, 133.6, 129.9, 129.4, 129.4, 128.7, 126.9, 40.8, 34.4, 32.3; IR (microscope) 3303, 3026, 2925, 1633, 1537 cm$^{-1}$; HRMS (ES, m/z) calcd for C$_{16}$H$_{19}$BNO$_3$ (M+H)$^+$ 284.1452. found 284.1452.

3-iso-Propylaminocarbonylphenylboronic acid (18b). Off-white solid (56% yield by mass; 63% yield by $^1$H NMR with 2,5-dimethylfuran int std): $^1$H NMR (300 MHz, 5% D$_2$O in CD$_3$OD) δ 8.15 (s, 1 H), 7.87 (d, J=7 Hz, 1 H), 7.80 (d, J=8 Hz, 1 H), 7.41 (t, J=8 Hz, 1 H), 4.20 (sp, J=7 Hz, 1 H), 1.25 (d, J=7 Hz, 6 H); $^{13}$C NMR (75 MHz, 5% D$_2$O in CD$_3$OD) δ 170.1, 137.8, 135.3, 133.6, 130.0, 128.7, 43.1, 22.6; IR (microscope) 3335, 2976, 1621, 1536 cm$^{-1}$; HRMS (ES, m/z) calcd for C$_{10}$H$_{15}$BNO$_3$ (M+H)$^+$ 208.1139. found 208.1143.

3-n-Butylaminocarbonylphenylboronic acid (18c). White solid (56% yield by mass; 55% yield by $^1$H NMR with EtOAc int. std.): $^1$H NMR (300 MHz, 5% D$_2$O in CD$_3$OD) δ 8.16 (s, 1 H), 7.88 (d, J=7 Hz, 1 H), 7.80 (d, J=8 Hz, 1 H), 7.41 (t, J=8 Hz, 1 H), 3.37 (t, J=7 Hz, 2 H), 1.65-1-55 (m, 2 H), 1.47–1.35 (m, 2 H), 0.96 (t, J=7 Hz, 3 H); $^{13}$C NMR (75 MHz, 5% D$_2$O in CD$_3$OD) δ 170.8, 137.9, 135.1, 133.5, 129.9, 128.7, 40.7, 32.6, 21.2, 14.1; IR (microscope) 3310, 2954, 1637, 1536 cm$^{-1}$; HRMS (ES, m/z) calcd for C$_{11}$H$_{17}$BNO$_3$ (M+H)$^+$ 222.1296. found 122.1297.

3-Phenylaminocarbonylphenylboronic acid (18d). White solid (81% yield by mass; 83% yield by $^1$H NMR with EtOAc int. std.): $^1$H NMR (300 MHz, 5% D$_2$O in CD$_3$OD) δ 8.29 (s, 1 H), 7.95–7.92 (m, 2 H), 7.69–7.65 (m, 2 H), 7.47 (t, J=8 Hz, 1 H), 7.39–7.32 (m, 2 H), 7.17–7.11 (m, 1 H); $^{13}$C NMR (75 MHz, 5% D$_2$O in CD$_3$OD) δ 169.5, 139.8, 138.3, 135.5, 134.0, 130.3, 129.8, 128.8, 125.7, 122.3; IR (microscope) 3309, 3057, 1644, 1538 cm$^{-1}$; HRMS (ES, m/z) calcd for C$_{13}$H$_{13}$BNO$_3$ (M+H)$^+$ 242.0983. found 242.0980.

3-(Diethylamino)carbonylphenylboronic acid (18e). White solid (77% yield by mass; 77% yield by $^1$H NMR with EtOAc int. std.): $^1$H NMR (300 MHz, 5% D$_2$O in CD$_3$OD) δ 7.81 (d, J=6.6 Hz, 1 H), 7.71 (s, 1 H), 7.44–7.36 (m, 2 H), 3.57–3.51 (m, 2 H), 3.31–3.25 (m, 2 H), 1.27–1.22 (m, 3 H), 1.12–1.07 (m, 3 H); $^{13}$C NMR (75 MHz, 5% D$_2$O in CD$_3$OD) δ 174.1, 137.2, 136.0, 132.4, 128.8, 128.8, 45.0, 40.8, 14.3, 13.1; IR (microscope) 3314, 3065, 2979, 2475, 1587 cm$^{-1}$HRMS (ES, m/z) calcd for C$_{11}$H$_{17}$BNO$_3$ (M+H)$^+$ 222.1296. found 222.1298.

3-(Di-n-butylamino)carbonylphenylboronic acid (18f). Clear, colorless gum (77% yield by mass; 81% yield by $^1$H NMR with EtOAc int. std.): $^1$H NMR (300 MHz, 5% D$_2$O in CD$_3$OD) δ 7.82 (d, J=7 Hz, 1 H), 7.71 (s, 1 H), 7.44–7.35 (m, 2 H), 3.50 (t, J=7 Hz, 2 H), 3.23 (t, J=7 Hz, 2 H), 1.71–1.62 (m, 2 H), 1.55–1.36 (m, 4 H), 1.17–1.05 (m, 2 H), 0.99 (t, J=7 Hz, 3 H), 0.75 (t, J=7 Hz, 3 H); $^{13}$C NMR (75 MHz, 5% D$_2$O in CD$_3$OD) δ 174.5, 137.2, 135.9, 132.6, 129.1, 128.8, 50.3, 46.0, 31.7, 30.7, 21.2, 20.6, 14.2, 13.8; IR (microscope) 3362, 2961, 1610, 1416, 1344 cm$^{-1}$; HRMS (ES, m/z) calcd for C$_{15}$H$_{25}$BNO$_3$ (M+H)$^+$ 278.1922. found 278.1930.

3-(Dibenzylamino)carbonylphenylboronic acid (18g). White solid (61% yield by mass; 59% yield by $^1$H NMR with EtOAc int std): $^1$H NMR (300 MHz, 5% D$_2$O in CD$_3$OD) δ 7.86–7.84 (m, 2 H), 7.50–7.47 (m, 1 H), 7.41–7.30 (m, 9 H), 7.11–7.09 (m, 2 H), 4.66 (s, 2 H), 4.41 (s, 2 H); $^{13}$C NMR (125 MHz, 5% D$_2$O in CD$_3$OD) δ 175.1, 137.9, 137.4, 136.4, 136.3, 132.9, 129.9, 129.8, 129.2, 128.9, 128.8, 128.7, 128.3, 53.3; IR (microscope) 3364, 3030, 2926, 1606 cm$^{-1}$; HRMS (ES, m/z) calcd for C$_{21}$H$_{21}$BNO$_3$ (M+H)$^+$ 346.1609. found 346.1599.

4-(3'-Phenylpropyl-1'-amino)carbonylphenylboronic acid (19a). White solid (64% yield by mass; 65% yield by $^1$H NMR with EtOAc int std): $^1$H NMR (300 MHz, 5% D$_2$O in CD$_3$OD) δ 7.80 (d, J=8 Hz, 2 H), 7.72 (d, J=8 Hz, 2 H), 7.28–7.10 (m, 5 H), 3.39 (t, J=7 Hz, 2 H), 2.72–2.64 (m, 2 H), 1.92 (qn, J=7 Hz, 2 H); $^{13}$C NMR (125 MHz, 5% D$_2$O in CD$_3$OD) δ 170.5, 143.0, 137.1, 134.9, 129.4, 127.2, 126.9, 40.9, 34.5, 32.4; IR (microscope) 3310, 2924, 1633, 1545 cm$^{-1}$; HRMS (ES, m/z) calcd for CH$_{16}$H$_{19}$BNO$_3$ (M+H)$^+$ 284.1458. found 284.1456.

4-iso-Propylaminocarbonylphenylboronic acid (19b). Off-white solid (82% yield by mass; 80% yield by $^1$H NMR with EtOAc int. std.): $^1$H NMR (300 MHz, 5% D$_2$O in CD$_3$OD) δ 7.81–7.72 (m, 4 H), 31.8 (h, J=7 Hz, 1 H), 1.24 (d, J=7 Hz, 6 H); $^{13}$C NMR (125 MHz, 5% D$_2$O in CD$_3$OD) δ 169.7, 137.3, 134.8, 127.2, 43.3, 22.7; IR (microscope) 3239, 2972, 1633, 1548 cm$^{-1}$; HRMS (ES, m/z) calcd for C$_{10}$H$_{15}$BNO$_3$ (M+H)$^+$ 208.1139. found 208.1140.

4-n-Butylaminocarbonylphenylboronic acid (19c). White solid (63% yield by mass): $^1$H NMR (300 MHz, 5% D$_2$O in CD$_3$OD) δ 7.81 (d, J=8 Hz, 2 H), 7.74 (d, J=8 Hz, 2 H), 3.37 (t, J=7 Hz, 2 H), 1.65–1.55 (m, 2 H), 1.47–1.34 (m, 2 H), 0.96 (t, J=7 Hz, 3 H); $^{13}$C NMR (75 MHz, 5% D$_2$O in CD$_3$OD) δ 170.5, 137.1, 134.9, 127.2, 40.8, 32.6, 21.2, 14.1; IR (microscope) 3257, 2958, 1634, 1546 cm$^{-1}$; HRMS (ES, m/z) calcd for C$_{11}$H$_{17}$BNO$_3$ (M+H)$^+$ 222.1296. found 222.1303.

4-Phenylaminocarbonylphenylboronic acid (19d). White solid (67% yield by mass): $^1$H NMR (300 MHz, 5% D$_2$O in CD$_3$OD) δ 7.87 (s, 4 H), 7.69–7.65 (m, 2 H), 7.39–7.32 (m, 2 H), 7.14 (m, 1 H); $^{13}$C NMR (100 MHz, 5% D$_2$O in CD$_3$OD) δ 169.1, 139.7, 137.6, 135.0, 129.8, 127.6, 125.7, 122.4; IR (microscope) 3301, 3042, 1643, 1537 cm$^{-1}$; HRMS (ES, m/z) calcd for C$_{13}$H$_{13}$BNO$_3$ (M+H)$^+$ 242.0983. found 242.0984.

4(Diethylamino)carbonylphenylboronic acid (19e). Yellow gum (59% yield by mass): $^1$H NMR (300 MHz, 5% D$_2$O in CD$_3$OD) δ 7.81 (d, J=7 Hz, 2 H), 7.31 (d, J=8 Hz, 2 H), 3.53 (q, J=7 Hz, 2 H), 3.27 (q, J=7 Hz, 2 H), 1.24 (t, J=7 Hz, 3 H), 1.10 (t, J=7 HZ, 3 H), $^{13}$C NMR (75 MHz, 5% D$_2$O in CD$_3$OD) δ 173.8, 139.5, 135.1, 126.2, 44.9, 40.8, 14.4, 13.1; IR (microscope) 3380, 2974, 1598, 1549 cm$^{-1}$; HRMS (ES, m/z) calcd for C$_{11}$H$_{17}$BNO$_3$ (M+H)$^+$ 222.1296. found 222.1298.

4-(Di-n-butylamino)carbonylphenylboronic acid (19f). White solid (57% yield by mass; 50% yield by $^1$H NMR with EtOAc int. std.): $^1$H NMR (300 MHz, 5% D$_2$O in CD$_3$OD) δ 7.80 (d, J=8 Hz, 2 H), 7.29 (d, J=8 Hz, 2 H), 3.49 (t, J=8 Hz, 2 H), 3.22 (t, J=8 Hz, 2 H), 1.71–1.61 (m, 2 H), 1.54–1.34 (m, 4 H), 1.17–1.05 (m, 2 H), 0.99 (t, J=7 Hz, 3 H), 0.75 (t, J=7 Hz, 3 H); $^{13}$C NMR (75 MHz, 5% D$_2$O in CD$_3$OD) δ 174.2, 139.6, 135.1, 126.4, 50.2, 45.9, 31.7, 30.7, 21.2, 20.7, 14.2, 13.8; IR (microscope) 3276, 2958, 1603, 1514 cm$^{-1}$; HRMS (ES, m/z) calcd for C$_{15}$H$_{25}$BNO$_3$ (M+H)$^+$ 278.1922. found 278.1928.

4-(Dibenzylamino)carbonylphenylboronic acid (19g). White solid (69% yield by mass; 70% yield by $^1$H NMR with EtOAc int. std.): $^1$H NMR (300 MHz, 5% D$_2$O in CD$_3$OD) δ 7.79 (d, J=8 Hz, 2 H), 7.42 (d, J=8 Hz, 2 H), 7.34–7.30 (m, 8 H), 7.13–7.11 (m, 2 H), 4.67 (s, 2 H), 4.42 (s, 2 H); $^{13}$C NMR (75 MHz, CD$_3$OD) δ 174.8, 138.0, 137.5, 135.1, 129.9, 129.2, 128.8, 128.2, 126.6, 53.1; IR (microscope) 3357, 2918, 1605, 1341 cm$^{-1}$; HRMS (ES, m/z) calcd for C$_{21}$H$_{21}$BNO$_3$ (M+H)$^+$ 346.1609. found 346.1608.

4-[2'-(Diethylamino)ethylamino]carbonylphenylboronic acid (19h). White solid (71% yield by mass; 70% yield by $^1$H NMR with EtOAc int. std): $^1$H NMR (300 MHz, 5% D$_2$O in CD$_3$OD) δ 7.80–7.70 (m, 4 H), 3.56 (t, J=7 Hz, 2 H), 2.89 (t, J=7 Hz, 2 H), 2.82 (q, J=7 Hz, 4 H), 1.15 (t, J=7 Hz, 6 H); $^{13}$C NMR (125 MHz, 5% D$_2$O in CD$_3$OD) δ 171.0, 134.9, 127.0, 52.6, 48.4, 37.8, 11.0; IR (microscope) 3326, 2970, 2820, 1638, 1543, 1432 cm$^{-1}$; HRMS (ES, m/z) calcd for C$_{13}$H$_{22}$BNO$_3$ (M+H)$^+$ 265.1718. found 265.1718.

Example 10

Reaction of Carboxylic Acids with Supported Anilines

Figure 18:
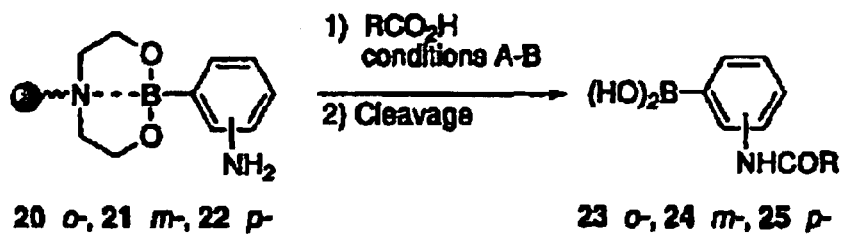
FIG. 18 is a schematic summarizing the reaction of carboxylic acids with DEAM-PS supported anilines as described in detail in Example 10.

Example 3 detailed that anilide-derivatized boronic acids can be obtained from the reaction of DEAM-PS supported aminobenzeneboronic acids with acid chlorides. Referring now to FIG. 18 and Table 9, anilide-derivatized boronic acids of this were isolated in a variable range of yields (ca. 50–80%) by reaction of carboxylic acids with supported anilines 20–22. All three substitution patterns were explored with this type of chemistry.

In one preferred embodiment, the use of PyBOP as a coupling agent in NMP or DMF for 20 hours at room temperature was preferred. In one preferred embodiment for entries 3–6, PyBOP was preferred over use of carbodiimide. A wide variety of carboxylic acids were tested, including Fmoc-protected alanine (entry 9), which provided a 51% yield of the expected amide product 24e. All meta- and para-substituted substrates provided the expected anilide products.

Figure 21:
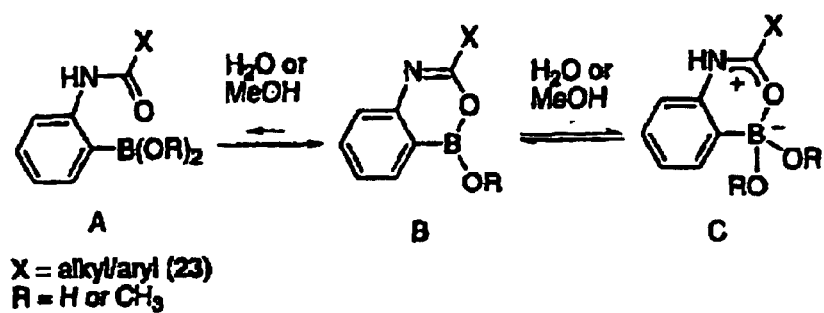
FIG. 21 is a schematic of the possible forms of ortho-acylaminobenzeneboronic acids (compound 23) in hydroxylic solvents (e.g. water or methanol) as described in detail in Example 10. B is the naphtalene-like form originating from dehydrative cyclization of A. C is the putative ate form arising from 1,4-addition of water or methanol.

Referring now to FIG. 21, ES-MS analysis, suggested that the ortho-substituted anilides 23 existed in a cyclic mono-dehydrated form B. This may be the case in aqueous or alcohol solutions as well owing to the partial aromatic character of these boron-containing heterocycles. It may be that these and similar compounds like ureas can add one molecule of water or alcohol by 1,4-addition and thus exist in equilibrium with form C of FIG. 21. ortho-Acylamino-substituted benzeneboronic acids 23 were found to have limited solubility in all solvents, thus they were also characterized as their pinacol ester (form A) in order to unambiguously demonstrate their identity by $^1$H and $^{13}$C NMR.

TABLE 9

Anilide synthesis from anilines 20–22 (FIG. 19).[a]

| Entry | Substrate | Conditions[a] | Product {R} | Yield[b] (%) | Purity[c] (%) |
|---|---|---|---|---|---|
| 1 | 20 | B | 23a {CH$_2$CH$_3$} | 61 | >95 |
| 2 | 20 | B | 23b {Ph} | 60 | >90 |
| 3 | 21 | A | 24a {CH$_2$CH$_3$} | 42 | >90 |
| 4 | 21 | A | 24b {Ph} | 52 | >95 |
| 5 | 21 | B | 24a {CH$_2$CH$_3$} | 72 | 95 |
| 6 | 21 | B | 24b {Ph} | 82 | 95 |
| 7 | 21 | B | 24c {CH$_2$CH$_2$CH=CH$_2$} | 70 | >95 |
| 8 | 21 | B | 24d {CCPh} | 75 | >95 |
| 9 | 21 | B | 24e {(S)CH(Me)NHFmoc} | 51 | 95 |
| 10 | 22 | B | 25a {CH$_2$CH$_3$} | 61 | >95 |
| 11 | 22 | B | 25b {Ph} | 46 | 95 |

[a]Typical scale 0.1 mmol. A: Reactions were carried out by shaking the supported aniline with the carboxylic acid (2 equiv), DIC (2 equiv) and HOBT-H$_2$O (2 equiv) in DMF at rt for 20 h. B: Reactions were carried out by shaking the supported aniline with the carboxylic acid (2 equiv), PyBOP (2 equiv) in NMP at rt for 20 h.
[b]Non optimized yields of crude products after cleavage from the resin with 5% H$_2$O/THF and drying in vacuo for >12 hours. The reported values are usually an average of mass balance and internal standardization.
[c]Estimated from $^1$H and $^{13}$C NMR data.

Typical procedure for the formation of anilides using DIC/HOBT: Preparation of 24a. In a 10 mL pp reaction vessel, resin 21 (155 mg, 0.150 mmol, theor. loading: 0.966 mmol g$^{-1}$) was swollen in DMF (4.0 mL). Propionic acid (22 µL, 0.30 mmol), HOBt.H$_2$O (46 mg, 0.30 mmol), and 1,3-diisopropylcarbodiimide (47 µL, 0.30 mmol) were added successively and the reaction vessel was shaken for 19 h at rt. The suspension was drained, and the resin was rinsed with DMF (3×), THF (5×), and CH$_2$Cl$_2$ (5×). Cleavage of the resin-bound boronic acid under standard conditions, followed by concentration of the filtrates afforded 24a as a brown solid (11 mg, 42% yield by mass; 41% yield by $^1$H NMR with 2,5-dimethylfuran int. std.).

Typical procedure for the formation of anilides using PyBOP: Preparation of 24a. Resin 21 (102 mg, 0.0965 mmol, theor. loading: 0.946 mmol g$^{-1}$) was added to a 10 mL polypropylene vessel and swollen in NMP (1.5 mL). PyBoP (100 mg, 0.193 mmol), DIPEA (67 µL, 0.386 mmol), and propionic acid (14 µL, 0.193 mmol) were added in the given order and the reaction vessel was shaken for 19 h at rt. The suspension was drained, and the resin was rinsed with NMP (3×), CH$_2$Cl$_2$ (5×), and THF (3×). The product was then cleaved from the resin using the standard conditions described above. The product rinses were combined, concentrated under reduced pressure and dried under high vacuum overnight to afford a yellow solid (13 mg, 76% yield by mass; 68% yield by $^1$H NMR with EtOAc int. std.).

N-(Propionyl)-2-aminophenylboronic acid (23a). White solid (61% yield by mass): $^1$H NMR (300 MHz, CD$_3$OD) δ7.46–7.43 (m, 1H), 7.31–7.20 (m, 2H), 7.03–7.00 (m, 1H), 2.66 (q, J=8 Hz, 2H), 1.33 (t, J=8 Hz, 3H); IR (microscope) 3100–2400, 3000, 2979, 1640, 1601 cm$^{-1}$; HRMS (ES, m/z) calcd for C$_9$H$_{12}$BNO$_3$Na (M+Na)$^+$ 216.0802. found 216.0806. A $^{13}$C NMR spectrum of 23a could not be obtained due to low solubility. Therefore, compound 23a was derivatized as its pinacol ester 23a' in order to obtain a $^{13}$C NMR spectrum. Compound 23a was cleaved from resin 20 with 10% pinacol/THF and purified by flash chromatography on silica gel using 1/1 ethyl acetate/CH$_2$Cl$_2$ as eluent giving a white solid. $^1$H NMR (500 MHz, CD$_3$OD) δ 8.16 (br d, J=6 Hz, 1H), 7.71–7.70 (m, 1H), 7.35 (t, J=8 Hz, 1H), 7.05 (t, J=7 Hz, 1H), 2.29 (q, J=8 Hz, 2H), 1.35 (s, 12H), 1.18 (t, J=8 Hz, 3H); $^{13}$C NMR (125 MHz, CDCl$_3$) δ 172.2, 143.4, 135.6, 131.9, 123.4, 118.6, 83.7, 30.6, 25.1, 9.4.

N-(Benzoyl)-2-aminophenylboronic acid (23b). White solid (60% yield by mass): $^1$H NMR (500 MHz, CD$_3$OD) δ 8.18–8.16 (m, 2H), 7.76–7.73 (m, 1H), 7.65–7.62 (m, 2H), 7.53–7.51 (m, 1H), 7.37–7.28 (m, 3H); IR (microscope) 3203, 3063, 2958, 1624, 1602 cm$^{-1}$; HRMS (ES, m/z) calcd for C$_{13}$H$_{12}$BNO$_3$Na (M+Na)$^+$ 264.0802. found 264.0798. A $^{13}$C NMR spectrum of 23b could not be obtained due to low solubility. Therefore, compound 23b was derivatized as its pinacol ester 23b' in order to obtain a $^{13}$C NMR spectrum. Compound 23b was cleaved from resin 20 with 10% pinacol/THF and purified by flash chromatography on silica gel using ethyl acetate as eluent to give a white solid. $^1$H NMR (500 MHz, CD$_3$OD) δ 8.70 (d, J=8 Hz, 1H), 8.02 (m, 2 H), 7.80 (m, 1 H), 7.54–7.45 (m, 4 H), 7.08 (m, 1H), 1.39 (s, 12H); $^{13}$C NMR (125 MHz, CDCl$_3$) δ 165.2, 144.9, 136.2, 135.3, 133.0, 131.6, 128.5, 127.2, 123.0, 119.1, 84.5, 24.9.

N-(Propionyl)-3-aminophenylboronic acid (24a). Yellow solid (76% yield by mass; 68% yield by $^1$H NMR with EtOAc int. std.): $^1$H NMR (300 MHz, 5% D$_2$O in CD$_3$OD) δ 7.77 (s, 1 H), 7.60 (d, J=8 Hz, 1 H), 7.45 (d, J=7 Hz, 1 H), 7.26 (t, J=8 Hz, 1 H), 2.38 (q, J=8 Hz, 2 H), 1.19 (t, J=8 Hz, 3 H); $^{13}$C NMR (75 MHz, 5% D$_2$O in CD$_3$OD) δ 175.6, 139.0, 130.7, 129.0, 126.9, 123.5, 31.0, 10.3; IR (microscope) 3303, 3057, 2980, 1665, 1615 cm$^{-1}$; HRMS (ES, m/z) calcd for C$_9$H$_{12}$BNO$_3$ (M+H)$^+$ 194.0983. found 194.0981.

N-(Benzoyl)-3-aminophenylboronic acid (24b). Beige solid (86% yield by mass; 77% yield by $^1$H NMR with EtOAc int. std.): $^1$H NMR (300 MHz, 5% D$_2$O in CD$_3$OD) δ 7.93–7.90 (m, 3 H), 7.73 (d, J=8 Hz, 1 H), 7.60–7.47 (m, 4 H), 7.34 (t, J=8 Hz, 1 H); $^{13}$C NMR (75 MHz, 5% D$_2$O in CD$_3$OD) δ 169.0, 142.1 (broad), 138.9, 136.2, 132.9, 131.3, 129.7, 129.1, 128.6, 128.0, 124.7; IR (microscope) 3317, 3066, 3045, 1645, 1603, 1580 cm$^{-1}$; HRMS (ES, m/z) calcd for C$_{13}$H$_{13}$BNO$_3$ (M+H)$^+$ 242.0983. found 242.0984.

N-(3'-Butenylcarbonyl)-3-aminophenylboronic acid (24c). White solid (74% yield by mass, 66% yield by $^1$H NMR with EtOAc int. std.): $^1$H NMR (300 MHz, 5% D$_2$O in CD$_3$OD) δ 7.76 (s, 1H), 7.59 (d, J=8 Hz, 1H), 7.46 (d, J=7 Hz, 1H), 7.27 (t, J=8 Hz, 1H), 5.94–8.81 (m, 1H), 5.12–4.97 (m, 2H), 2.47–2.41 (m, 4H); $^{13}$C NMR (75 MHz, 5% D$_2$O in CD$_3$OD) δ 174.0, 138.9, 138.2, 135.3 (broad), 130.8, 129.0, 126.9, 123.6, 116.0, 37.2, 30.8; IR (microscope) 3319, 3079, 2978, 1660, 1644, 1606, 1532 cm$^{-1}$; HRMS (ES, m/z) calcd for C$_{11}$H$_{15}$BNO$_3$ (M+H)$^+$ 220.1145. found 220.1146.

N-(2'-Phenylethynylcarbonyl)-3-aminophenylboronic acid (24d). Yellow solid (76% yield by mass, 73% yield by $^1$H NMR with EtOAc int. std.): $^1$H NMR (300 MHz, 5% D$_2$O in CD$_3$OD) δ 7.84 (br s, 1H), 7.69–7.67 (m, 1H), 7.63–7.60 (m, 2H); 7.54–7.50 (m, 2H), 7.48–7.39 (m, 3H), 7.36–7.30 (m, 1 H); $^{13}$C NMR (75 MHz, 5% D$_2$O in CD$_3$OD) δ 153.5, 143.9 (broad), 138.4, 133.6, 131.6, 131.5, 129.8, 129.3, 126,7, 123.7, 121.2, 87.0, 84.0; IR (microscope) 3263, 3056, 2211, 1642, 1583 cm$^{-1}$; HRMS (ES, m/z) calcd for C$_{15}$H$_{12}$BNO$_3$Na (M+Na)$^+$ 288.0808. found 288.0806.

N-[N'-(9-Fluorenylmethoxycarbonyl)-L-alaninyl]-3-aminophenylboronic acid (24e). Yellow solid (53% yield by mass, 48% yield by $^1$H NMR with EtOAc int. std.): $^1$H NMR (300 MHz, 5% D$_2$O in THF-d$_8$) δ 7.82 (m, 2H), 7.73 (d, J=7 Hz, 2H), 7.63 (t, J=7 Hz, 2H), 7.47 (d, J=7 Hz, 1H), 7.32–7.14 (m, 5H), 4.35 (q, J=7 Hz, 1H), 4.29–4.14 (m, 3H), 1.45 (d, J=7 Hz, 3H); $^{13}$C NMR (75 MHz, 5% $D_2O$ in THF-$d_8$) δ 172.1, 157.2, 145.3, 145.1, 142.2, 139.2, 141.4 (broad), 130.4, 128.4, 127.9. 126.2, 126.1, 122.3, 120.6, 51.9, 48.2, 19.1; IR (microscope) 3307, 3065, 2977, 1673, 1610 cm$^{-1}$; HRMS (ES, m/z) calcd for $C_{24}H_{23}BN_2O_5Na$ (M+Na)$^+$ 453.1598. found. 453.1598.

N-(Propionyl)-4-aminophenylboronic acid (25a). Cream-colored solid (61% yield by $^1$H NMR with EtOAc int std.): $^1$H NMR (300 MHz, 5% $D_2O$ in $CD_3OD$) δ 7.73–7.66 (m, 2H), 7.54–7.49 (m, 2H), 2.38 (q, J=8 Hz, 2H), 1.18 (t, J=8 Hz, 3H); $^{13}$C NMR (75 MHz, 5% $D_2O$ in $CD_3OD$) δ 175.9, 141.6, 135.6, 130.0 (broad), 120.1, 31.1, 10.3; IR (microscope) 3306, 3044, 2979, 1666, 1594 cm$^{-1}$; HRMS (ES, m/z) calcd for $C_9H_{13}BNO_3$ (M+H)$^+$ 194.0983. found 194.0985.

N-(Benzoyl)-4-aminophenylboronic acid (25b). White solid (47% yield by mass, 45% yield by $^1$H NMR with EtOAc int. std.): $^1$H NMR (300 MHz, 5% $D_2O$ in $CD_3OD$) δ 7.92–7.89 (m, 2H), 7.76–7.73 (m, 2H), 7.69–7.64 (m, 2H), 7.60–7.47 (m, 3H); $^{13}$C NMR (75 MHz, 5% $D_2O$ in $CD_3OD$) δ 169.1, 136.1, 135.6, 133.0, 129.7, 128.6, 121.1; IR (microscope) 3313, 3040, 1650, 1601, 1588 cm$^{-1}$; HRMS (ES, m/z) calcd for $C_{13}H_{12}BNO_3Na$ (M+Na)$^+$ 264.0808. found 264.0803.

Example 11

Synthesis of Ureas and Thioureas

Figure 19:
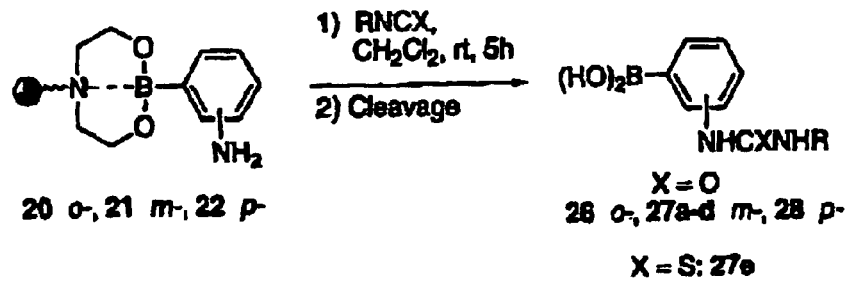
FIG. 19 is a schematic of the reaction of DEAM-PS supported anilines for the formation of ureas as described in detail in Example 11.

Referring now to FIG. 19 and Table 10, ureas of type 27 and 28 were isolated from the reaction of the respective meta- and para-substituted anilines 21 and 22 with various isocyanates of different electronic nature, in dichloromethane for 5–6 hours at room temperature. An example of thiourea was also made with ease (27e, entry 5). Yields of products were excellent for all reported examples regardless of the electronic characteristics of the isocyanate reagent. Using conditions as outlined in Table 10, the ortho-substituted substrate 20 provided products 26 accompanied with varying amounts of double addition products.

TABLE 10

Synthesis of ureas from anilines 21 and 22 (FIG. 19).

| Entry | Substrate | Conditions[a] | Product {R} | Yield[b] (%) | Purity[c] (%) |
|---|---|---|---|---|---|
| 1 | 21 | B | 27a {CH(CH$_3$)$_2$} | 66 | 95 |
| 2 | 21 | A | 27b {Ph} | 79 | >95 |
| 3 | 21 | A | 27c {4-MeO—C$_6$H$_4$} | 82 | >95 |
| 4 | 21 | A | 27d {4-NO$_2$—C$_6$H$_4$} | 80 | >95 |
| 5 | 21 | A | 27e {Ph} | 85 | 95 |
| 6 | 22 | B | 28a {CH(CH$_3$)$_2$} | 65 | >95 |
| 7 | 22 | A | 28b {Ph} | 85 | >95 |
| 8 | 22 | A | 28c {4-MeO—C$_6$H$_4$} | 88 | >95 |
| 9 | 22 | A | 28d {4-NO$_2$—C$_6$H$_4$} | 92 | 95 |

[a]Typical scale 0.1 mmol. A: Reactions were carried out by shaking the supported aniline with the isocyanate (2 equiv), in $CH_2Cl_2$ at rt for 5–6 h. B: longer reaction time (20–45 h).
[b]Non optimized yields of crude products after cleavage from the resin with 5% $H_2O$/THF and drying in vacuo for >12 hours. The reported values are usually an average of mass balance and internal standardization.
[c]Estimated from $^1$H and $^{13}$C NMR data.

Typical procedure for the formation of ureas: Preparation of 27a. In a 10 mL pp reaction vessel, resin 21 (104 mg, 0.10 mmol, theor. loading: 0.96 mmol g$^{-1}$) was swollen in $CH_2Cl_2$ (2 mL). Isopropylisocyanate (20 μL, 0.20 mmol) was added and the vessel was shaken for 7 h at rt. The suspension was drained, and the resin was rinsed with $CH_2Cl_2$ (8×). The product was then cleaved from the resin using the standard conditions described above. The combined filtrates were concentrated under reduced pressure and dried under high vacuum overnight to afford a brown solid (16 mg, 76% yield by mass; 66% yield by $^1$H NMR with EtOAc int. std.).

N-(iso-Propylaminocarbonyl)-3-aminophenylboronic acid (27a). Brown solid (76% yield by mass; 66% yield by $^1$H NMR with EtOAc int std): $^1$H NMR (300 MHz, 5% $D_2O$ in $CD_3OD$) δ 7.58 (s, 1 H), 7.43 (d, J=8 Hz, 1 H), 7.35 (d, J=7 Hz, 1 H), 7.22 (t, J=8 Hz, 1 H), 3.87 (heptet, J=7 Hz, 1 H), 1.16 (d, J=7 Hz, 6 H); $^{13}$C NMR(7 MHz, 5% $D_2O$ in $CD_3OD$) δ 157.9, 140.1, 129.1, 129.0, 125.8, 122.6, 42.9, 23.4 (the resolution of this $^{13}$C NMR was poor because of the limited solubility of the product in most commercial deuterated solvents); IR (microscope) 3347, 3036, 2985, 1639, 1568, 1343 cm$^{-1}$; HRMS (ES, m/z) calcd for HRMS (ES, m/z) calcd for $C_{10}H_{16}BN_2O_3$ (M+H)$^+$ 223.1248. found 223.1250.

N-(Phenylaminocarbonyl)-3-aminophenylboronic acid (27b). Beige solid (79% yield by $^1$H NMR wit EtOAc int std): $^1$H NMR (300 MHz, 5% $D_2O$ in $CD_3OD$) δ 7.67 (s, 1 H), 7.52 (d, J=8 Hz, 1 H), 7.42–7.38 (m, 3 H), 7.30–7.23 (m, 3 H), 7.03–6.97 (m, 1 H); $^{13}$C NMR (75 MHz, 5% $D_2O$ in $CD_3OD$) δ 155.7, 140.5, 139.6, 129.9, 129.5, 129.1, 126.1, 123.9, 122.8, 120.5; IR (microscope) 3317, 1639, 1567, 1343 cm$^{-1}$; HRMS (ES, m/z) calcd for $C_{13}H_{14}BN_2O_3$ (M+H)$^+$ 257.1092. found 257.1093.

N-(4'-Methoxyphenylaminocarbonyl)-3-aminophenyl-boronic acid (27c). Beige solid (85% yield by mass; 78% yield by $^1$H NMR with EtOAc int std): $^1$H NMR (300 MHz, 5% $D_2O$ in $CD_3OD$) δ 7.65 (s, 1 H), 7.50 (d, J=8 Hz, 1H), 7.40–7.38 (m, 1 H), 7.32–7.22 (m, 3H), 6.89–6.84 (m, 2H), 3.76 (s, 3H); $^{13}$C NMR (75 MHz, 5% $D_2O$ in $CD_3OD$) δ 157.3, 156.1, 139.7, 133.3, 129.4, 129.1, 126.0, 122.9, 122.7, 115.2, 56.0; IR (microscope) 3317, 3046, 2960, 1643, 1572, 1346 cm$^{-1}$; HRMS (ES, m/z) calcd for $C_{14}H_{16}BN_2O_4$ (M+H)$^+$ 287.1198. found 287.1197.

N-(4'-Nitrophenylaminocarbonyl)-3-aminophenyl-boronic acid (27d). Bright yellow solid (85% yield by mass; 74% yield by $^1$H NMR with EtOAc int std): $^1$H NMR (300 MHz, 5% $D_2O$ in $CD_3OD$) δ 8.20–8.15 (m, 2H), 7.68–7.63 (m, 3H), 7.55 (d, J=8 Hz, 1H), 7.45–7.42 (m, 1H), 7.28 (t, J=8 Hz, 1H); $^{13}$C NMR (75 MHz, 5% $D_2O$ in $CD_3OD$) δ 154.6, 147.4, 143.4, 139.1, 130.0, 129.2, 126.2, 126.0, 122.9, 119.0; IR (microscope) 3365, 1705, 1552, 1329 cm$^{-1}$; HRMS (ES, m/z) calcd for $C_{13}H_{13}BN_3O_5$ (M+H)$^+$ 302.0943. found 302.0943.

N-(Phenylaminothiocarbonyl)-3-aminophenylboronic acid (27e). Resin 21 (100 mg, 0.0946 mmol, theor. loading: 0.946 mmol g$^{-1}$) was added to a 10 mL pp vessel and swollen in $CH_2Cl_2$ (2 mL). A solution of phenyl isothiocyanate (10% (v/v) in $CH_3CN$, 226 μL, 0.189 mmol) was added and the vessel was shaken for 20 h at rt. The suspension was drained, and the resin was rinsed with $CH_2Cl_2$ (5×). The product was then cleaved from the resin using the standard conditions described above. The combined filtrates were concentrated under reduced pressure and dried under high vacuum overnight to afford a cream colored solid (21 mg, 88% yield by mass; 82% yield by $^1$H NMR with EtOAc int. std.): $^1$H NMR (300 MHz, 5% D$_2$O in CD$_3$OD) δ 7.66 (s, 1H), 7.59 (d, J=7 Hz, 1H), 7.47 (br d, J=8 Hz, 1H), 7.41–7.32 (m, 5H), 7.23–7.17 (m, 1H); $^{13}$C NMR (75 MHz, 5% D$_2$O in CD$_3$OD) δ 181.9, 139.9, 139.2, 132.6, 131.5, 130.0, 129.3, 128.4, 127.1, 126.2; IR (microscope) 3214, 3054, 1597, 1530, 1497, 1429, 1344 cm$^{-1}$; HRMS (ES, m/z) calcd for C$_{13}$H$_{14}$BN$_2$O$_2$S (M+1)$^+$ 273.0869. found 273.0871.

N-(iso-Propylaminocarbonyl)-4-aminophenylboronic acid (28a). Cream solid (65% yield by mass): $^1$H NMR (300 MHz, 5% D$_2$O in CD$_3$OD) δ 7.68–7.61 (m, 2H), 7.33–7.28 (m, 2H), 3.86 (sp, J=7 Hz, 1H), 1.15 (d, J=7 Hz, 6H); $^{13}$C NMR (75 MHz, 5% D$_2$O in CD$_3$OD) δ 157.4, 143.0, 135.7, 127.7 (broad), 118.7, 42.8, 23.3; IR (microscope) 3327, 3045, 2973, 1650, 1595 cm$^{-1}$; HRMS (ES, m/z) calcd C$_{10}$H$_{15}$BN$_2$O$_3$Na (M+Na)$^+$ 245.1068. found 245.1075.

N-(Phenylaminocarbonyl)-4-aminophenylboronic acid (28b). White solid (85% yield by mass): $^1$H NMR (300 MHz, 5% D$_2$O in CD$_3$OD) δ 7.73–7.66 (m, 2H), 7.42–7.37 (m, 4H), 7.31–7.25 (m, 2H), 7.04–6.99 (m, 1H); $^{13}$C NMR (75 MHz, 5% D$_2$O in CD$_3$OD) δ 155.3, 142.4, 140.3, 135.8, 129.9, 128.1 (broad), 124.0, 120.5, 119.0; IR (microscope) 3391, 3313, 3057, 1671, 1591, 1531, 1499 cm$^{-1}$; HRMS (ES, m/z) calcd for C$_{13}$H$_{14}$BN$_2$O$_3$ (M+H)$^+$ 257.1092. found 257.1092.

N-(4'-Methoxyphenylaminocarbonyl)-4-aminophenyl-boronic acid (28c). Cream solid (91% yield by mass; 84% yield by $^1$H NMR with EtOAc int std): $^1$H NMR (300 MHz, 5% D$_2$O in CD$_3$OD) δ 7.68–7.65 (m, 2H), 7.38–7.36 (m, 2H), 7.29 (d, J=9 Hz, 2H), 6.86 (d, J=9 Hz, 2H), 3.75 (s, 3H) $^{13}$C NMR (75 MHz, 5% D$_2$O in THF-d$_8$) δ 156.0, 153.6, 143.1, 135.8, 134.2, 127.4 (broad), 120.8, 117.7, 114.6, 55.7; IR (microscope) 3390, 3305, 3051, 2961, 1662, 1589 cm$^{-1}$; HRMS (ES, m/z) calcd for C$_{14}$H$_{16}$BN$_2$O$_4$ (M+H)$^+$ 287.1198. found 287.1201.

N-(4'-Nitrophenylaminocarbonyl)-4-aminophenyl-boronic acid (28d). Bright yellow solid (92% yield by mass): $^1$H NMR (300 MHz, 5% D$_2$O in CD$_3$OD) δ 8.16 (d, J=9 Hz, 2H) 7.75–7.62 (m,4H), 7.41 (d, J=8 Hz, 2H); $^{13}$C NMR (300 MHz, 5% D$_2$O in CD$_3$OD) δ 154.1, 147.2, 143.5, 141.9 (broad), 141.4(broad), 135.7, 125.9, 119.3, 118.9; IR (microscope) 3439, 3354, 3303, 3109, 1724, 1621, 1598, 1574, 1546, 1521, 1498 cm$^{-1}$; HRMS (ES, m/z) calcd for C$_{13}$H$_{13}$BN$_3$O$_5$ (M+H)$^+$ 302.0943. found 302.0940.

Example 12

Ugi Multicomponent Reaction

Figure 22:
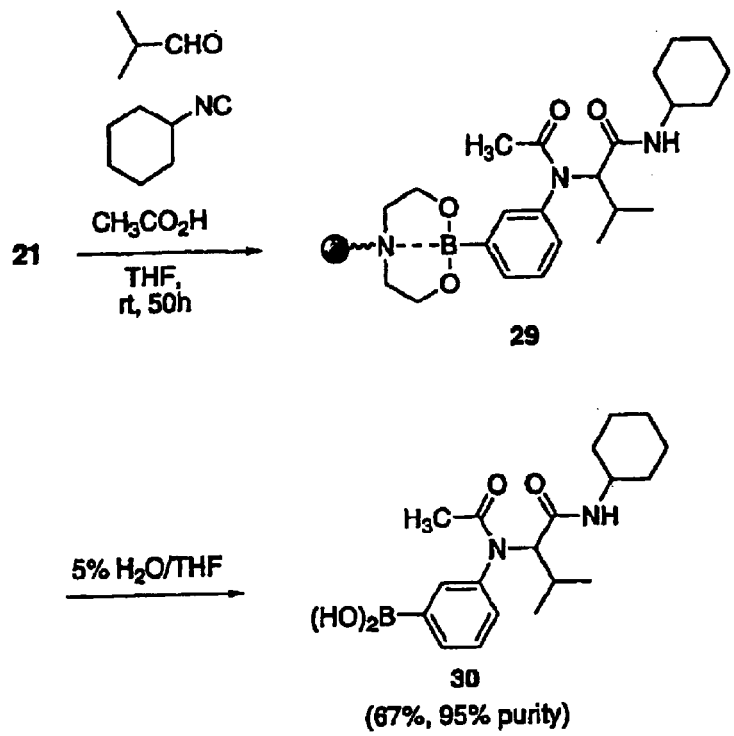
FIG. 22 is a schematic of a Ugi multicomponent reaction using a DEAM-PS supported aniline as described in detail in Example 12.

Referring now to FIG. 22, a Ugi multicomponent reaction (Ugi, I.; Dömling, A.; Hörl, W. *Endeavour* 1994, 18, 115–122), was carried out on DEAM-PS supported aniline 21 of FIG. 18 and provided dipeptide derivative 30 in high purity after cleavage from resin 29.

N-(Acetyl)-N-(1'-cyclohexylaminocarbonyl-2'-methylpropane)-3-aminophenyl boronic acid (30). Resin 21 (122 mg, 0.115 mmol, theor. loading: 0.946 mmol g$^{-1}$) was added to a 10 mL pp vessel and swollen in NMP (1 mL). Isobutyraldehyde (105 μL, 1.150 mmol), glacial acetic acid (66 μL, 1.150 mmol), and cyclohexylisonitrile (120 μL, 1.150 mmol) were added in the given order and the vessel was shaken for 50 h at rt. The suspension was drained, and the resin was red with THF (5×), CH$_2$Cl$_2$ (5×), and THF (5×). The product was then cleaved from the resin using the standard conditions described above. The product rinses were combined, concentrated under reduced pressure and dried under high vacuum overnight to afford a cream solid (26 mg, 67% yield by mass): $^1$H NMR (300 MHz, 5% D$_2$O in CD$_3$OD)$^i$ δ 7.77 (d, J=7 Hz, 1H), 7.59 (s, 1H), 7.41 (t, J=8 Hz, 1H), 7.30 (d, J=8 Hz, 1H), 4.63 (d, J=11 Hz, 1H), 3.62–3.54 (m, 1H), 2.17–2.04 (m, 1H), 1.90–1.83 (m, 1H), 1.78 (s, 3H); 1.78–169 (m, 3H), 1.63–1.51 (m, 1H), 1.41–1.13 (m, 5H); 1.04 (d, J=7 Hz, 3H), 0.87 (d, J=7 Hz, 3H); $^{13}$C NMR (125 MHz, 5% D$_2$O in CD$_3$OD) δ 174.3, 170.8, 140.9, 136.5 (broad), 135.8 (broad), 135.1, 132.0 (broad), 129.7, 68.4, 49.8, 33.5, 28.6, 26.6, 26.0, 23.5, 20.3, 19.9; IR (microscope) 3240, 3067, 2963, 2931, 1632, 1558 cm$^{-1}$; HRMS (ES, m/z) calcd for C$_{19}$H$_{29}$BN$_2$O$_4$Na (M+Na)$^+$ 383.2118. found 383.2111.

Example 13

Derivatization and Sequential Transformations of Multifunctional Boronic Acids

Figure 23:
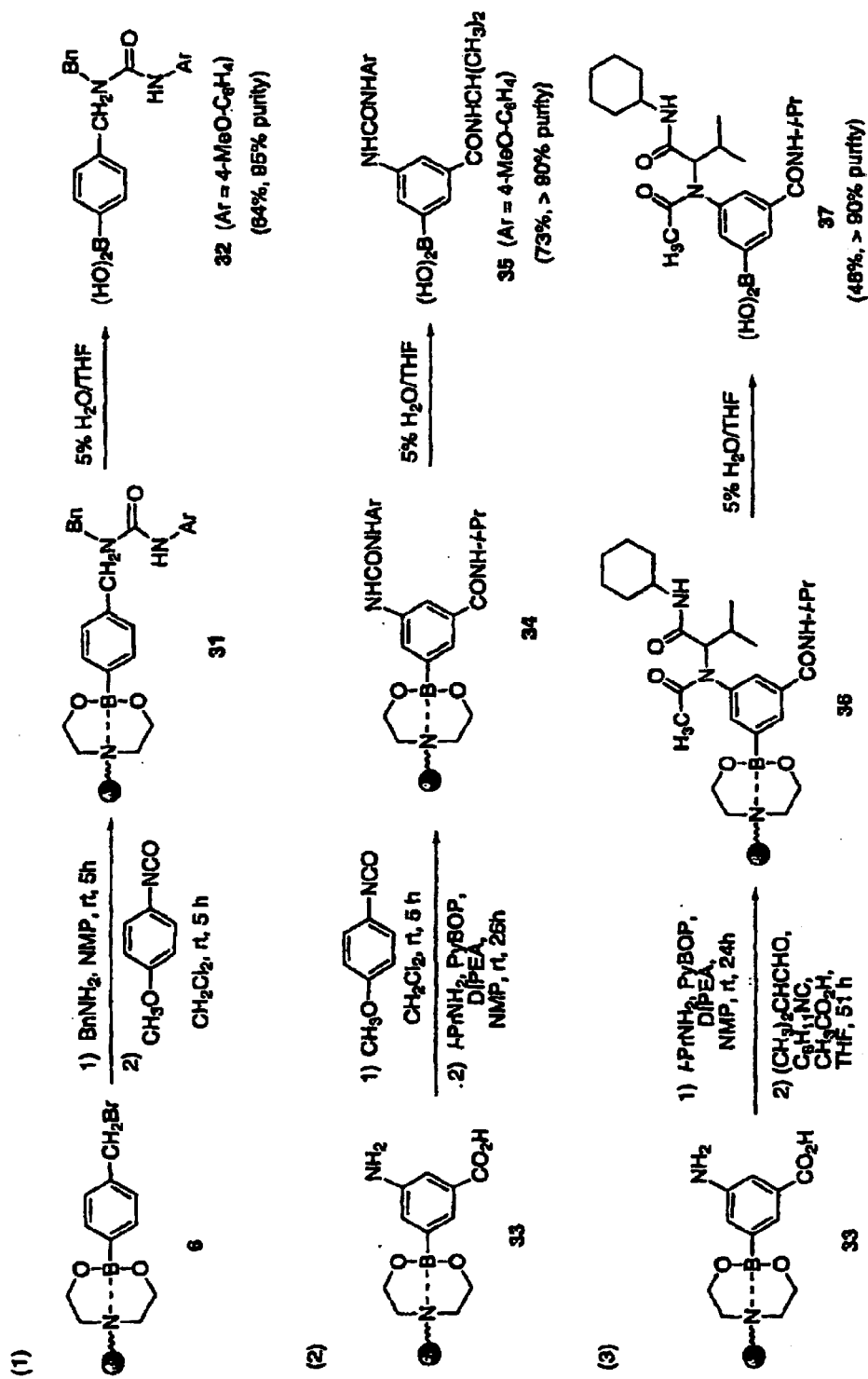
FIG. 23 is a schematic of three equations showing the derivatiziation and sequential transformation of multifunctional boronic acids as described in detail in Example 13.

Referring now to FIG. 23, derivatization of multifunctional boronic acids and sequential transformations were also examined. As shown in scheme (1) of FIG. 23, the para-bromomethyl substituted substrate 6 was first treated with benzylamine as described above (Table 6). Following resin washes, the resulting substitution product was reacted with p-methoxyphenylisocyanate to give 31. The expected boronic acid product 32 was obtained in 64% yield and high purity after cleavage from the support.

As shown in scheme (2) of FIG. 23, in a similar fashion, supported 3-amino-5-carboxyphenylboronic acid (33) was treated with p-methoxyphenyl isocyanate. The carboxyl functionality was then coupled with isopropylamine to give after treatment of resin 34 with wet THF, the final product 35 in 73% yield.

Referring now to scheme (3) of FIG. 23, amide formation could also be effected as first step on the same substrate, which can then undergo a Ugi reaction involving the aniline functionality, ultimately providing boronic acid 37.

N-(Benzyl)-N-(4'-methoxyphenylaminocarbonyl)-4-aminomethylphenylboronic acid (32). The general procedure for substitution of a bromomethyl-substituted arylboronic acid using benzylamine (vide supra) was carried out on resin 6 and was followed directly by the general procedure for the formation of ureas using 4-methoxyphenyl isocyanate (vide supra) to yield a yellow solid (67% yield by mass; 60% yield by $^1$H NMR with EtOAc int. std.): $^1$H NMR (300 MHz, 5% D$_2$O in CD$_3$OD) δ 7.72 (d, J=8 Hz, 2H), 7.36–7.28 (m, 3H), 7.26–7.16 (m, 6H), 6.83 (d, J=9 Hz, 2H), 4.56 (s, 4H), 3.74 (s, 3H); $^{13}$C NMR (75 MHz, 5% D$_2$O in CD$_3$OD) δ 159.1, 157.7, 140.9, 138.8, 135.3, 133.3, 129.8, 128.5, 128.5, 127.6, 125.1, 114.9, 55.9, 50.7, 50.6; IR (microscope) 3327, 3030, 2932, 1638, 1610, 1512 cm$^{-1}$; HRMS (ES, m/z) calcd for C$_{22}$H$_{23}$BN$_2$O$_4$Na (M+Na)$^+$ 413.1643. found 413.1631.

5-(iso-Propylaminocarbonyl)-N-(4'-methoxyphenyl-aminocarbonyl)-3-aminophenylboronic acid (35). The general procedure for the formation of ureas using 4-methoxyphenyl isocyanate (vide supra) was carried out on resin 33 followed directly by the general procedure for the formation of amides using iso-propyl amine, PyBoP and DIPEA (vide supra) to yield a yellow solid (77% yield by mass; 65% yield by $^1$H NMR with EtOAc int. std.): $^1$H NMR (300 MHz, 5% D$_2$O in CD$_3$OD, the sample was made up >16 h prior to running in order to obtain full exchange of the secondary amide proton with deuterated solvents) δ 7.89 (br s, 1H), 7.80 (br s, 2H), 7.31 (d, J=9 Hz, 2H), 6.88 (d, J=9 Hz, 2H) 4.17 (h, J=7 Hz, 1H), 3.76 (s, 3H), 1.24 (d, J=7 Hz, 6H); $^{13}$C NMR (75 MHz, 5% D$_2$O in CD$_3$OD) δ 170.1, 157.3, 156.0, 140.0, 136.2, 133.0, 128.9, 128.0, 123.0, 121.2, 115.2, 56.1, 43.2, 22.6; IR (microscope) 3399, 3310, 2970, 1664, 1626, 1599, 1547, 1514 cm$^{-1}$; HRMS (ES, m/z) calcd for $C_{18}H_{22}BN_3O_5Na$ (M+Na)$^+$ 394.1550. found 394.1549.

N-(Acetyl)-N-(1'-cyclohexylaminocarbonyl-2'-methylpropane)-3-amino-5-(isopropylaminocarbonyl) phenylboronic acid (37). The general procedure for the formation of secondary amides using iso-propylamine, PyBoP and DIPEA (vide supra) was carried out on resin 33 and was followed directly by the general procedure for the formation of 30 using iso-butyraldehyde, glacial acetic acid and cyclohexylisonitrile (vide supra) to yield a white solid (53% yield by mass; 42% yield by $^1$H NMR with EtOAc int. std.): $^1$H NMR (500 MHz, 5% $D_2O$ in $CD_3OD$, the sample was made up >16 h prior to running in order to obtain full exchange of the secondary amide proton with deuterated solvents) δ 8.17 (s, 1H), 7.74 (s, 1H) 7.68 (s, 1H), 4.72 (d, J=11 Hz, 1H), 4.19 (heptet, J=7 Hz, 1H), 3.62–3.48 (m, 1H), 2.11–2.06 (m, 1H), 1.88–1.85 (m, 1H), 1.80 (s, 3H), 1.78–1.70 (m, 3H), 1.62–160 (m, 1H), 1.38–1.15 (m, 11H), 1.06 (d, J=7 Hz, 3H) 0.88 (d, J=7 Hz, 3H); $^{13}$C NMR (75 MHz, 5% $D_2O$ in $CD_3OD$) δ 174.1, 170.6, 169.0, 143.5, 141.0 (broad), 136.8, 133.6, 131.1 (broad), 68.9, 67.9, 43.3, 33.5, 33.5, 28.7, 26.5, 26.4, 26.0, 26.0, 23.6, 22.5. 20.2, 19.8; IR (microscope) 3308, 2969, 2932, 2856, 1640, 1586, 1537, 1428 cm$^{-1}$; HRMS (ES, m/z) calcd for $C_{23}H_{37}BN_3O_5$ (M+H)$^+$ 446.2821. found 446.2816.

A number of embodiments of the invention have been described. Nevertheless, it will be understood that various modifications may be made without departing from the spirit and scope of the invention. Accordingly, other embodiments are within the scope of the following claims.

What is claimed is:

1. A dihydroxyalkylaminoalkyl- or dihydroxyalkylaminobenzyl-conjugated solid support, wherein the dihydroxyalkylamino moiety comprises the formula $HO(CH_2)_2N(CH_2)_2OH$, and wherein the solid support comprises a cross-linked polystyrene having about 1% to 2% cross-linking.

2. The solid support of claim 1, wherein the dihydroxyalkylaminoalkyl group or dihydroxyalkylaminobenzyl group is a diethanolaminoethyl, a diethanolaminoethyl, a diethanolaminopropyl, a diethanolaminobutyl group or a diethanolaminobenzyl group.

3. The solid support of claim 1, wherein the cross-linked polystyrene comprises a cross-linked poly(styrene-divinylbenzene) (PS-DVB) copolymer having about 1% to 2% cross-linking.

4. The solid support of claim 1, wherein tho solid support comprises a cross-linked poly(styrene-divinylbenzene) copolymer having about 1% cross-linking.

5. An N,N-diethanolaminomethyl-conjugated solid support, wherein the solid support comprises a cross-linked polystyrene having about 1% to 2% cross-linking.

6. The solid support of claim 5, wherein the solid support comprises a cross-linked poly(styrene-divinylbenzene) copolymer having about 1% to 2% cross-linking.

7. The solid support of claim 6, wherein the solid support comprises a cross-linked poly(styrene-divinylbenzene) copolymer having about 1% cross-linking.

* * * * *